(12) United States Patent
Breitenbucher et al.

(10) Patent No.: US 8,901,111 B2
(45) Date of Patent: Dec. 2, 2014

(54) ARYL-SUBSTITUTED HETEROCYCLIC UREA MODULATORS OF FATTY ACID AMIDE HYDROLASE

(75) Inventors: J. Guy Breitenbucher, Escondido, CA (US); Mark S. Tichenor, San Diego, CA (US); Jeffrey E. Merit, Stanford, CA (US); Natalie A. Hawryluk, San Diego, CA (US); Alison L. Chambers, San Diego, CA (US); John M. Keith, San Diego, CA (US)

(73) Assignee: Janssen Pharmaceutica NV (BE)

( * ) Notice: Subject to any disclaimer, the term of this patent is extended or adjusted under 35 U.S.C. 154(b) by 233 days.

(21) Appl. No.: 13/375,855

(22) PCT Filed: Jun. 4, 2010

(86) PCT No.: PCT/US2010/037388
§ 371 (c)(1),
(2), (4) Date: Dec. 2, 2011

(87) PCT Pub. No.: WO2010/141809
PCT Pub. Date: Dec. 9, 2010

(65) Prior Publication Data
US 2012/0088741 A1    Apr. 12, 2012

Related U.S. Application Data

(60) Provisional application No. 61/184,606, filed on Jun. 5, 2009.

(51) Int. Cl.
| | | |
|---|---|---|
| *A61K 31/616* | (2006.01) | |
| *C07D 401/12* | (2006.01) | |
| *C07D 405/14* | (2006.01) | |
| *C07D 401/14* | (2006.01) | |
| *C07D 471/04* | (2006.01) | |
| *A61K 31/5025* | (2006.01) | |
| *A61K 31/4427* | (2006.01) | |
| *A61K 31/443* | (2006.01) | |
| *A61K 31/4709* | (2006.01) | |
| *A61K 31/4725* | (2006.01) | |
| *A61K 31/4439* | (2006.01) | |
| *A61K 31/437* | (2006.01) | |
| *C12N 9/99* | (2006.01) | |
| *A61P 25/04* | (2006.01) | |
| *A61P 29/00* | (2006.01) | |
| *A61P 25/22* | (2006.01) | |
| *A61P 25/24* | (2006.01) | |
| *A61P 25/00* | (2006.01) | |
| *A61P 25/14* | (2006.01) | |
| *A61P 25/28* | (2006.01) | |
| *A61P 25/08* | (2006.01) | |
| *A61P 25/16* | (2006.01) | |
| *A61P 1/08* | (2006.01) | |
| *A61P 15/00* | (2006.01) | |
| *A61P 27/06* | (2006.01) | |
| *A61P 1/00* | (2006.01) | |
| *A61P 1/04* | (2006.01) | |
| *A61P 1/12* | (2006.01) | |
| *A61P 19/02* | (2006.01) | |
| *A61P 9/12* | (2006.01) | |
| *A61P 35/00* | (2006.01) | |
| *A61P 3/10* | (2006.01) | |
| *A61P 17/04* | (2006.01) | |
| *A61P 19/10* | (2006.01) | |
| *A61P 3/00* | (2006.01) | |
| *C07D 487/04* | (2006.01) | |
| *C07D 413/12* | (2006.01) | |

(52) U.S. Cl.
CPC ............ *C07D 487/04* (2013.01); *C07D 413/12* (2013.01); *C07D 401/14* (2013.01); *C07D 401/12* (2013.01); *C07D 471/04* (2013.01)
USPC ................... 514/210.18; 514/161; 546/268.1; 546/283.7; 546/157; 546/143; 546/268.4; 546/113

(58) Field of Classification Search
USPC ........... 514/161, 210.18; 544/236; 546/268.1, 546/283.7, 157, 143, 268.4, 113; 435/184
See application file for complete search history.

(56) References Cited

U.S. PATENT DOCUMENTS

| 6,100,279 A | 8/2000 | Vaccaro et al. |
| 6,124,299 A | 9/2000 | Baindur et al. |

(Continued)

FOREIGN PATENT DOCUMENTS

| WO | WO 02 087569 A1 | 11/2002 |
| WO | WO 03 047569 A1 | 6/2003 |

(Continued)

OTHER PUBLICATIONS

Ahn et al "Discovery and Characterization of a Highly Selective FAAH Inhibitor That Reduces Inflammatory Pain" Chemisty and Biology Current Biology 2009 vol. 16 (4) pp. 411-420.
Bagshawe et al "Antibody-Directed Enzyme Prodrug Therapy: A Review" Drug Dev Res 1995 vol. 34 pp. 220-230.
Baker et al "Endocannabinoids Control Spasticity in a Multiple Sclerosis Model" FASEB J 2001 vol. 15(2) pp. 300-302.
Baker et al "Cannabinoids Control Spasticity and Tremor in Multiple Sclerosis Model" Nature 2000 vol. 404 pp. 84-87.

(Continued)

*Primary Examiner* — Kendra D Carter
*Assistant Examiner* — Jason A Deck
(74) *Attorney, Agent, or Firm* — Mary A. Appollina

(57) ABSTRACT

Certain aryl-substituted heterocyclic urea compounds are described, which are useful as FAAH inhibitors. Such compounds may be used in pharmaceutical compositions and methods for the treatment of disease states, disorders, and conditions mediated by fatty acid amide hydrolase (FAAH) activity, such as anxiety, pain, inflammation, sleep disorders, eating disorders, energy metabolism disorders, and movement disorders (e.g., multiple sclerosis).

15 Claims, No Drawings

(56) References Cited

U.S. PATENT DOCUMENTS

| | | | |
|---|---|---|---|
| 6,387,900 | B1 | 5/2002 | Pevarello et al. |
| 6,395,740 | B1 | 5/2002 | Baindur et al. |
| 6,881,741 | B2 | 4/2005 | Chan Chun Kong et al. |
| 2003/0149036 | A1 | 8/2003 | Flohr et al. |
| 2006/0173184 | A1 | 8/2006 | Apodaca et al. |
| 2007/0004741 | A1 | 1/2007 | Apodaca et al. |
| 2007/0270433 | A1 | 11/2007 | Brinkman et al. |
| 2009/0062294 | A1 | 3/2009 | Apodaca et al. |
| 2009/0325956 | A1* | 12/2009 | Taniguchi et al. ......... 514/235.5 |

FOREIGN PATENT DOCUMENTS

| | | | |
|---|---|---|---|
| WO | WO 2004 033652 A2 | | 4/2004 |
| WO | WO 2006 085108 A1 | | 8/2006 |
| WO | WO 2007 096251 A1 | | 8/2007 |
| WO | WO 2008 023720 A1 | | 2/2008 |
| WO | WO 2008 024139 A1 | | 2/2008 |
| WO | WO 2008 047229 A2 | | 4/2008 |
| WO | WO 2008 075064 A1 | | 6/2008 |
| WO | WO 2008 153752 A2 | | 12/2008 |
| WO | WO 2010068452 A1 * | | 6/2010 |

OTHER PUBLICATIONS

Berge et al "Pharmaceutical Salts" J Pharm Sci 1977 vol. 66 pp. 1-19.
Bertolini et al "A New Rational Hypothesis for the Pharmacore of the Active Metabolite of Leflunomide, a Potent Immunosuppressive Drug" J Med Chem 1997 vol. 4O pp. 2011-2016.
Bodor et al "Novel Approaches to the Design of Safer Drugs: Soft Drugs and Site Specific Chemical Deliery Sytems" Adv Drug Res 1984 vol. 13 pp. 255-331.
Boger et al "Exceptionally Potent Inhibitors of Fatty Acid Amide Hydrolse" The Enzyme Responsible for Degradation of Endogenous Oleamide and Anandamide Proc Natl Acad Sci USA 2000 vol. 97(1) pp. 5044-5049.
Bouaboula et al "Anandamide Induced PPARγ Transcriptional Activation and 3T3-LI Preadipocyte Differentiation" J Pharmacol 2005 vol. 517 pp. 174-181.
Bundgaard et al Design of Prodrugs Ed. H. Bundgaard Elsevier 1985.
Cravatt et al "Molecular Characterization of an Enzyme That Degrades Neuromodulatory Fatty-Acid Amides" Nature 1996 vol. 384 pp. 83-87.
Cravatt et al "Supersensitivity to Anandamide and Enhanced Endogenous Cannabinoid Signaling in Mice Lacking Fatty Acid Amide Hydrolase" Proc Natl Acad Sci USA 2001 vol. 98(16) pp. 9371-9376.
Cravatt et al "Novel Mechanistic Class of Fatty Acid Amide Hydrolase Inhibitors With Remarkable Selectivity" Biochemistry 2007 vol. 46(45) pp. 13019-13030.
Croxfsord et al "Cannabinoid-Mediated Neuroprotection, Not Immunosuppression, May Be More Relevant to Multiple Sclerosis" J Neuroimmunol 2008 vol. 183 pp. 120-129.
Devane et al "Isolation and Structure of a Brain Constituent That Binds to the Cannabinoid Receptor" Science 1992 vol. 258 pp. 1946-1949.
Fleisher et al "Improved Oral Drug Delivery: Solubility Limitations Overcome by the Use of Prodrugs" Adv Drug Delivery Rev 1996 vol. 19 pp. 115-130.
Gobbi et al "Antidepressant-Like Activity and Modulation of Brain Monoaminergic Transmission by Blockade of Anandamide Hydrolysis" PNAS USA 2005 vol. 102(51) pp. 18620-18625.
Goya et al "Recent Advanced in Cannabinoid Receptor Agonists and Antagonists" Expert Opin Ther Patents 2000 vol. 10 pp. 1529-1538.
Holt et al "Inhibitors of Fatty Acid Amide Hydrolase Reduce Carrageenan-Induced Hind Paw Inflammation in Pentobarbital-Treated Mice: Comparison With Indomethacin and Possible Involvement of Cannabinoid Receptors" Br J Pharmacol 2005 vol. 146 pp. 467-476.
Karsak et al "Cannabinoid Receptor Type 2 Gene Is Associated With Human Osteoporosis" Hum Mol Genet 2005 vol. 14 pp. 3389-3396.
Kathuria et al "Modulation of Anxiety Through Blockade of Anandamide Hydrolysis" Nat Med 2003 vol. 9(1) pp. 76-81.
Kirkham et al "Endocannabinoid Levels in Rat Limbic Forebrain and Hypothalamus in Relation to Fasting Feeding and Satiation: Stimulation of Eating by 1-Arachidonlyl Glycerol" Br $_j$ of Pharmacol 2002 vol. 136 pp. 550-557.
Lambert et al "The Palmitoylethanolamide Family: A New Class of Anti-Inflammatory Agents" Curr Med Chem 2002 vol. 9(6) pp. 663-674.
Larsen et al Design and Application of Prodrugs Drug Design and Development Krogsgaard-Larsen et al Eds Harwood Academic Publishers 1991.
Mendelson et al "The Hypnotic Actions of Fatty Acid Amide, Oleamide" Neuropsychopharmacology 2001 vol. 25 pp. S36-S39.
Ofek et al "Peripheral Cannabinoid Receptor CB2 Regulates Bone Mass" Proc Natl Acad Sci USA 2006 vol. 103 pp. 696-701.
Overton et al "GPR119 a Novel G Protein-Coupled Receptor Target for the Treatment of Type-2 Diabetes and Obesity" Br J Pharmacol 2008 vol. 153 pp. S76-S81.
Piomelli et al "The Molecular Logic of Endocannabinoid Signalling" Nat Rev Neurosci 2003 vol. 4(11) pp. 873-884.
Plutzky et al "Preventing Type 3 Diabetes and Cardiovascular Disease in Metabolic Syndrome: The Role of PPARα" Diab Vasc Dis Res 2007 vol. 4 Supp 3 pp. S12-S14.
Robinson et al "Discovery of the Hemifumarate and (A-Alanyloxy)Methyl Ether as Prodrugs of an Antirheumatic Oxindole: Prodrugs for the Enolic OH Group" J Med Chem 1996 vol. 39 pp. 10-18.
Robson et al "Therapeutic Aspects of *Cannabis* and Cannabinoids" Br J Psychiatry 2001 vol. 178 pp. 107-115.
Rodriguez De Fonesca et al "An Anorexic Lipid Mediator Regulated by Feding" Nature 2001 vol. 414 pp. 209-212.
Cravatt et al "Chemical Characterization of a Family of Brain Lipids That Induce Sleep" Science 1995 vol. 268 pp. 1506-1509.
Shan et al "Prodrug Strategies Based on Intramolecular Cyclization Reactions" J Pharm Sci 1997 vol. 86(7) pp. 765-767.
Steffens et al "Low Dose Oral Cannabinoid Therapy Reduces Progression of Atherosclerosis in Mice" Nature 2005 vol. 434 pp. 782-786.
Svendsen et al "Does the Cannabinoid Dronabinol Reduce Central Pain in Multiple Sclerosis? Randomised Double Blind Placebo Controlled Crossover Trial" Br Med J 2004 vol. 329(253) pp. 1-8.
Stahl et al Handbook of Pharmaceutical Salts Properties Selection and Use Stahl and Wermuth Eds Wiley-VCH and VHCA Zurich 2002.
Ueda et al "Purification and Characterization of an Acid Amidase Selective for N—Palmitoylethanolamine a Putative Endogenous Anti-Inflammatory Substance" J Biol Chem 2001 vol. 276(38) pp. 35552-35557.
Varvel et al "Fatty Acid Amide Hydrolase (−/−) Mice Exhibit an Increased Sensitivity to the Disruptive Effects of Anandamide or Oleamide in a Working Memory Water Maze Task" J Pharmacol Exp Ther 2006 vol. 317(1) pp. 251-257.
Wang et al "Structure Based Design of Novel Irreversible FAAH Inhibitors" Bioorg Med Chem Letts 2008 vol. 19(20) pp. 5970-5974.
Webb et al "Genetic Deletion of Fatty Acid Amide Hydrolase Results in Improved Long-Term Outcome in Chronic Autoimmune Encephalitis" Neurosci Lett 2008 vol. 439 pp. 106-110.
International Search Reportfor Corresponding PCT/US2010/037388 Mailed on.Aug. 3, 2010.

* cited by examiner

ARYL-SUBSTITUTED HETEROCYCLIC UREA MODULATORS OF FATTY ACID AMIDE HYDROLASE

CROSS-REFERENCE TO RELATED APPLICATIONS

This application is a national phase of International Application No. PCT/US2010/037388 filed Jun. 4, 2010 and claims benefit of priority under 35 U.S.C. §119(e) of U.S. Provisional Application No. 61/184,606 filed on Jun. 5, 2009.

FIELD OF THE INVENTION

The present invention relates to certain aryl-substituted heterocyclic urea compounds, pharmaceutical compositions containing them, and methods of using them for the treatment of disease states, disorders, and conditions mediated by fatty acid amide hydrolase (FAAH) activity.

BACKGROUND OF THE INVENTION

Medicinal benefits have been attributed to the cannabis plant for centuries. The primary bioactive constituent of cannabis is $\Delta^9$-tetrahydrocannabinol (THC). The discovery of THC eventually led to the identification of two endogenous cannabinoid receptors responsible for its pharmacological actions, namely $CB_1$ and $CB_2$ (Goya, *Exp. Opin. Ther. Patents* 2000, 10, 1529). These discoveries not only established the site of action of THC, but also inspired inquiries into the endogenous agonists of these receptors, or "endocannabinoids". The first endocannabinoid identified was the fatty acid amide anandamide (AEA). AEA itself elicits many of the pharmacological effects of exogenous cannabinoids (Piomelli, *Nat. Rev. Neurosci.* 2003, 4(11), 873).

The catabolism of AEA is primarily attributable to the integral membrane bound protein fatty acid amide hydrolase (FAAH), which hydrolyzes AEA to arachidonic acid. FAAH was characterized in 1996 by Cravatt and co-workers (Cravatt, *Nature* 1996, 384, 83). It was subsequently determined that FAAH is additionally responsible for the catabolism of a large number of important lipid signaling fatty acid amides including: another major endocannabinoid, 2-arachidonoylglycerol (2-AG) (*Science* 1992, 258, 1946-1949); the sleep-inducing substance, oleamide (OEA) (*Science* 1995, 268, 1506); the appetite-suppressing agent, N-oleoylethanolamine (Rodriguez de Fonesca, *Nature* 2001, 414, 209); and the anti-inflammatory agent, palmitoylethanolamide (PEA) (Lambert, *Curr. Med. Chem.* 2002, 9(6), 663).

Small-molecule inhibitors of FAAH should elevate the concentrations of these endogenous signaling lipids and thereby produce their associated beneficial pharmacological effects. There have been some reports of the effects of various FAAH inhibitors in pre-clinical models. In particular, two carbamate-based inhibitors of FAAH were reported to have analgesic properties in animal models. In rats, BMS-1 (see WO 02/087569), which has the structure shown below, was reported to have an analgesic effect in the Chung spinal nerve ligation model of neuropathic pain, and the Hargraves test of acute thermal nociception. URB-597 was reported to have efficacy in the zero plus maze model of anxiety in rats, as well as analgesic efficacy in the rat hot plate and formalin tests (Kathuria, *Nat. Med.* 2003, 9(1), 76). The sulfonylfluoride AM374 was also shown to significantly reduce spasticity in chronic relapsing experimental autoimmune encephalomyelitis (CREAE) mice, an animal model of multiple sclerosis (Baker, *FASEB J.* 2001, 15(2), 300).

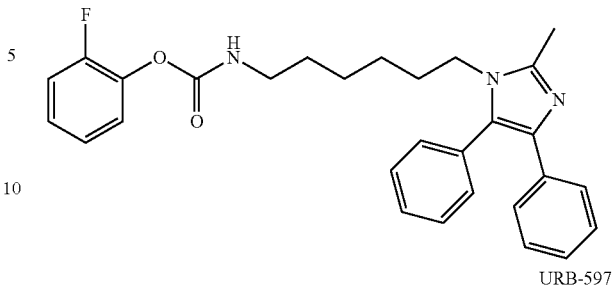

BMS-1

URB-597

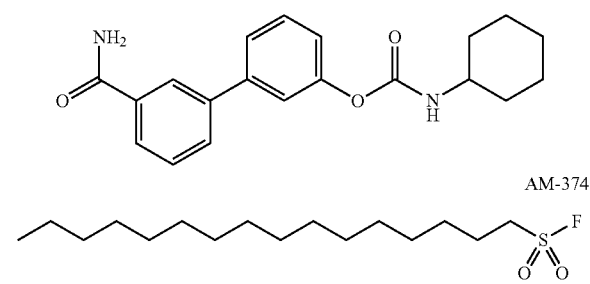

AM-374

In addition, the oxazolopyridine ketone OL-135 is reported to be a potent inhibitor of FAAH, and has been reported to have analgesic activity in both the hot plate and tail emersion tests of thermal nociception in rats (WO 04/033652).

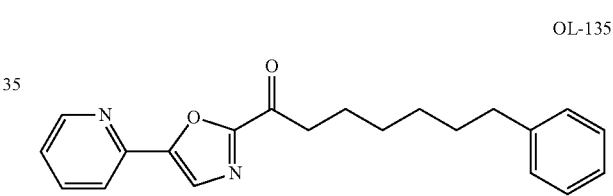

OL-135

Results of research on the effects of certain exogenous cannabinoids has elucidated that a FAAH inhibitor may be useful for treating various conditions, diseases, disorders, or symptoms. These include pain, nausea/emesis, anorexia, spasticity, movement disorders, epilepsy and glaucoma. To date, approved therapeutic uses for cannabinoids include the relief of chemotherapy-induced nausea and emesis among patients with cancer and appetite enhancement in patients with HIV/AIDS who experience anorexia as a result of wasting syndrome. Two products are commercially available in some countries for these indications, namely, dronabinol (Marinol®) and nabilone.

Apart from the approved indications, a therapeutic field that has received much attention for cannabinoid use is analgesia, i.e., the treatment of pain. Five small randomized controlled trials showed that THC is superior to placebo, producing dose-related analgesia (Robson, *Br. J. Psychiatry* 2001, 178, 107-115). Atlantic Pharmaceuticals is reported to be developing a synthetic cannabinoid, CT-3, a 1,1-dimethyl heptyl derivative of the carboxylic metabolite of tetrahydrocannabinol, as an orally active analgesic and anti-inflammatory agent. A pilot phase II trial in chronic neuropathic pain with CT-3 was reportedly initiated in Germany in May 2002.

A number of individuals with locomotor activity-related diseases, such as multiple sclerosis have claimed a benefit from cannabis for both disease-related pain and spasticity, with support from small controlled trials (Croxford et el., *J. Neuroimmunol*, 2008, 193, 120-9; Svendsen, *Br. Med. J.* 2004, 329, 253). Likewise, various victims of spinal cord injuries, such as paraplegia, have reported that their painful spasms are alleviated after smoking marijuana. A report showing that cannabinoids appear to control spasticity and tremor in the CREAE model of multiple sclerosis demonstrated that these effects are mediated by $CB_1$ and $CB_2$ receptors (Baker, *Nature* 2000, 404, 84-87). Phase 3 clinical trials have been undertaken in multiple sclerosis and spinal cord injury patients with a narrow ratio mixture of tetrahydrocannabinol/cannabidiol (THC/CBD). It has been reported that FAAH knockout mice consistently recover to a better clinical score than wild type controls, and this improvement is not a result of anti-inflammatory activity, but rather may reflect some neuroprotection or remyelination promoting effect of lack of the enzyme (Webb et al, *Neurosci Lett.,* 2008, vol. 439, 106-110).

Reports of small-scale controlled trials to investigate other potential commercial uses of cannabinoids have been made. Trials in volunteers have been reported to have confirmed that oral, injected, and smoked cannabinoids produced dose-related reductions in intraocular pressure (IOP) and therefore may relieve glaucoma symptoms. Ophthalmologists have prescribed cannabis for patients with glaucoma in whom other drugs have failed to adequately control intraocular pressure (Robson, 2001, supra).

Inhibition of FAAH using a small-molecule inhibitor may be advantageous compared to treatment with a direct-acting $CB_1$ agonist. Administration of exogenous $CB_1$ agonists may produce a range of responses, including reduced nociception, catalepsy, hypothermia, and increased feeding behavior. These four in particular are termed the "cannabinoid tetrad." Experiments with FAAH −/− mice show reduced responses in tests of nociception, but did not show catalepsy, hypothermia, or increased feeding behavior (Cravatt, *Proc. Natl. Acad. Sci. USA* 2001, 98(16), 9371). Fasting caused levels of AEA to increase in rat limbic forebrain, but not in other brain areas, providing evidence that stimulation of AEA biosynthesis may be anatomically regionalized to targeted CNS pathways (Kirkham, *Br. J. Pharmacol.* 2002, 136, 550). The finding that AEA increases are localized within the brain, rather than systemic, suggests that FAAH inhibition with a small molecule could enhance the actions of AEA and other fatty acid amides in tissue regions where synthesis and release of these signaling molecules is occurring in a given pathophysiological condition (Piomelli, 2003, supra).

In addition to the effects of a FAAH inhibitor on AEA and other endocannabinoids, inhibitors of FAAH's catabolism of other lipid mediators may be used in treating certain other therapeutic indications. For example, PEA has demonstrated biological effects in animal models of inflammation (Holt, et al. *Br. J. Pharmacol.* 2005, 146, 467-476), immunosuppression, analgesia, and neuroprotection (Ueda, *J. Biol. Chem.* 2001, 276(38), 35552). Oleamide, another substrate of FAAH, induces sleep (Boger, *Proc. Natl. Acad. Sci. USA* 2000, 97(10), 5044; Mendelson, *Neuropsychopharmacology* 2001, 25, S36). Inhibition of FAAH has also been implicated in cognition (Varvel et al., *J. Pharmacol. Exp. Ther.* 2006, 317(1), 251-257) and depression (Gobbi et al., *Proc. Natl. Acad. Sci. USA* 2005, 102(51), 18620-18625).

Two additional indications for FAAH are supported by recent data indicating that FAAH substrate activated receptors are important in energy metabolism, and in bone homeostasis (Overton et al., *Br. J. Pharmacol.* 2008, in press; and Plutzky, *Diab. Vasc. Dis. Res.* 2007, 4 Suppl 3, S12-4). It has been shown that the previously mentioned lipid signaling fatty acid amides catabolized by FAAH, oleoylethanolamide (OEA), is one of the most active agonists of the recently de-orphanised GPCR 119 (GPR119) (also termed glucose dependent insulinotropic receptor). This receptor is expressed predominantly in the pancreas in humans and activation improves glucose homeostasis via glucose-dependent insulin release in pancreatic beta-cells. GPR119 agonists can suppress glucose excursions when administered during oral glucose tolerance tests, and OEA has also been shown independently to regulate food intake and body weight gain when administered to rodents, indicating a probable benefit in energy metabolism disorders, such as insulin resistance and diabetes. The FAAH substrate palmitoylethanolamide (PEA) is an agonist at the PPARα receptor. Evidence from surrogate markers in human studies with the PPARα agonist fenofibrate is supportive of the concept that PPARα agonism offers the potential for inducing a coordinated PPARα response that may improve dyslipidaemia, repress inflammation and limit atherosclerosis in patients with the metabolic syndrome or type 2 diabetes. The FAAH substrate anandamide (AEA) is an agonist at the PPARγ receptor. Anandamide treatment induces 3T3-L1 differentiation into adipocytes, as well as triglyceride droplet accumulation and expression of adiponectin (Bouaboula et al., E. *J. Pharmacol.* 2005, 517, 174-181). Low dose cannabinoid therapy has been shown to reduce atherosclerosis in mice, further suggesting a therapeutic benefit of FAAH inhibition in dyslipidemia, liver steatosis, steatohepatitis, obesity, and metabolic syndrome (Steffens et al., *Nature,* 2005, 434, 782-6).

Osteoporosis is one of the most common degenerative diseases. It is characterized by reduced bone mineral density (BMD) with an increased risk for bone fractures. $CB_2$-deficient mice have a markedly accelerated age-related trabecular bone loss and cortical expansion. A $CB_2$-selective agonism enhances endocortical osteoblast number and activity and restrains trabecular osteoclastogenesis and attenuates ovariectomy-induced bone loss (Ofek et al., *Proc. Natl. Acad. Sci. U.S.A.* 2006, 103, 696-701). There is a substantial genetic contribution to BMD, although the genetic factors involved in the pathogenesis of human osteoporosis are largely unknown. The applicability to human BMD is suggested by genetic studies in which a significant association of single polymorphisms and haplotypes was found encompassing the CNR2 gene on human chromosome 1p36, demonstrating a role for the peripherally expressed $CB_2$ receptor in the etiology of osteoporosis (Karsak et al., *Hum. Mol. Genet,* 2005, 14, 3389-96).

Thus, small-molecule FAAH inhibitors should be useful in treating pain of various etiologies, anxiety, multiple sclerosis and other movement disorders, nausea/emesis, eating disorders, epilepsy, glaucoma, inflammation, immunosuppression, neuroprotection, depression, cognition enhancement, and sleep disorders, and potentially with fewer side effects than treatment with an exogenous cannabinoid.

A number of heteroaryl-substituted ureas have been reported in various publications. Certain substituted thiophene ureas are described in U.S. Pat. No. 6,881,741. Certain ureido-pyrazoles are described in U.S. Pat. No. 6,387,900. Certain benzothiazole amide derivatives are described in US Patent Publication US 2003/149036. Certain ureas are reported as prenyltransferase inhibitors in WO 2003/047569. Piperidinyl ureas are described as histamine $H_3$ receptor antagonists in U.S. Pat. No. 6,100,279. Piperazinyl ureas are disclosed as calcitonin mimetics in U.S. Pat. Nos. 6,124,299 and 6,395,740. Certain piperidinyl ureas and piperazinyl ureas have been previously described as FAAH modulators in U.S. patent application Ser. No. 12/126,389, filed May 23, 2008. Various ureas are reported as small-molecule FAAH modulators in US Patent Publication Nos. US 2006/173184 and US 2007/0004741, in Intl. Patent Appl. Nos. WO 2008/023720, WO 2008/047229, and WO 2008/024139, and by Cravatt et al. (Biochemistry 2007, 46(45), 13019. Ureas are described as modulators of other targets in U.S. Pat. Appl. Publ. US 2007/270433, and in Intl. Pat. Appl. Publ. Nos. WO 2007/096251 and WO 2006/085108.

However, there remains a desire for potent FAAH modulators with suitable pharmaceutical properties.

SUMMARY OF THE INVENTION

Certain aryl-substituted heterocyclic urea derivatives have been found to have FAAH-modulating activity. Thus, the invention is directed to the general and preferred embodiments defined, respectively, and by the independent and dependent claims appended hereto, which are incorporated by reference herein.

In one general aspect, the invention is directed to compounds of Formula (I):

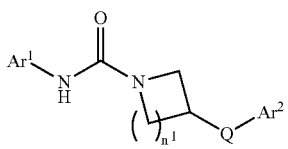

wherein
Q is —(CH$_2$)$_{1-3}$—, —(CH$_2$)$_{1-2}$O—, or —(CH$_2$)$_{1-2}$OCH$_2$—;
n$^1$ is 1 or 2, with the proviso that when n$^1$ is 1, then Q cannot be —CH$_2$—;
Ar$^1$ is a ring system selected from benzo[d]isoxazolyl, 1H-pyrrolo[2,3-b]pyridinyl, 2,1,3-benzoxadiazolyl, imidazo[1,2-a]pyridinyl, imidazo[1,2-b]pyridazinyl, isoquinolinyl, and pyridyl optionally substituted with triazolyl;
wherein each ring system is optionally substituted with halo;
Ar$^2$ is:
  (i) phenyl optionally substituted with one or two R$^d$ moieties; wherein each R$^d$ moiety is independently selected from —C$_{1-4}$alkyl, —OC$_{1-4}$alkyl, halo, —CF$_3$, —OCF$_3$, and —S(O)(O)C$_{1-4}$alkyl, or two adjacent R$^d$ moieties taken together form —OCH$_2$O— or —OCF$_2$O—;
  (ii) phenyl substituted at the 3- or 4-position with -L-Ar$^3$, said phenyl optionally substituted with one additional R$^d$ moiety, wherein:
    L is —O—(CH$_2$)$_{0-1}$— or a covalent bond;
    Ar$^3$ is:
      (a) phenyl optionally substituted with one or two R$^d$ moieties; or
      (b) pyridyl optionally substituted with one or two R$^d$ moieties;
  (iii) naphthyl;
  (iv) 5,6,7,8-tetrahydro-naphthalenyl; or
  (v) quinolinyl optionally substituted with a halo.

The invention also relates to pharmaceutically acceptable salts of compounds of Formula (I), pharmaceutically acceptable prodrugs of compounds of Formula (I), and pharmaceutically acceptable metabolites of compounds of Formula (I). In certain preferred embodiments, the compound of Formula (I) is a compound selected from those species described or exemplified in the detailed description below.

In a further general aspect, the invention relates to pharmaceutical compositions each comprising: (a) a therapeutically effective amount of at least one chemical entity selected from compounds of Formula (I), pharmaceutically acceptable salts of compounds of Formula (I), pharmaceutically acceptable prodrugs of compounds of Formula (I), and pharmaceutically acceptable metabolites of compounds of Formula (I); and (b) a pharmaceutically acceptable excipient.

In another aspect, embodiments of the invention are useful as FAAH modulators. Thus, the invention is directed to a method for modulating FAAH activity, comprising exposing FAAH to a therapeutically effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I). Embodiments of this invention modulate FAAH activity.

In another general aspect, the invention is directed to a method of treating a subject suffering from or diagnosed with a disease, disorder, or medical condition (collectively, "indications") mediated by FAAH activity, comprising administering to the subject in need of such treatment a therapeutically effective amount of a compound of Formula (I), a pharmaceutically acceptable salt of a compound of Formula (I), a pharmaceutically acceptable salt of a compound of Formula (I), and pharmaceutically acceptable prodrug, or a pharmaceutically active metabolite of a compound of Formula (I). In preferred embodiments of the inventive method, the disease, disorder, or medical condition is selected from: anxiety, depression, pain, sleep disorders, eating disorders, inflammation, multiple sclerosis and other movement disorders, HIV wasting syndrome, closed head injury, stroke, learning and memory disorders, Alzheimer's disease, epilepsy, Tourette's syndrome, Niemann-Pick disease, Parkinson's disease, Huntington's chorea, optic neuritis, autoimmune uveitis, symptoms of drug or alcohol withdrawal, nausea, emesis, sexual dysfunction, post-traumatic stress disorder, cerebral vasospasm, glaucoma, irritable bowel syndrome, inflammatory bowel disease, immunosuppression, itch, gastroesophageal reflux disease, paralytic ileus, secretory diarrhea, gastric ulcer, rheumatoid arthritis, unwanted pregnancy, hypertension, cancer, hepatitis, allergic airway disease, auto-immune diabetes, intractable pruritis, neuroinflammation, diabetes, metabolic syndrome, and osteoporosis.

Additional embodiments, features, and advantages of the invention will be apparent from the following detailed description and through practice of the invention.

DETAILED DESCRIPTION OF INVENTION AND ITS PREFERRED EMBODIMENTS

The invention may be more fully appreciated by reference to the following detailed description, including the following glossary of terms and the concluding examples. For the sake of brevity, the disclosures of the publications, including patents, cited in this specification are herein incorporated by reference.

As used herein, the terms "including", "containing" and "comprising" are used in their open, non-limiting sense.

The term "alkyl" refers to a straight- or branched-chain alkyl group having from 1 to 12 carbon atoms in the chain. Such groups may contain saturated or unsaturated carbon atoms within the chain. Examples of alkyl groups include methyl (Me, which also may be structurally depicted by/symbol), ethyl (Et), n-propyl, isopropyl, butyl, isobutyl, sec-butyl, tert-butyl (tBu), pentyl, isopentyl, tert-pentyl, hexyl, isohexyl, prop-2-enyl, prop-2-ynyl, and groups that in light of the ordinary skill in the art and the teachings provided herein would be considered equivalent to any one of the foregoing examples.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

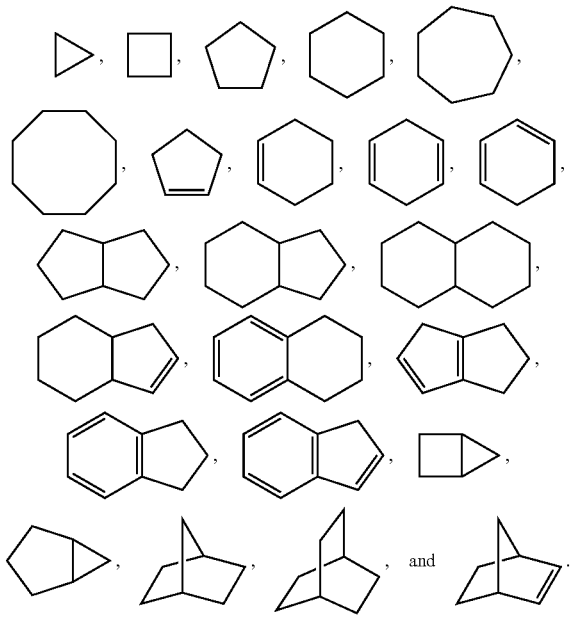

A "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative examples of heterocycloalkyl groups include the following entities, in the form of properly bonded moieties:

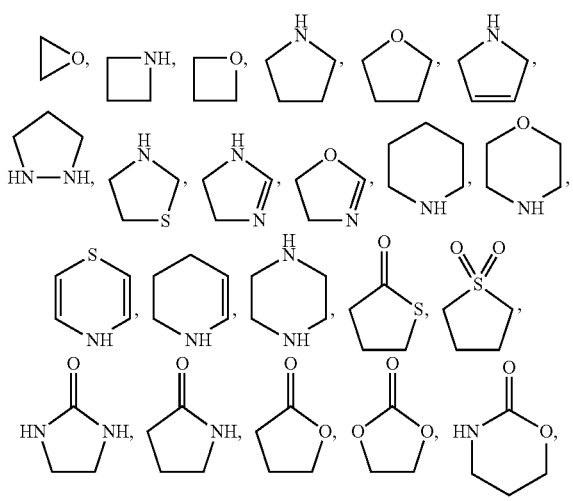

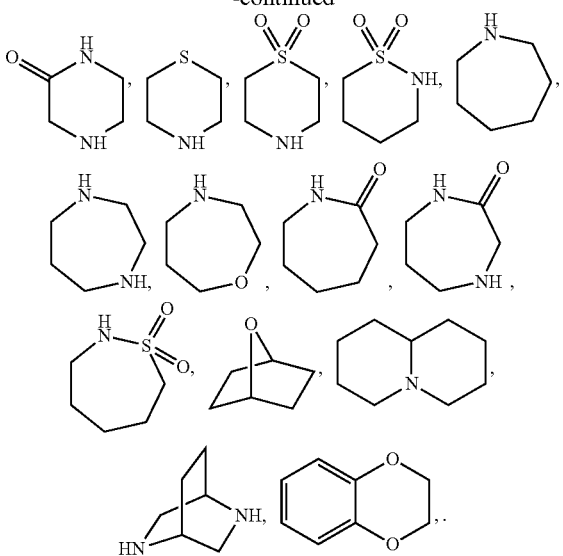

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

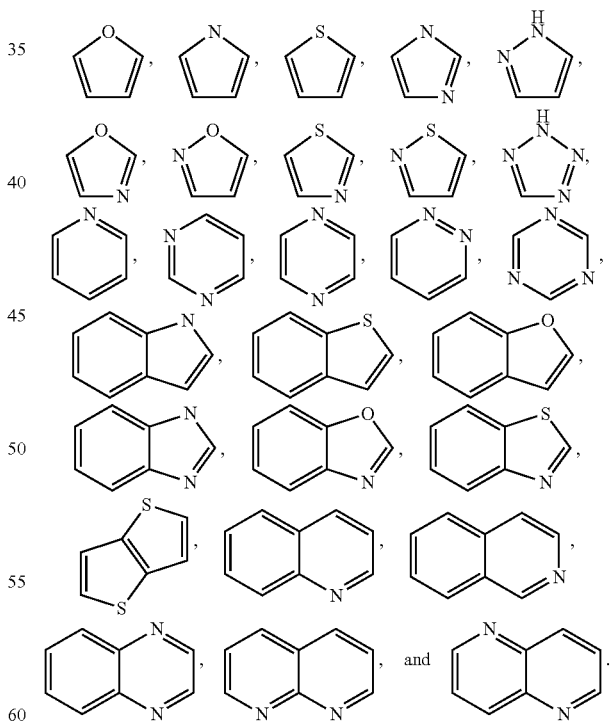

Those skilled in the art will recognize that the species of heteroaryl, cycloalkyl, and heterocycloalkyl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

A structural formula given herein is intended to represent compounds having structures depicted by the formula as well as equivalent variations or forms. For example, compounds encompassed by Formula (I) may have asymmetric centers and therefore exist in different enantiomeric forms. All optical isomers and stereoisomers of the compounds of the general formula, and mixtures thereof, are considered within the scope of the formula. Thus, a general formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers (e.g. pyrazole, benzimidazole, tetrazole, or benzotriazole tautomers), or as atropisomers, which are intended to be represented by the structural formula. Additionally, a formula given herein is intended to embrace hydrates, solvates, and polymorphs of such compounds, and mixtures thereof, even if such forms are not listed explicitly.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Reference to a chemical entity herein stands for a reference to any one of: (a) the actually recited form of such chemical entity, and (b) any of the forms of such chemical entity in the medium in which the compound is being considered when named. For example, reference herein to a compound such as R—COOH, encompasses reference to any one of, for example, R—COOH(s), R—COOH(sol), and R—COO-(sol). In this example, R—COOH(s) refers to the solid compound, as it could be for example in a tablet or some other solid pharmaceutical composition or preparation; R—COOH (sol) refers to the undissociated form of the compound in a solvent; and R—COO-(sol) refers to the dissociated form of the compound in a solvent, such as the dissociated form of the compound in an aqueous environment, whether such dissociated form derives from R—COOH, from a salt thereof, or from any other entity that yields R—COO— upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In this regard, if such entity is for example in an aqueous environment, it is understood that the compound R—COOH is in such same medium, and therefore the entity is being exposed to species such as R—COOH(aq) and/or R—COO-(aq), where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

Any structural formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$O, $^{17}$O, $^{32}$P, $^{33}$P, $^{35}$S, $^{18}$F, $^{36}$Cl, and $^{125}$I, respectively. Such isotopically labeled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT), including drug or substrate tissue distribution assays, or in radioactive treatment of patients. In particular, an $^{18}$F- or $^{11}$C-labeled compound may be preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the moiety for the variable appearing elsewhere. In other words, where a formula variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

In some embodiments of Formula (I), Ar¹ is a ring system selected from benzo[d]isoxazol-3-yl, 2,1,3-benzoxadiazol-4-yl, 4-chloropyridin-3-yl, imidazo[1,2-a]pyridin-3-yl, imidazo[1,2-a]pyridin-5-yl, imidazo[1,2-a]pyridin-6-yl, imidazo[1,2-b]pyridazin-3-yl, pyridin-3-yl, 6-[1,2,3]triazol-2-yl-pyridin-3-yl,

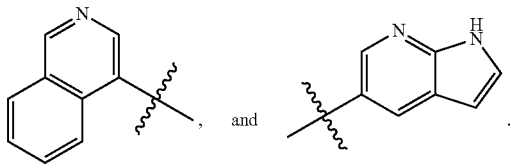 [SMILES: *c1cncc2ccccc12 ; *c1cnc2[nH]ccc2c1]

In some embodiments of Formula (I), Q is —CH₂CH₂O—. In further embodiments, Q is —CH₂O—.

In some embodiments of Formula (I), Ar² is phenyl substituted at the 3- or 4-position with -L-Ar³. In further embodiments, Ar² is phenyl substituted at the 3- or 4-position with -L-Ar³, L is —O—, and Ar³ is phenyl optionally substituted with one or two $R^d$ moieties. In other embodiments, Ar² is phenyl substituted at the 3- or 4-position with -L-Ar³, L is —O—, and Ar³ is pyridyl optionally substituted with one or two $R^d$ moieties. In further embodiments, Ar² is phenyl substituted at the 3- or 4-position with -L-Ar³ and Q is —CH₂CH₂O—. In further embodiments, Ar² is phenyl substituted at the 3- or 4-position with -L-Ar³ and Q is —CH₂O—.

In some embodiments of Formula (I), Ar² is phenyl optionally substituted with one or two $R^d$. In further embodiments, Ar² is phenyl optionally substituted with one or two $R^d$ and Q is —CH₂CH₂O—.

In some embodiments of Formula (I), n is 1. In further embodiments, n is 1 and Ar¹ is pyridin-3-yl optionally substituted with halo. In further embodiments, n is 1, Ar¹ is pyridin-3-yl optionally substituted with halo, and Ar² is phenyl substituted at the 3- or 4-position with -L-Ar³. In further embodiments, n is 1, Ar¹ is pyridin-3-yl optionally substituted with halo, Ar² is phenyl substituted at the 3- or 4-position with -L-Ar³, and Q is —CH₂CH₂O—. In further embodiments, n is 1, Ar¹ is pyridin-3-yl optionally substituted with halo, and Ar² is phenyl optionally substituted with one or two $R^d$.

In some embodiments of Formula (I), n is 2. In further embodiments, n is 2 and Ar¹ is pyridin-3-yl optionally substituted with halo. In further embodiments, n is 2, Ar¹ is pyridin-3-yl optionally substituted with halo, and Ar² is phenyl substituted at the 3- or 4-position with -L-Ar³. In further embodiments, n is 2, Ar¹ is pyridin-3-yl optionally substituted with halo, Ar² is phenyl substituted at the 3- or 4-position with -L-Ar³, and Q is —CH₂CH₂O—. In further embodiments, n is 2, Ar¹ is pyridin-3-yl optionally substituted with halo, and Ar² is phenyl optionally substituted with one or two $R^d$.

The invention includes also pharmaceutically acceptable salts of the compounds represented by Formula (I), preferably of those described below and of the specific compounds exemplified herein, and methods using such salts.

A "pharmaceutically acceptable salt" is intended to mean a salt of a free acid or base of a compound represented by Formula (I) that is non-toxic, biologically tolerable, or otherwise biologically suitable for administration to the subject. See, generally, S. M. Berge, et al., "Pharmaceutical Salts", J. Pharm. Sci., 1977, 66:1-19, and Handbook of Pharmaceutical Salts, Properties, Selection, and Use, Stahl and Wermuth, Eds., Wiley-VCH and VHCA, Zurich, 2002.

Preferred pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

If the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

If the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Examples of prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$ alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., Adv. Drug Delivery Rev. 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., J. Med. Chem. 1996, 39, 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of compounds of Formula (I), and uses of such metabolites in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini et al., J. Med. Chem. 1997, 40, 2011-2016; Shan et al., J. Pharm. Sci. 1997, 86 (7), 765-767; Bagshawe, Drug Dev. Res. 1995, 34, 220-230; Bodor, Adv. Drug Res. 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

The compounds of Formula (I), and their pharmaceutically acceptable salts, pharmaceutically acceptable prodrugs, and pharmaceutically active metabolites (collectively, "active agents") of the present invention are useful as FAAH inhibitors in the methods of the invention. The active agents may be used in the inventive methods for the treatment of medical conditions, diseases, or disorders mediated through inhibition or modulation of FAAH, such as those described herein. Active agents according to the invention may therefore be used as an analgesic, anti-depressant, cognition enhancer, neuroprotectant, sedative, appetite stimulant, or contraceptive.

Thus, the active agents may be used to treat subjects diagnosed with or suffering from a disease, disorder, or condition mediated through FAAH activity. The term "treat" or "treating" as used herein is intended to refer to administration of an active agent or composition of the invention to a subject for the purpose of effecting a therapeutic or prophylactic benefit through modulation of FAAH activity. Treating includes reversing, ameliorating, alleviating, inhibiting the progress of, lessening the severity of, or preventing a disease, disorder, or condition, or one or more symptoms of such disease, disorder or condition mediated through modulation of FAAH activity. The term "subject" refers to a mammalian patient in need of such treatment, such as a human. "Modulators" include both inhibitors and activators, where "inhibitors" refer to compounds that decrease, prevent, inactivate, desensitize or down-regulate FAAH expression or activity, and "activators" are compounds that increase, activate, facilitate, sensitize, or up-regulate FAAH expression or activity.

Accordingly, the invention relates to methods of using the active agents described herein to treat subjects diagnosed with or suffering from a disease, disorder, or condition mediated through FAAH activity, such as: anxiety, pain, sleep disorders, eating disorders, inflammation, movement disorders (e.g., multiple sclerosis), energy metabolism (e.g. insulin resistance, diabetes, dyslipidemia, liver steatosis, steatohepatitis, obesity, and metabolic syndrome) and bone homeostasis (e.g. osteoporosis).

In certain preferred embodiments, active agents may be used in methods to treat a FAAH mediated disease, disorder, or medical condition where the disease, disorder, or medical condition is selected from the group consisting of anxiety, depression, pain, sleep disorders, eating disorders, inflammation, multiple sclerosis and other movement disorders, HIV wasting syndrome, closed head injury, stroke, learning and memory disorders, Alzheimer's disease, epilepsy, Tourette's syndrome, epilepsy, Niemann-Pick disease, Parkinson's disease, Huntington's chorea, optic neuritis, autoimmune uveitis, symptoms of drug withdrawal, nausea, emesis, sexual dysfunction, post-traumatic stress disorder, cerebral vasospasm, glaucoma, irritable bowel syndrome, inflammatory bowel disease, immunosuppression, gastroesophageal reflux disease, paralytic ileus, secretory diarrhea, gastric ulcer, rheumatoid arthritis, unwanted pregnancy, hypertension, cancer, hepatitis, allergic airway disease, autoimmune diabetes, intractable pruritis, neuroinflammation, diabetes, metabolic syndrome and osteoporosis. In certain preferred embodiments, the disease, disorder, or medical condition is pain or inflammation. In further embodiments, the disease, disorder, or medical condition is anxiety, a sleep disorder, an eating disorder, or a movement disorder. In further embodiments, the disease, disorder, or medical condition is multiple sclerosis. In further embodiments, the disease, disorder, or medical condition is energy metabolism or bone homeostasis.

Symptoms or disease states are intended to be included within the scope of "medical conditions, disorders, or diseases." For example, pain may be associated with various diseases, disorders, or conditions, and may include various etiologies. Illustrative types of pain treatable with a FAAH-modulating agent, in one example herein a FAAH-inhibiting agent, according to the invention include cancer pain, postoperative pain, GI tract pain, spinal cord injury pain, visceral hyperalgesia, thalamic pain, headache (including stress headache and migraine), low back pain, neck pain, musculoskeletal pain, peripheral neuropathic pain, central neuropathic pain, neurogenerative disorder related pain, and menstrual pain. HIV wasting syndrome includes associated symptoms such as appetite loss and nausea. Parkinson's disease includes, for example, levodopa-induced dyskinesia. Treatment of multiple sclerosis may include treatment of symptoms such as spasticity, neurogenic pain, central pain, or bladder dysfunction. Symptoms of drug withdrawal may be caused by, for example, addiction to opiates or nicotine. Nausea or emesis may be due to chemotherapy, postoperative, or opioid related causes. Treatment of sexual dysfunction may include improving libido or delaying ejaculation. Treatment of cancer may include treatment of glioma. Sleep disorders include, for example, sleep apnea, insomnia, and disorders calling for treatment with an agent having a sedative or narcotic-type effect. Eating disorders include, for example, anorexia or appetite loss associated with a disease such as cancer or HIV infection/AIDS.

In treatment methods according to the invention, an effective amount of at least one active agent according to the invention is administered to a subject suffering from or diagnosed as having such a disease, disorder, or condition. A "therapeutically effective amount" or "effective amount" means an amount or dose of a FAAH-modulating agent sufficient to generally bring about a therapeutic benefit in patients in need of treatment for a disease, disorder, or condition mediated by FAAH activity. Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. An exemplary dose is in the range of from about 0.0001 to about 200 mg of active agent per kg of subject's body weight per day, preferably about 0.001 to 100 mg/kg/day, or about 0.01 to 35 mg/kg/day, or about 0.1 to 10 mg/kg daily in single or divided dosage units (e.g., BID, TID, QID). For a 70-kg human, an illustrative range for a suitable dosage amount is from about 0.05 to about 7 g/day, or about 0.2 to about 5 g/day. Once improvement of the patient's disease, disorder, or condition has occurred, the dose may be adjusted for maintenance treatment. For example, the dosage or the frequency of administration, or both, may be reduced as a function of the symptoms, to a level at which the desired therapeutic effect is maintained. Of course, if symptoms have been alleviated to an appropriate level, treatment may cease. Patients may, however, require intermittent treatment on a long-term basis upon any recurrence of symptoms.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be coadministered separately with an active agent of Formula (I) or included with such an agent in a pharmaceutical composition according to the invention. In an exemplary embodiment, additional active ingredients are those that are known or discovered to be effective in the treatment of conditions, disorders, or diseases mediated by FAAH activity, such as another FAAH modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention. In one illustrative embodiment, a composition according to the invention may contain one or more additional active ingredients selected from opioids, non-steroidal anti-inflammatory drugs (NSAIDs) (e.g., ibuprofen, cyclooxygenase-2 (COX-2) inhibitors, and naproxen), gabapentin, pregabalin, tramadol, acetaminophen, and aspirin.

The active agents of the invention are used, alone or in combination with one or more additional active ingredients, to formulate pharmaceutical compositions of the invention. A pharmaceutical composition of the invention comprises: (a) an effective amount of at least one active agent in accordance with the invention; and (b) a pharmaceutically acceptable excipient.

When referring to modulating the target receptor, an "effective amount" means an amount sufficient to affect the activity of such receptor. Measuring the activity of the target receptor may be performed by routine analytical methods. Target receptor modulation is useful in a variety of settings, including assays.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the active agents of the invention can be provided in the form of tablets or capsules, or as a solution, emulsion, or suspension. To prepare the oral compositions, the active agents may be formulated to yield a dosage of, e.g., from about 5 mg to 5 g daily, or from about 50 mg to 5 g daily, in single or divided doses. For example, a total daily dosage of about 5 mg to 5 g daily may be accomplished by dosing once, twice, three, or four times per day.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 μg/kg/minute of agent admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Active agents may alternatively be administered in methods of this invention by inhalation, via the nasal or oral routes, e.g., in a spray formulation also containing a suitable carrier.

Exemplary active agents useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I).

SCHEME A

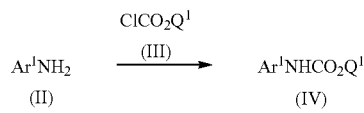

Referring to Scheme A, a carbamate of formula (IV) may be obtained by reacting a compound of formula (II) with a compound of formula (III), in which $Q^1$ represents a substituted or unsubstituted phenyl group, in a solvent such as dimethylformamide, acetonitrile or tetrahydrofuran, with or without a base such as pyridine, triethylamine, or diisopropylethylamine, at a temperature from about 0° C. to about 80° C. Preferably, $Q^1$ is phenyl, and the reaction occurs with or without a base such as pyridine, in acetonitrile, at room temperature. In certain embodiments, the reaction occurs with 1.0 equivalent of a compound of formula (III) in the presence of 1.0 to 1.5 equivalents of base and 1.0 equivalent of a compound of formula (II). In other embodiments, the reaction occurs with 0.5 equivalent of a compound of formula (III) and 1.0 equivalent of a compound of formula (II) in the absence of base.

SCHEME B

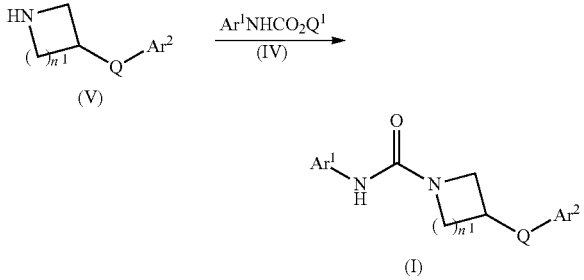

Referring to Scheme B, a compound of formula (I) is obtained by reacting a compound of Formula (V) with a compound of formula (IV) in a solvent such as dimethylformamide or acetonitrile at a temperature from about rt to about 120° C. Preferably, $Q^1$ is phenyl, and the reaction is performed in acetonitrile with heating from about rt to about 50° C.

SCHEME C

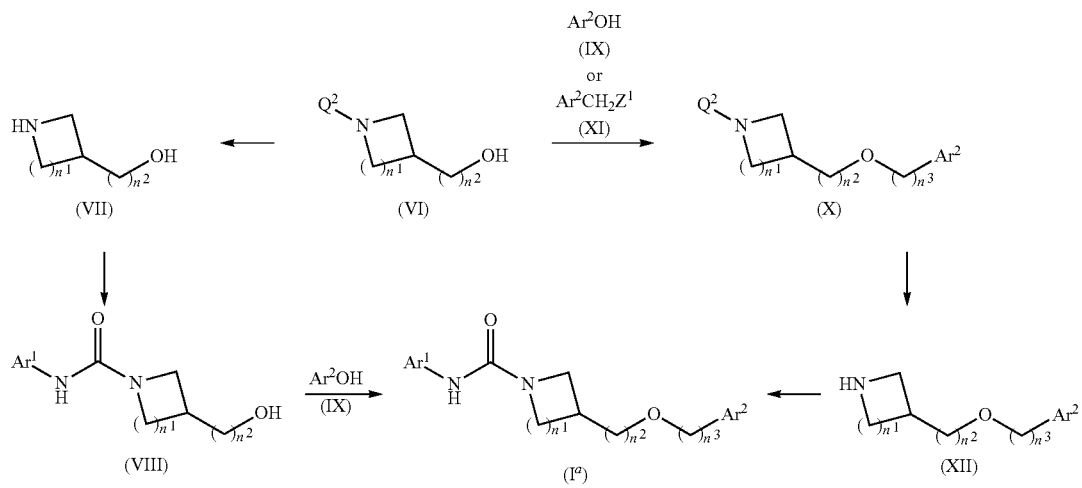

Referring to Scheme C, compounds of formula (I$^a$) where n$^2$ is 1 or 2 and n$^3$ is 0 or 1 are prepared from compounds of formula (VI). One skilled in the art would recognize that compounds of Formula (I$^a$) represent a subset of compounds of formula (I). Substituent Q$^2$ is a suitable amino protecting group compatible with the transformations in Scheme C. Preferably, Q$^2$ is tert-butyloxycarbonyl (BOC). An amine of formula (VII) is obtained by deprotecting a compound of formula (VI) under suitable Q$^2$ deprotection conditions. When Q$^2$ is BOC, removal may be preferably affected with HCl, trifluoroacetic acid (TFA) or formic acid in a solvent such as diethyl ether (Et$_2$O), DCM, or 1,4-dioxane. Alternatively, BOC removal may be effected in neat TFA or formic acid. A compound of formula (VIII) is obtained by reacting a compound of formula (VII) with a compound of formula (IV).

Compounds of formula (VIII) are reacted with an alcohol of formula (IX) under Mitsunobu reaction conditions in a solvent such as tetrahydrofuran (THF), 1,2-dichloroethane (DCE), DCM, or Et$_2$O at a temperature from about 0° C. to 80° C. to produce a compound of Formula (I$^a$), where n$^3$ is 0. In preferred embodiments, diisopropyl azodicarboxylate and polymer supported triphenyl phosphine in THF is employed at rt.

In alternative embodiments, compounds of formula (X), where n$^3$ is 0, are obtained by reacting a compound of formula (VI) with a phenol of formula (IX) under Mitsunobu reaction conditions in a solvent such as tetrahydrofuran (THF), 1,2-dichloroethane (DCE), DCM, or Et$_2$O at a temperature from about 0° C. to 80° C. Preferably, diisopropyl azodicarboxylate and polymer supported triphenyl phosphine in THF is employed at rt. In alternative embodiments, compounds of formula (X), where n$^3$ is 1, are obtained by reacting a compound of formula (VI) with a benzylating agent of formula (XI), where Z$^1$ is I, Br, or Cl, under basic conditions in a solvent such as tetrahydrofuran (THF), dimethylformamide (DMF), or dimethylsulfoxide (DMSO) at a temperature from about 0° C. to 100° C. Preferably, sodium hydride and Ar$^2$CH$_2$Br in THF is employed at rt with tetrabutylammonium iodide as a catalyst. Deprotection of Q$^2$ from a compound of formula (X) under general deprotection conditions provides compounds of formula (XII). Where Q$^2$ is BOC, deprotection was achieved following the steps previously described above. Compounds of formula (I$^a$) are obtained by reacting a compound of formula (XII) with either a compound of formula (IV) or with a compound Ar$^1$NH$_2$ in the presence of di-(N-succinimidyl) carbonate.

Scheme D

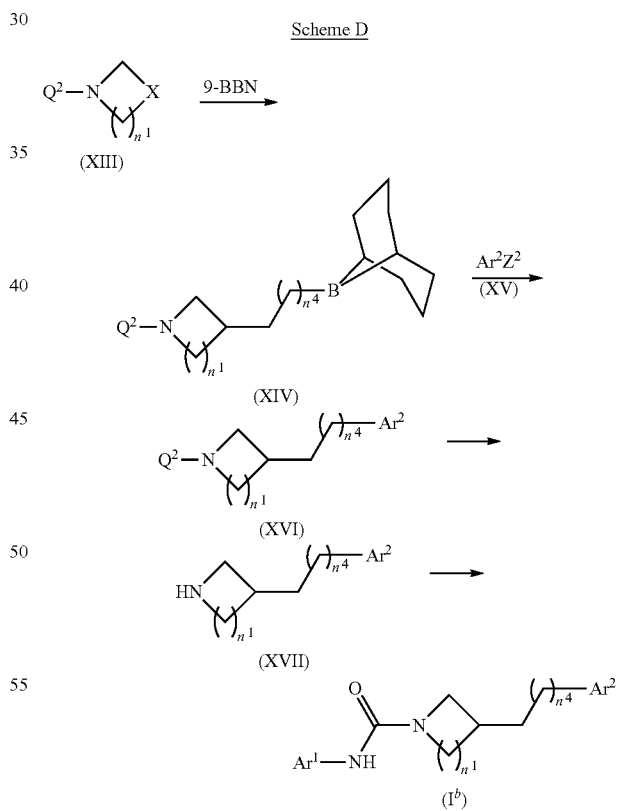

Referring to Scheme D, compounds of formula (I$^b$), where n$^1$ is 1 or 2 and n$^4$ is 0 or 1, are prepared from compounds of formula (XIII), where X is >C=CH$_2$ or >CHCH=CH$_2$ utilizing a suitable protecting group Q$^2$ compatible with subsequent transformations. One skilled in the art would recognize that compounds of Formula (I$^b$) represent a subset of compounds of formula (I). In preferred embodiments $Q^2$ is BOC. A compound of formula (XIV) is obtained by reacting a compound of formula (XIII) under hydroboration conditions, preferably using 9-borabicyclo[3.3.1]nonane as the borylating agent in a solvent such as THF at a temperature from about rt to about 80° C. Compounds of formula (XVI) are obtained via palladium-mediated cross-coupling with reagents of formula (XV), where $Z^2$ is Br or I, with boronic esters of formula (XIV). In certain embodiments, boronic esters of formula (XIV) are treated with compounds of formula (XV) in the presence of a base such as $K_3PO_4$, $K_2CO_3$, or KF in a suitable polar solvent such as $CH_3CN$, 1,2-dimethoxyethane (DME), tetrahydrofuran (THF), water, or a mixture thereof, at a temperature from about 50° C. to about 180° C. using conventional heating or a microwave reactor. An amine of formula (XVII) is obtained by deprotecting a compound of formula (XVI) with a reagent under suitable $Q^2$ deprotection conditions. When $Q^2$ is BOC, deprotection may be affected using the methods described previously in Scheme C. A compound of formula ($I^b$) is obtained by reacting a compound of formula (XVII) with a compound of formula (IV). In alternative embodiments, a compound of formula ($I^b$) is obtained by reacting a compound of formula (XVII) with a compound of formula $Ar^1NH_2$ in the presence of di-(N-succinimidyl)carbonate.

Compounds of formula (I) may be converted to their corresponding salts by applying general techniques described in the art. For example, a compound of formula (I) may be treated with trifluoroacetic acid, HCl, or citric acid in a solvent such as $Et_2O$, 1,4-dioxane, DCM, THF, or MeOH to provide the corresponding salt forms.

Compounds prepared according to the schemes described above may be obtained as single enantiomers, diastereomers, or regioisomers, by enantio-, diastero-, or regio-specific synthesis, or by resolution. Compounds prepared according to the schemes above may alternatively be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following specific examples are provided to further illustrate the invention and various preferred embodiments.

EXAMPLES

In preparing the examples listed below, the following general experimental and analytical methods were used.

Reaction mixtures were stirred under a nitrogen atmosphere at room temperature (rt) unless otherwise noted. Where solutions or mixtures are concentrated, they are typically concentrated under reduced pressure using a rotary evaporator. Where solutions are dried, they are typically dried over a drying agent such as $MgSO_4$ or $Na_2SO_4$, unless otherwise noted.

Microwave reactions were carried out in either a CEM Discover or a Biotage Initiator™ Microwave at specified temperatures.

Normal-phase flash column chromatography (FCC) was performed on pre-packed Isco silica gel columns using 2 N $NH_3$ in methanol/$CH_2Cl_2$ or EtOAc/hexanes as eluents.

Reversed-Phase High Performance Liquid Chromatography (HPLC) was performed using: Shimadzu instrument with a Phenomenex Gemini column 5 µm C18 (150×21.2 mm) or Waters Xterra RP18 OBD column 5 µm (100×30 mm), a gradient of 95:5 to 0:100 water (0.05% TFA)/$CH_3CN$ (0.05% TFA), a flow rate of 80 mL/min, and detection at 254 nM.

Mass spectra were obtained on an Agilent series 1100 MSD using electrospray ionization (ESI) in positive mode unless otherwise indicated.

NMR spectra were obtained on either a Bruker model DPX400 (400 MHz), DPX500 (500 MHz) or DRX600 (600 MHz) spectrometer. The format of the $^1$H NMR data below is: chemical shift in ppm down field of the tetramethylsilane reference (multiplicity, coupling constant J in Hz, integration).

Chemical names were generated using ChemDraw Ultra 6.0.2 (CambridgeSoft Corp., Cambridge, Mass.) or ACD/Name Version 9 (Advanced Chemistry Development, Toronto, Ontario, Canada).

Intermediate 1:
(6-[1,2,3]Triazol-2-yl-pyridin-3-yl)-carbamic acid phenyl ester

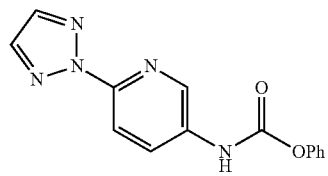 [SMILES: O=C(Nc1ccc(-n2nccn2)nc1)Oc1ccccc1]

To a solution consisting of 6-[1,2,3]triazol-2-yl-pyridin-3-ylamine (1.00 g, 6.21 mmol) in $CH_3CN$ (10 mL) was added phenyl chloroformate (0.389 mL, 3.10 mmol) dropwise at rt. After 16 h, the reaction mixture was diluted with EtOAc (30 mL) and washed with saturated aq. NaCl. The organic layer was separated, dried ($Na_2SO_4$), and concentrated. The crude residue was purified (FCC) to give the title compound as a white solid (0.808 g, 93%). MS (ESI$^+$): calcd. for $C_{14}H_{11}N_5O_2$, 281.09. m/z found, 282.1 (M+H)$^+$.

Intermediates 2 to 10 were prepared using methods analogous to those described for intermediate 1, using the appropriate starting material.

Intermediate 2: Benzo[d]isoxazol-3-yl-carbamic acid phenyl ester

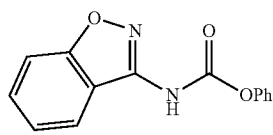 [SMILES: O=C(Nc1noc2ccccc12)Oc1ccccc1]

MS (ESI$^+$): calcd. for $C_{14}H_{10}N_2O_3$, 254.07. m/z found, 255.1 (M+H)$^+$.

Intermediate 3: Pyridin-3-yl-carbamic acid phenyl ester

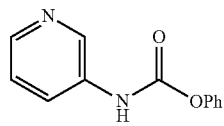 [SMILES: O=C(Nc1cccnc1)Oc1ccccc1]

MS (ESI$^+$): calcd. for $C_{12}H_{10}N_2O_2$, 214.07. m/z found, 215.1 (M+H)$^+$.

Intermediate 4: (1H-Pyrrolo[2,3-b]pyridin-5-yl)-carbamic acid phenyl ester

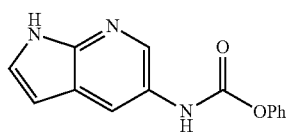 [SMILES: O=C(Nc1cnc2[nH]ccc2c1)Oc1ccccc1]

MS (ESI$^+$): calcd. for $C_{14}H_{11}N_3O_2$, 253.09. m/z found, 254.1 (M+H)$^+$.

Intermediate 5: Imidazo[1,2-b]pyridazin-3-yl-carbamic acid phenyl ester

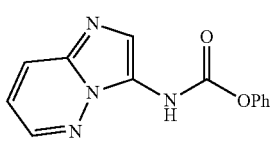 [SMILES: O=C(Nc1cnc2cccnn12)Oc1ccccc1]

MS (ESI$^+$): calcd. for $C_{13}H_{10}N_4O_2$, 254.08. m/z found, 255.1 (M+H)$^+$.

Intermediate 6: Imidazo[1,2-a]pyridin-3-yl-carbamic acid phenyl ester

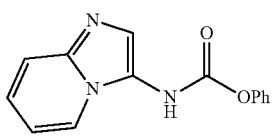 [SMILES: O=C(Nc1cnc2ccccn12)Oc1ccccc1]

MS (ESI$^+$): calcd. for $C_{14}H_{11}N_3O_2$, 253.09. m/z found, 254.1 (M+H)$^+$.

Intermediate 7: N-2,1,3-Benzoxadiazol-4-yl-carbamic acid phenyl ester

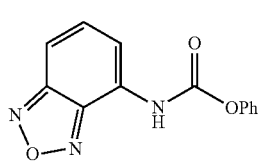 [SMILES: O=C(Nc1cccc2nonc12)Oc1ccccc1]

MS (ESI$^+$): calcd. for $C_{13}H_9N_3O_3$, 255.06. m/z found, 256.1 (M+H)$^+$.

Intermediate 8: (4-Chloro-pyridin-3-yl)-carbamic acid phenyl ester

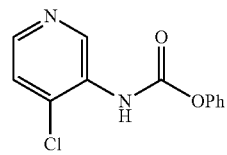 [SMILES: O=C(Nc1cnccc1Cl)Oc1ccccc1]

MS (ESI$^+$): calcd. for $C_{12}H_9ClN_2O_2$, 248.04. m/z found, 249.1 (M+H)$^+$.

Intermediate 9: Imidazo[1,2-a]pyridin-6-yl-carbamic acid phenyl ester

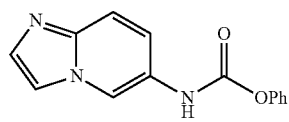 [SMILES: O=C(Nc1ccc2nccn2c1)Oc1ccccc1]

MS (ESI$^+$): calcd. for $C_{14}H_{11}N_3O_2$, 253.09. m/z found, 254.1 (M+H)$^+$.

Intermediate 10: Isoquinolin-4-yl-carbamic acid phenyl ester

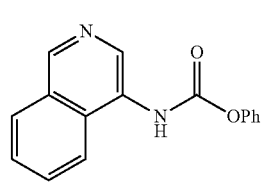 [SMILES: O=C(Nc1cncc2ccccc12)Oc1ccccc1]

MS (ESI$^+$): calcd. for $C_{16}H_{12}N_2O_2$, 264.09. found, 265.1 (M+H)$^+$.

Intermediate 11: 3-(2-Hydroxy-ethyl)-azetidine-1-carboxylic acid tert-butyl ester

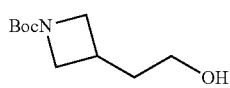 [SMILES: CC(C)(C)OC(=O)N1CC(CCO)C1]

A solution consisting of 3-carboxymethyl-azetidine-1-carboxylic acid tert-butyl ester (10.0 g, 46.5 mmol) and THF (15 mL) was cooled to 0° C. and treated with a 1 M solution of borane in THF (70 mL, 70 mmol), then slowly warmed to rt. After stirring for 18 h, the reaction mixture was quenched with 2 N NaOH (100 mL), diluted with H$_2$O (100 mL), and extracted with Et$_2$O (3×200 mL). The organic layers were combined, dried (MgSO$_4$), and concentrated to give the title compound as a colorless oil (9.03 g, 97%). MS (ESI$^+$): calcd. for $C_{10}H_{19}NO_3$, 201.14. m/z found, 224.2 (M+Na)$^+$. $^1$H NMR (d$_6$-DMSO): 4.37 (t, J=5.1 Hz, 1H), 3.95-3.79 (m, 2H), 3.53-3.43 (m, 2H), 3.37 (dd, J=11.5, 6.2 Hz, 2H), 2.62-2.52 (m, 1H), 1.66 (dd, J=13.8, 6.4 Hz, 2H), 1.39-1.33 (m, 9H).

Intermediate 12:
3-(5-Chloro-pyridin-2-yloxy)-phenol

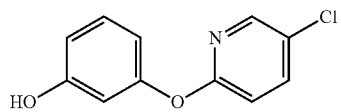

To a solution consisting of 5-chloro-2-fluoropyridine (1.3 mL, 13 mmol) and resorcinol (2.1 g, 19 mmol) and DMSO (30 mL) was added $Cs_2CO_3$ (6.3 g, 19 mmol). The reaction vessel was heated at 40° C. for 22 hours then diluted with $CH_2Cl_2$ (60 mL) and washed with saturated aq. $NH_4Cl$ (100 mL). The organic layer was dried ($MgSO_4$) and concentrated. The crude residue was purified (FCC) to give the title compound (1.0 g, 37%). MS ($ESI^+$): calcd. for $C_{11}H_8ClNO_2$, 221.02. m/z found, 222.1 (M+H)$^+$. $^1$H NMR (CDCl$_3$): 8.14 (d, J=2.6 Hz, 1H), 7.65 (dd, J=8.7, 2.7 Hz, 1H), 7.26-7.22 (m, 1H), 6.89 (dd, J=8.7, 0.5 Hz, 1H), 6.69-6.65 (m, 2H), 6.60 (t, J=2.3 Hz, 1H).

Intermediate 13: 3-(4-Chloro-phenoxy)-phenol

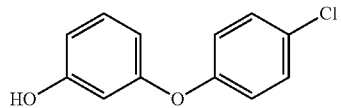 [SMILES: Oc1cccc(Oc2ccc(Cl)cc2)c1]

A suspension of resorcinol (12.58 g, 114.2 mmol), 4-bromochlorobenzene (10.94 g, 57.14 mmol), dimethylglycine HCl (2.39 g, 17.1 mmol), and cesium carbonate (37.2 g, 114 mmol) in DMA (80 mL) was treated with CuI (1.09 g, 5.71 mmol) and heated at 90° C. for 16 h. The reaction mixture was cooled to room temperature, diluted with ethyl acetate (500 mL) and extracted with 1 N NaOH (400 mL), and brine (200 mL). The organic layer was dried ($MgSO_4$) and concentrated. The residue was purified (FCC) to give the title compound as a yellow oil (7.6 g, 60%). MS ($ESI^+$): calcd. for $C_{12}H_9ClO_2$, 220.03. m/z found, 221.1 (M+H)$^+$. $^1$H NMR (d$_6$-DMSO): 9.63 (s, 1H), 7.43 (d, J=8.9 Hz, 2H), 7.17 (t, J=8.1 Hz, 1H), 7.03 (d, J=8.9 Hz, 2H), 6.58-6.54 (m, 1H), 6.46-6.41 (m, 1H), 6.38 (t, J=2.3 Hz, 1H).

Intermediates 14 to 15 were prepared using methods analogous to those described for intermediate 13, using the appropriate starting material.

Intermediate 14:
3-(4-Trifluoromethoxy-phenoxy)-phenol

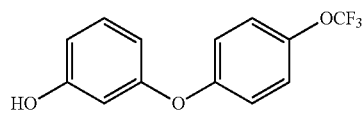 [SMILES: Oc1cccc(Oc2ccc(OC(F)(F)F)cc2)c1]

MS (ESI$^-$): calcd. for $C_{13}H_9F_3O_3$, 270.05. m/z found, 269.0 (M−H)$^-$.

Intermediate 15:
3-(4-Methanesulfonyl-phenoxy)-phenol

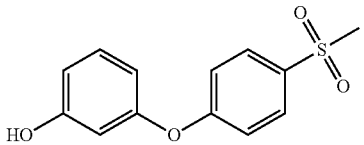 [SMILES: CS(=O)(=O)c1ccc(Oc2cccc(O)c2)cc1]

MS (ESI$^-$): calcd. for $C_{13}H_{12}O_4S$, 264.05. m/z found, 263.0 (M−H)$^-$.

Example 1

3-{2-[3-(4-Chloro-phenoxy)-phenoxy]-ethyl}-azetidine-1-carboxylic acid imidazo[1,2-b]pyridazin-3-ylamide

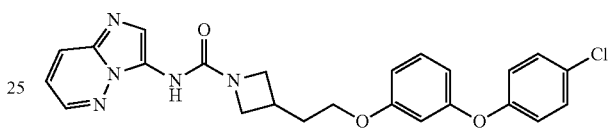

Step A: 3-{2-[3-(4-Chloro-phenoxy)-phenoxy]-ethyl}-azetidine-1-carboxylic acid tert-butyl ester A solution consisting of 3-(2-hydroxy-ethyl)-azetidine-1-carboxylic acid tert-butyl ester (4.39 g, 21.8 mmol), 3-(4-chloro-phenoxy)-phenol (4.81 g, 21.8 mmol) and THF (40 mL) was cooled at 0° C., treated with polymer supported triphenyl phosphine (10.9 g, 32.7 mmol) then diisopropyl azodicarboxylate (6.62 g, 32.7 mmol) dropwise over 30 min. After stirring for 15 min at 0° C., the reaction mixture was allowed to warm to room temperature and stirred for 16 h. The reaction mixture was filtered, the filtrate evaporated, and the residue purified (FCC) to give the title compound as a clear oil (6.39 g, 73%). MS (ESI$^+$): calcd. for $C_{22}H_{26}ClNO_4$, 403.16. m/z found, 426.2 (M+Na)$^+$. $^1$H NMR (d$_6$-DMSO): 7.43 (d, J=9.0 Hz, 2H), 7.28 (t, J=8.2 Hz, 1H), 7.03 (d, J=9.0 Hz, 2H), 6.72 (dd, J=8.3, 1.5 Hz, 1H), 6.59-6.55 (m, 2H), 3.98-3.84 (m, 4H), 3.59-3.50 (m, 2H), 2.70-2.58 (m, 1H), 2.02-1.89 (m, 2H), 1.36 (s, 9H).

Step B: 3-{2-[3-(4-Chloro-phenoxy)-phenoxy]-ethyl}-azetidine, formic acid salt

3-{2-[3-(4-Chloro-phenoxy)-phenoxy]-ethyl}-azetidine-1-carboxylic acid tert-butyl ester (545 mg, 1.35 mmol) was dissolved in formic acid (5.0 mL) and stirred for 4 h at room temperature. The formic acid was evaporated to provide the title compound as a yellow oil (460 mg, 100%). MS (ESI$^+$): calcd. for $C_{17}H_{18}ClNO_2$, 303.10. m/z found, 304.1 (M+H)$^+$. $^1$H NMR (d$_6$-DMSO): 8.41 (s, 1H), 7.43 (d, J=8.8 Hz, 2H), 7.28 (t, J=8.1 Hz, 1H), 7.03 (d, J=8.8 Hz, 2H), 6.72 (dd, J=8.2, 2.2 Hz, 1H), 6.60-6.53 (m, 2H), 3.94 (t, J=6.2 Hz, 2H), 3.88 (t, J=9.2 Hz, 2H), 3.67-3.59 (m, 2H), 2.95-2.85 (m, 1H), 2.03-1.96 (m, 2H).

Step C: 3-{2-[3-(4-Chloro-phenoxy)-phenoxy]-ethyl}-azetidine-1-carboxylic acid imidazo[1,2-b]pyridazin-3-ylamide To a solution consisting of 3-{2-[3-(4-chloro-phenoxy)-phenoxy]-ethyl}-azetidine formic acid salt (0.040 g, 0.13 mmol), TEA (0.018 mL, 0.13 mmol) and CH₃CN (1.0 mL) was added imidazo[1,2-b]pyridazin-3-yl-carbamic acid phenyl ester (0.034 g, 0.13 mmol). The reaction mixture was stirred at room temperature for 16 h, then diluted with EtOAc (40 mL) and washed with saturated aq. NaHCO₃ (40 mL). The organic layer was dried (Na₂SO₄) and concentrated. The crude residue was purified (FCC) to give the title compound (0.035 g, 57%). MS (ESI⁺): calcd. for C₂₄H₂₂ClN₅O₃, 463.14. m/z found, 464.1 (M+H)⁺. ¹H NMR (d₆-DMSO): 8.55 (s, 1H), 8.52 (d, J=4.4 Hz, 1H), 8.06 (d, J=9.2 Hz, 1H), 7.64 (s, 1H), 7.43 (d, J=7.3 Hz, 2H), 7.29 (t, J=8.2 Hz, 1H), 7.19-7.15 (m, 1H), 7.04 (d, J=7.4 Hz, 2H), 6.75 (d, J=8.3 Hz, 1H), 6.61-6.55 (m, 2H), 4.09 (t, J=8.1 Hz, 2H), 3.99 (t, J=6.1 Hz, 2H), 3.77-3.66 (m, 2H), 2.83-2.69 (m, 1H), 2.10-2.01 (m, 2H).

Examples 2 to 48 were prepared using methods analogous to those described for Example 1, using the appropriate carbamate and phenol.

Example 2

3-Phenoxymethyl-azetidine-1-carboxylic acid pyridin-3-ylamide, trifluoroacetate salt

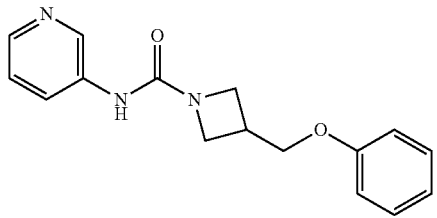 [SMILES: O=C(Nc1cccnc1)N1CC(COc2ccccc2)C1]

MS (ESI⁺): calcd. for C₁₆H₁₇N₃O₂, 283.13. m/z found, 284.2 (M+H)⁺. ¹H NMR (d₆-DMSO): 9.20 (s, 1H), 8.99 (d, J=2.3 Hz, 1H), 8.39 (dd, J=5.2, 1.0 Hz, 1H), 8.34-8.27 (m, 1H), 7.74 (dd, J=8.6, 5.3 Hz, 1H), 7.35-7.26 (m, 2H), 7.00-6.91 (m, 3H), 4.19-4.11 (m, 4H), 3.86 (dd, J=8.3, 5.5 Hz, 2H), 3.11-2.99 (m, 1H).

Example 3

3-(4-Bromo-phenoxymethyl)-azetidine-1-carboxylic acid pyridin-3-ylamide

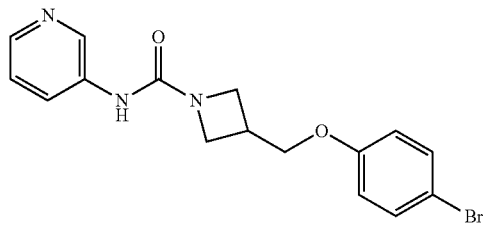 [SMILES: O=C(Nc1cccnc1)N1CC(COc2ccc(Br)cc2)C1]

MS (ESI⁺): calcd. for C₁₆H₁₆BrN₃O₂, 361.04. m/z found, 362.1 (M+H)⁺. ¹H NMR (d₆-DMSO): 8.66 (d, J=2.1 Hz, 1H), 8.62 (s, 1H), 8.14 (dd, J=4.7, 1.5 Hz, 1H), 7.94-7.90 (m, 1H), 7.46 (d, J=9.0 Hz, 2H), 7.26 (dd, J=8.1, 4.4 Hz, 1H), 6.95 (d, J=9.1 Hz, 2H), 4.16 (d, J=6.6 Hz, 2H), 4.10 (t, J=8.3 Hz, 2H), 3.80 (dd, J=8.3, 5.4 Hz, 2H), 3.04-2.95 (m, 1H).

Example 4

3-(3-Ethoxy-phenoxymethyl)-azetidine-1-carboxylic acid pyridin-3-ylamide, trifluoroacetate salt

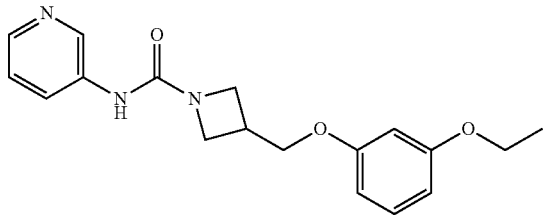 [SMILES: CCOc1cccc(OCC2CN(C(=O)Nc3cccnc3)C2)c1]

MS (ESI⁺): calcd. for C₁₈H₂₁N₃O₃, 327.16. m/z found, 328.2 (M+H)⁺. ¹H NMR (d₆-DMSO): 9.20 (s, 1H), 8.99 (d, J=2.3 Hz, 1H), 8.39 (d, J=4.5 Hz, 1H), 8.33-8.27 (m, 1H), 7.74 (dd, J=8.6, 5.3 Hz, 1H), 7.17 (t, J=8.3 Hz, 1H), 6.56-6.49 (m, 3H), 4.18-4.11 (m, 4H), 3.99 (q, J=7.0 Hz, 2H), 3.85 (dd, J=8.3, 5.5 Hz, 2H), 3.10-2.95 (m, 1H), 1.30 (t, J=7.0 Hz, 3H).

Example 5

3-(4-Trifluoromethoxy-phenoxymethyl)-azetidine-1-carboxylic acid pyridin-3-ylamide

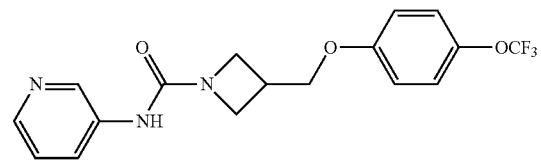 [SMILES: O=C(Nc1cccnc1)N1CC(COc2ccc(OC(F)(F)F)cc2)C1]

MS (ESI⁺): calcd. for C₁₇H₁₆F₃N₃O₃, 367.11. m/z found, 368.1 (M+H)⁺. ¹H NMR (d₆-DMSO): ¹H NMR (500 MHz, DMSO): 8.66 (d, J=2.5 Hz, 1H), 8.62 (s, 1H), 8.14 (dd, J=4.6, 1.5 Hz, 1H), 7.96-7.90 (m, 1H), 7.30 (d, J=9.1 Hz, 2H), 7.26 (dd, J=8.3, 4.7 Hz, 1H), 7.07 (d, J=9.2 Hz, 2H), 4.19 (d, J=6.6 Hz, 2H), 4.11 (t, J=8.3 Hz, 2H), 3.82 (dd, J=8.3, 5.4 Hz, 2H), 3.07-2.97 (m, 1H).

Example 6

3-(3-Trifluoromethoxy-phenoxymethyl)-azetidine-1-carboxylic acid pyridin-3-ylamide

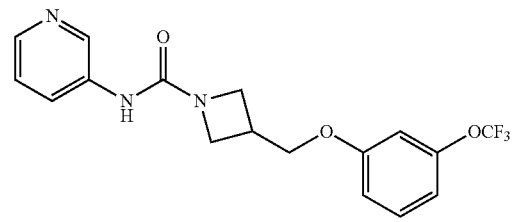 [SMILES: O=C(Nc1cccnc1)N1CC(COc2cccc(OC(F)(F)F)c2)C1]

MS (ESI⁺): calcd. for C₁₇H₁₆F₃N₃O₃, 367.11. m/z found, 368.1 (M+H)⁺. ¹H NMR (d₆-DMSO): 8.66 (d, J=2.5 Hz, 1H), 8.62 (s, 1H), 8.14 (dd, J=4.6, 1.4 Hz, 1H), 7.95-7.90 (m, 1H), 7.42 (t, J=8.3 Hz, 1H), 7.26 (dd, J=8.3, 4.7 Hz, 1H), 7.03 (d, J=8.3, 2.3 Hz, 1H), 6.97 (s, 1H), 6.95 (d, J=9.1 Hz, 1H), 4.22 (d, J=6.7 Hz, 2H), 4.11 (t, J=8.3 Hz, 2H), 3.82 (dd, J=8.3, 5.4 Hz, 2H), 3.07-2.97 (m, 1H).

Example 7

3-(Benzo[1,3]dioxol-5-yloxymethyl)-azetidine-1-carboxylic acid pyridin-3-ylamide

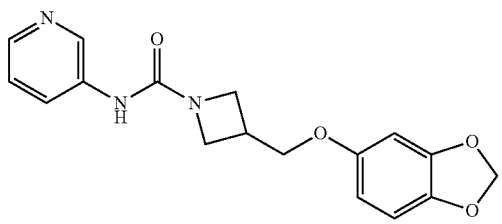 [SMILES: O=C(Nc1cccnc1)N1CC(COc2ccc3c(c2)OCO3)C1]

MS (ESI+): calcd. for $C_{17}H_{17}N_3O_4$, 327.12. m/z found, 328.2 (M+H)+. $^1$H NMR (d$_6$-DMSO): 8.66 (d, J=2.1 Hz, 1H), 8.61 (s, 1H), 8.13 (dd, J=4.6, 1.5 Hz, 1H), 7.94-7.90 (m, 1H), 7.26 (dd, J=8.3, 4.7 Hz, 1H), 6.81 (d, J=8.5 Hz, 1H), 6.66 (d, J=2.5 Hz, 1H), 6.40 (dd, J=8.5, 2.5 Hz, 1H), 5.96 (s, 2H), 4.12-4.05 (m, 4H), 3.78 (dd, J=8.3, 5.4 Hz, 2H), 3.01-2.91 (m, 1H).

Example 8

3-(3-Trifluoromethyl-phenoxymethyl)-azetidine-1-carboxylic acid pyridin-3-ylamide, trifluoroacetate salt

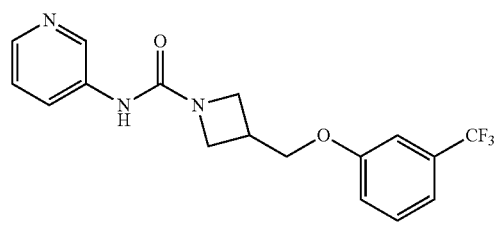 [SMILES: O=C(Nc1cccnc1)N1CC(COc2cccc(C(F)(F)F)c2)C1]

MS (ESI+): calcd. for $C_{17}H_{16}F_3N_3O_2$, 351.12. m/z found, 352.2 (M+H)+. $^1$H NMR (d$_6$-DMSO): 9.29 (s, 1H), 9.04 (s, 1H), 8.42 (d, J=4.9 Hz, 1H), 8.35 (d, J=8.6 Hz, 1H), 7.80 (dd, J=8.6, 5.3 Hz, 1H), 7.54 (t, J=7.8 Hz, 1H), 7.33-7.26 (m, 3H), 4.27 (d, J=6.5 Hz, 2H), 4.16 (t, J=8.4 Hz, 2H), 3.93-3.83 (m, 2H), 3.12-3.00 (m, 1H).

Example 9

3-(Quinolin-2-yloxymethyl)-azetidine-1-carboxylic acid pyridin-3-ylamide

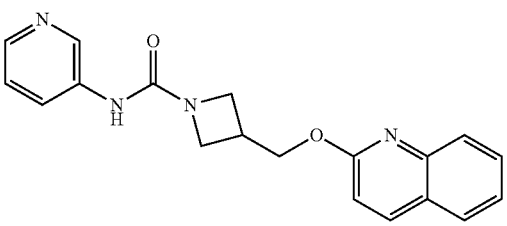 [SMILES: O=C(Nc1cccnc1)N1CC(COc2ccc3ccccc3n2)C1]

MS (ESI+): calcd. for $C_{19}H_{18}N_4O_2$, 334.14. m/z found, 335.2 (M+H)+. $^1$H NMR (d$_6$-DMSO): 8.68 (d, J=2.3 Hz, 1H), 8.64 (s, 1H), 8.25 (d, J=8.7 Hz, 1H), 8.14 (dd, J=4.6, 1.2 Hz, 1H), 7.96-7.91 (m, 1H), 7.89 (dd, J=8.0, 1.1 Hz, 1H), 7.78 (d, J=8.4 Hz, 1H), 7.70-7.65 (m, 1H), 7.47-7.42 (m, 1H), 7.27 (dd, J=8.3, 4.7 Hz, 1H), 7.04 (d, J=8.8 Hz, 1H), 4.62 (d, J=6.7 Hz, 2H), 4.14 (t, J=8.4 Hz, 2H), 3.88 (dd, J=8.3, 5.6 Hz, 2H), 3.14-3.04 (m, 1H).

Example 10

3-(3-Chloro-4-trifluoromethyl-phenoxymethyl)-azetidine-1-carboxylic acid pyridin-3-ylamide

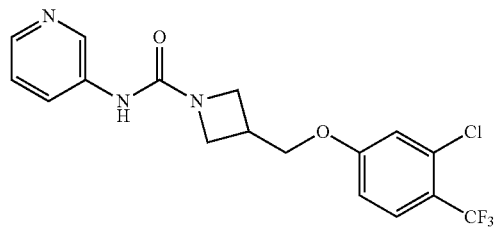 [SMILES: O=C(Nc1cccnc1)N1CC(COc2ccc(C(F)(F)F)c(Cl)c2)C1]

MS (ESI+): calcd. for $C_{17}H_{15}ClF_3N_3O_2$, 385.08. m/z found, 386.1 (M+H)+. $^1$H NMR (d$_6$-DMSO): 8.67 (d, J=2.4 Hz, 1H), 8.63 (s, 1H), 8.14 (dd, J=4.6, 1.3 Hz, 1H), 7.95-7.90 (m, 1H), 7.64 (d, J=8.9 Hz, 1H), 7.39 (d, J=3.0 Hz, 1H), 7.32 (dd, J=8.9, 3.0 Hz, 1H), 7.26 (dd, J=8.3, 4.7 Hz, 1H), 4.27 (d, J=6.6 Hz, 2H), 4.11 (t, J=8.3 Hz, 2H), 3.82 (dd, J=8.3, 5.4 Hz, 2H), 3.07-2.97 (m, 1H).

Example 11

3-(3-Ethynyl-phenoxymethyl)-azetidine-1-carboxylic acid pyridin-3-ylamide

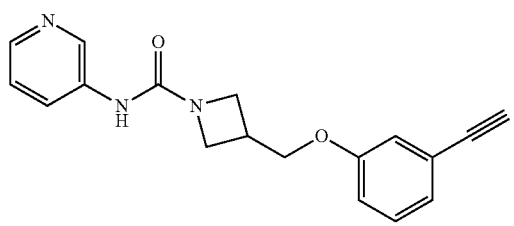 [SMILES: C#Cc1cccc(OCC2CN(C(=O)Nc3cccnc3)C2)c1]

MS (ESI+): calcd. for $C_{18}H_{17}N_3O_2$, 307.13. m/z found, 308.2 (M+H)+. $^1$H NMR (d$_6$-DMSO): 8.66 (d, J=2.3 Hz, 1H), 8.59 (s, 1H), 8.13 (dd, J=4.7, 1.5 Hz, 1H), 7.96-7.88 (m, 1H), 7.30 (t, J=8.1 Hz, 1H), 7.25 (dd, J=8.3, 4.9 Hz, 1H), 7.09-6.99 (m, 3H), 4.19 (d, J=6.7 Hz, 2H), 4.15 (s, 1H), 4.10 (t, J=8.4 Hz, 2H), 3.81 (dd, J=8.4, 5.4 Hz, 2H), 3.07-2.93 (m, 1H).

Example 12

3-(3-Butoxy-phenoxymethyl)-azetidine-1-carboxylic acid pyridin-3-ylamide

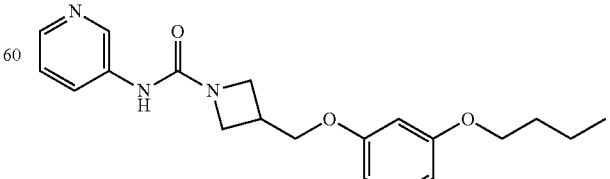

MS (ESI+): calcd. for C20H25N3O3, 355.19. m/z found, 356.2 (M+H)+. 1H NMR (d6-DMSO): 8.66 (d, J=2.4 Hz, 1H), 8.58 (s, 1H), 8.13 (dd, J=4.6, 1.4 Hz, 1H), 7.95-7.89 (m, 1H), 7.25 (dd, J=8.4, 4.6 Hz, 1H), 7.16 (dd, J=8.8, 7.9 Hz, 1H), 6.56-6.48 (m, 3H), 4.14 (d, J=6.6 Hz, 2H), 4.10 (t, J=8.4 Hz, 2H), 3.93 (t, J=6.5 Hz, 2H), 3.80 (dd, J=8.4, 5.4 Hz, 2H), 3.05-2.93 (m, 1H), 1.73-1.60 (m, 2H), 1.50-1.34 (m, 2H), 0.93 (t, J=7.4 Hz, 3H).

Example 13

3-(5,6,7,8-Tetrahydro-naphthalen-2-yloxymethyl)-azetidine-1-carboxylic acid pyridin-3-ylamide

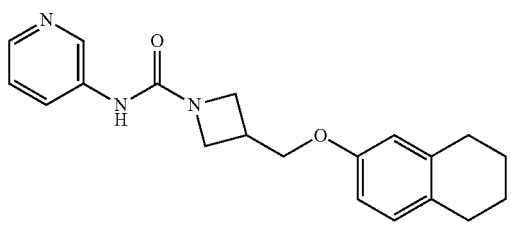 [SMILES: O=C(Nc1cccnc1)N1CC(COc2ccc3c(c2)CCCC3)C1]

MS (ESI+): calcd. for C20H23N3O2, 337.18. m/z found, 338.2 (M+H)+. 1H NMR (d6-DMSO): 8.66 (d, J=2.0 Hz, 1H), 8.61 (s, 1H), 8.14 (dd, J=4.6, 1.5 Hz, 1H), 7.95-7.90 (m, 1H), 7.26 (dd, J=8.1, 4.8 Hz, 1H), 6.95 (d, J=8.3 Hz, 1H), 6.69 (dd, J=8.3, 2.7 Hz, 1H), 6.65 (d, J=2.5 Hz, 1H), 4.12-4.06 (m, 4H), 3.79 (dd, J=8.3, 5.4 Hz, 2H), 3.03-2.93 (m, 1H), 2.70-2.65 (m, 2H), 2.65-2.60 (m, 2H), 1.75-1.64 (m, 4H).

Example 14

3-(Quinolin-7-yloxymethyl)-azetidine-1-carboxylic acid pyridin-3-ylamide

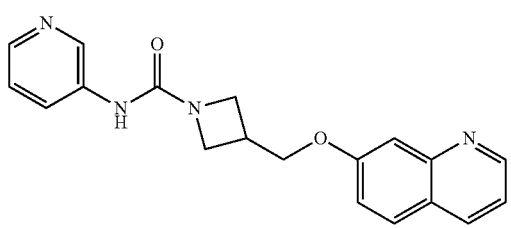 [SMILES: O=C(Nc1cccnc1)N1CC(COc2ccc3cccnc3c2)C1]

MS (ESI+): calcd. for C19H18N4O2, 334.14. m/z found, 335.2 (M+H)+. 1H NMR (d6-DMSO): 8.83 (dd, J=4.3, 1.7 Hz, 1H), 8.69 (s, 1H), 8.66 (s, 1H), 8.29 (dd, J=8.2, 1.4 Hz, 1H), 8.15 (d, J=4.0 Hz, 1H), 7.97-7.93 (m, 1H), 7.90 (d, J=9.0 Hz, 1H), 7.46 (d, J=2.4 Hz, 1H), 7.39 (dd, J=8.2, 4.3 Hz, 1H), 7.31-7.26 (m, 2H), 4.36 (d, J=6.6 Hz, 2H), 4.16 (t, J=8.4 Hz, 2H), 3.89 (dd, J=8.3, 5.4 Hz, 2H), 3.17-3.04 (m, 1H).

Example 15

3-(Quinolin-6-yloxymethyl)-azetidine-1-carboxylic acid pyridin-3-ylamide, trifluoroacetate salt

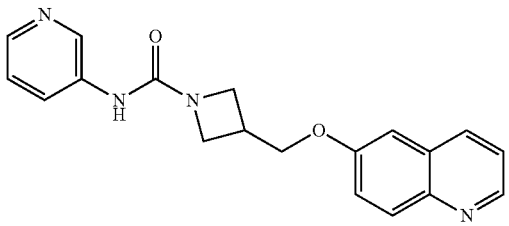 [SMILES: O=C(Nc1cccnc1)N1CC(COc2ccc3ncccc3c2)C1]

MS (ESI+): calcd. for C19H18N4O2, 334.14. m/z found, 335.2 (M+H)+. 1H NMR (d6-DMSO): 9.19 (s, 1H), 8.98 (s, 1H), 8.86 (dd, J=4.4, 1.4 Hz, 1H), 8.46 (d, J=8.1 Hz, 1H), 8.38 (d, J=5.0 Hz, 1H), 8.28 (d, J=8.6 Hz, 1H), 8.00 (d, J=8.9 Hz, 1H), 7.72 (dd, J=8.4, 5.3 Hz, 1H), 7.65 (dd, J=8.4, 4.4 Hz, 1H), 7.59-7.50 (m, 2H), 4.36 (d, J=6.5 Hz, 2H), 4.20 (t, J=8.4 Hz, 2H), 3.92 (dd, J=8.2, 5.5 Hz, 2H), 3.18-3.11 (m, 1H).

Example 16

3-(4-Phenoxy-phenoxymethyl)-azetidine-1-carboxylic acid pyridin-3-ylamide

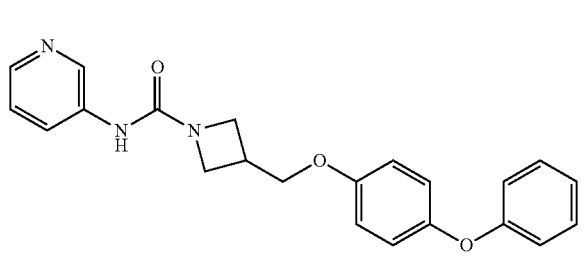 [SMILES: O=C(Nc1cccnc1)N1CC(COc2ccc(Oc3ccccc3)cc2)C1]

MS (ESI+): calcd. for C22H21N3O3, 375.16. m/z found, 376.2 (M+H)+. 1H NMR (d6-DMSO): 8.67 (d, J=2.2 Hz, 1H), 8.63 (s, 1H), 8.14 (dd, J=4.7, 1.4 Hz, 1H), 7.96-7.89 (m, 1H), 7.38-7.32 (m, 2H), 7.26 (dd, J=8.3, 4.7 Hz, 1H), 7.10-7.04 (m, 1H), 7.03-6.97 (m, 4H), 6.95-6.89 (m, 2H), 4.15 (d, J=6.6 Hz, 2H), 4.11 (t, J=8.3 Hz, 2H), 3.82 (dd, J=8.3, 5.4 Hz, 2H), 3.07-2.97 (m, 1H).

Example 17

3-(3-Phenoxy-phenoxymethyl)-azetidine-1-carboxylic acid pyridin-3-ylamide

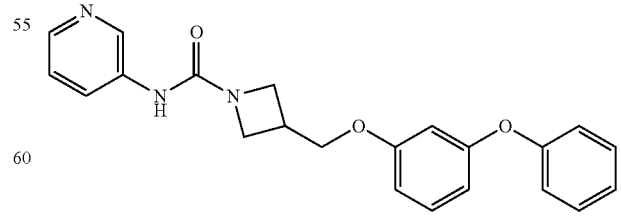

MS (ESI+): calcd. for C22H21N3O3, 375.16. m/z found, 376.2 (M+H)+. 1H NMR (d6-DMSO): 8.66 (d, J=2.0 Hz, 1H), 8.60 (s, 1H), 8.13 (dd, J=4.7, 1.5 Hz, 1H), 7.95-7.88 (m, 1H), 7.40 (dd, J=8.6, 7.4 Hz, 2H), 7.32-7.23 (m, 2H), 7.17-7.12 (m, 1H), 7.03 (dd, J=8.7, 1.0 Hz, 2H), 6.76 (d, J=10.0 Hz, 1H), 6.61 (t, J=2.3 Hz, 1H), 6.56 (d, J=7.4 Hz, 1H), 4.15 (d, J=6.7 Hz, 2H), 4.09 (t, J=8.3 Hz, 2H), 3.80 (dd, J=8.3, 5.5 Hz, 2H), 3.04-2.95 (m, 1H).

Example 18

3-(Biphenyl-4-yloxymethyl)-azetidine-1-carboxylic acid pyridin-3-ylamide

MS (ESI+): calcd. for $C_{22}H_{21}N_3O_2$, 359.16. m/z found, 360.2 (M+H)+. $^1$H NMR ($d_6$-DMSO): 8.67 (d, J=2.6 Hz, 1H), 8.63 (s, 1H), 8.14 (dd, J=4.6, 1.4 Hz, 1H), 7.93 (d, J=8.4 Hz, 1H), 7.65-7.57 (m, 4H), 7.43 (t, J=7.7 Hz, 2H), 7.31 (t, J=7.4 Hz, 1H), 7.26 (dd, J=8.3, 4.7 Hz, 1H), 7.07 (d, J=8.7 Hz, 2H), 4.22 (d, J=6.6 Hz, 2H), 4.13 (t, J=8.3 Hz, 2H), 3.84 (dd, J=8.3, 5.4 Hz, 2H), 3.09-3.00 (m, 1H).

Example 19

3-(4-Benzyloxy-phenoxymethyl)-azetidine-1-carboxylic acid pyridin-3-ylamide

MS (ESI+): calcd. for $C_{23}H_{23}N_3O_3$, 389.17. m/z found, 390.2 (M+H)+. $^1$H NMR ($d_6$-DMSO): 8.66 (d, J=2.2 Hz, 1H), 8.61 (s, 1H), 8.14 (d, J=3.5 Hz, 1H), 7.95-7.90 (m, 1H), 7.45-7.41 (m, 2H), 7.40-7.36 (m, 2H), 7.35-7.29 (m, 1H), 7.26 (dd, J=8.3, 4.7 Hz, 1H), 6.97-6.87 (m, 4H), 5.04 (s, 2H), 4.13-4.05 (m, 4H), 3.80 (dd, J=8.3, 5.4 Hz, 2H), 3.04-2.90 (s, 1H).

Example 20

3-(Naphthalen-2-yloxymethyl)-azetidine-1-carboxylic acid pyridin-3-ylamide

MS (ESI+): calcd. for $C_{20}H_{19}N_3O_2$, 333.15. m/z found, 334.2 (M+H)+. $^1$H NMR ($d_6$-DMSO): 8.68 (d, J=2.5 Hz, 1H), 8.66 (s, 1H), 8.14 (dd, J=4.6, 1.4 Hz, 1H), 7.96-7.92 (m, 1H), 7.86-7.79 (m, 3H), 7.46 (t, J=7.5 Hz, 1H), 7.39 (d, J=2.3 Hz, 1H), 7.35 (t, J=7.5 Hz, 1H), 7.26 (dd, J=8.3, 4.7 Hz, 1H), 7.19 (dd, J=8.9, 2.5 Hz, 1H), 4.30 (d, J=6.6 Hz, 2H), 4.15 (t, J=8.3 Hz, 2H), 3.90-3.83 (m, 2H), 3.14-3.03 (m, 1H).

Example 21

3-(3,4-Dichloro-phenoxymethyl)-azetidine-1-carboxylic acid pyridin-3-ylamide

MS (ESI+): calcd. for $C_{16}H_{15}Cl_2N_3O_2$, 351.05. m/z found, 352.1 (M+H)+. $^1$H NMR ($d_6$-DMSO): 8.66 (d, J=2.2 Hz, 1H), 8.62 (s, 1H), 8.14 (dd, J=4.6, 1.4 Hz, 1H), 7.94-7.90 (m, 1H), 7.53 (d, J=8.9 Hz, 1H), 7.29 (d, J=2.9 Hz, 1H), 7.26 (dd, J=8.1, 4.4 Hz, 1H), 7.00 (dd, J=8.9, 2.9 Hz, 1H), 4.21 (d, J=6.7 Hz, 2H), 4.10 (t, J=8.4 Hz, 2H), 3.80 (dd, J=8.3, 5.4 Hz, 2H), 3.05-2.95 (m, 1H).

Example 22

3-(8-Chloro-quinolin-2-yloxymethyl)-azetidine-1-carboxylic acid pyridin-3-ylamide MS (ESI+): calcd. for $C_{19}H_{17}ClN_4O_2$, 368.10. m/z found, 369.1 (M+H)+. $^1$H NMR ($d_6$-DMSO): 8.66 (d, J=2.3 Hz, 1H), 8.63 (s, 1H), 8.34 (d, J=8.9 Hz, 1H), 8.14 (dd, J=4.6, 1.4 Hz, 1H), 7.95-7.85 (m, 3H), 7.43 (t, J=7.8 Hz, 1H), 7.26 (dd, J=8.2, 4.4 Hz, 1H), 7.15 (d, J=8.8 Hz, 1H), 4.70 (d, J=6.6 Hz, 2H), 4.14 (t, J=8.4 Hz, 2H), 3.90 (dd, J=8.3, 5.5 Hz, 2H), 3.18-3.06 (m, 1H).

Example 23

3-(3-Benzyloxy-phenoxymethyl)-azetidine-1-carboxylic acid pyridin-3-ylamide

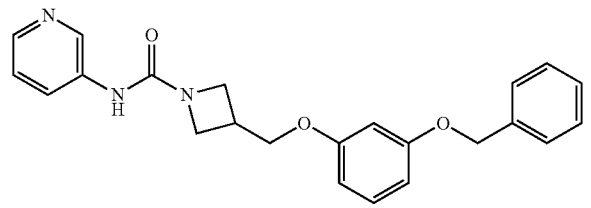 [SMILES: O=C(Nc1cccnc1)N1CC(COc2cccc(OCc3ccccc3)c2)C1]

MS (ESI$^+$): calcd. for $C_{23}H_{23}N_3O_3$, 389.17. m/z found, 390.2 (M+H)$^+$. $^1$H NMR (d$_6$-DMSO): 8.67 (d, J=2.3 Hz, 1H), 8.62 (s, 1H), 8.14 (d, J=3.4 Hz, 1H), 7.96-7.89 (m, 1H), 7.46-7.42 (m, 2H), 7.42-7.36 (m, 2H), 7.35-7.30 (m, 1H), 7.26 (dd, J=8.3, 4.7 Hz, 1H), 7.19 (t, J=8.1 Hz, 1H), 6.64-6.58 (m, 2H), 6.58-6.52 (m, 1H), 5.08 (2H, s), 4.15 (d, J=6.7 Hz, 2H), 4.10 (t, J=8.3 Hz, 2H), 3.80 (dd, J=8.3, 5.4 Hz, 2H), 3.04-2.94 (m, 1H).

Example 24

3-[3-(4-Methanesulfonyl-phenoxy)-phenoxymethyl]-azetidine-1-carboxylic acid pyridin-3-ylamide

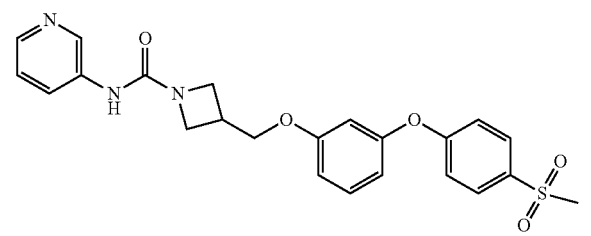 [SMILES: CS(=O)(=O)c1ccc(Oc2cccc(OCC3CN(C(=O)Nc4cccnc4)C3)c2)cc1]

MS (ESI$^+$): calcd. for $C_{23}H_{23}N_3O_5S$, 453.14. m/z found, 454.2 (M+H)$^+$. $^1$H NMR (d$_6$-DMSO): 8.66 (d, J=2.6 Hz, 1H), 8.62 (s, 1H), 8.13 (dd, J=4.7, 1.4 Hz, 1H), 7.93-7.87 (m, 3H), 7.38 (t, J=8.2 Hz, 1H), 7.25 (dd, J=8.4, 4.7 Hz, 1H), 7.17 (d, J=8.8 Hz, 2H), 6.89 (dd, J=8.4, 2.4 Hz, 1H), 6.79 (t, J=2.3 Hz, 1H), 6.72 (dd, J=8.1, 2.2 Hz, 1H), 4.18 (d, J=6.7 Hz, 2H), 4.10 (s, 2H), 3.81 (s, 2H), 3.19 (s, 3H), 3.07-2.94 (m, 1H).

Example 25

3-[3-(4-Trifluoromethoxy-phenoxy)-phenoxymethyl]-azetidine-1-carboxylic acid pyridin-3-ylamide

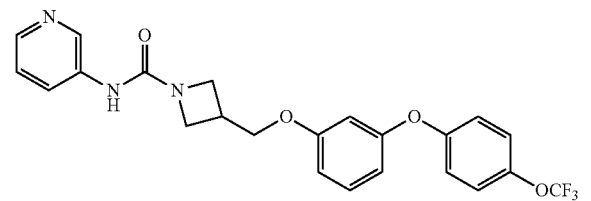 [SMILES: O=C(Nc1cccnc1)N1CC(COc2cccc(Oc3ccc(OC(F)(F)F)cc3)c2)C1]

MS (ESI$^+$): calcd. for $C_{23}H_{20}F_3N_3O_4$, 459.14. m/z found, 460.2 (M+H)$^+$. $^1$H NMR (d$_6$-DMSO): 8.66 (d, J=2.4 Hz, 1H), 8.61 (s, 1H), 8.13 (dd, J=4.6, 1.4 Hz, 1H), 7.94-7.88 (m, 1H), 7.39 (d, J=8.6 Hz, 2H), 7.32 (t, J=8.2 Hz, 1H), 7.25 (dd, J=8.4, 4.7 Hz, 1H), 7.11 (d, J=9.1 Hz, 2H), 6.81 (dd, J=8.2, 2.0 Hz, 1H), 6.69 (t, J=2.3 Hz, 1H), 6.61 (dd, J=8.1, 1.9 Hz, 1H), 4.16 (d, J=6.7 Hz, 2H), 4.09 (t, J=8.3 Hz, 2H), 3.80 (dd, J=8.4, 5.5 Hz, 2H), 3.05-2.93 (m, 1H).

Example 26

3-[3-(4-Chloro-phenoxy)-phenoxymethyl]-azetidine-1-carboxylic acid pyridin-3-ylamide

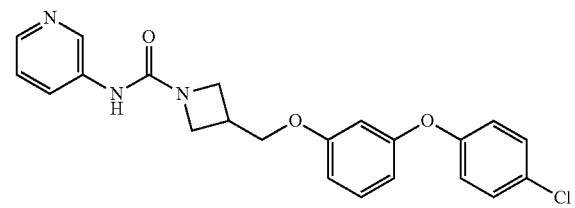 [SMILES: O=C(Nc1cccnc1)N1CC(COc2cccc(Oc3ccc(Cl)cc3)c2)C1]

MS (ESI$^+$): calcd. for $C_{22}H_{20}ClN_3O_3$, 409.12. m/z found, 410.2 (M+H)$^+$. $^1$H NMR (d$_6$-DMSO): 8.66 (d, J=2.5 Hz, 1H), 8.61 (s, 1H), 8.13 (dd, J=4.6, 1.4 Hz, 1H), 7.94-7.89 (m, 1H), 7.43 (d, J=8.9 Hz, 2H), 7.31 (t, J=8.2 Hz, 1H), 7.26 (dd, J=8.3, 4.7 Hz, 1H), 7.04 (d, J=8.9 Hz, 2H), 6.79 (dd, J=8.3, 1.8 Hz, 1H), 6.65 (t, J=2.3 Hz, 1H), 6.59 (dd, J=8.1, 2.2 Hz, 1H), 4.15 (d, J=6.7 Hz, 2H), 4.09 (t, J=8.4 Hz, 2H), 3.80 (dd, J=8.3, 5.4 Hz, 2H), 3.03-2.95 (m, 1H).

Example 27

3-{2-[3-(4-Methanesulfonyl-phenoxy)-phenoxy]-ethyl}-azetidine-1-carboxylic acid pyridin-3-ylamide

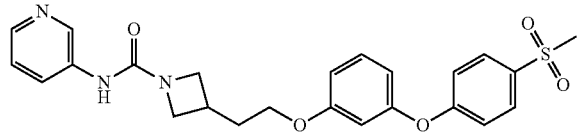 [SMILES: CS(=O)(=O)c1ccc(Oc2cccc(OCCC3CN(C(=O)Nc4cccnc4)C3)c2)cc1]

MS (ESI$^+$): calcd. for $C_{24}H_{25}N_3O_5S$, 467.15. m/z found, 468.2 (M+H)$^+$. $^1$H NMR (d$_6$-DMSO): 8.65 (d, J=2.4 Hz, 1H), 8.56 (s, 1H), 8.12 (d, J=4.7 Hz, 1H), 7.91-7.88 (m, 3H), 7.37 (t, J=8.2 Hz, 1H), 7.25 (dd, J=8.3, 4.7 Hz, 1H), 7.17 (d, J=8.8 Hz, 2H), 6.85 (dd, J=8.2, 2.2 Hz, 1H), 6.75-6.72 (m, 1H), 6.70 (dd, J=8.1 Hz, 1H), 4.08 (t, J=8.2 Hz, 2H), 4.00 (t, J=6.1 Hz, 2H), 3.71 (dd, J=8.1, 5.9 Hz, 2H), 3.19 (s, 3H), 2.79-2.68 (m, 1H), 2.08-1.97 (m, 2H).

Example 28

3-{2-[3-(4-Chloro-phenoxy)-phenoxy]-ethyl}-azetidine-1-carboxylic acid (4-chloro-pyridin-3-yl)-amide

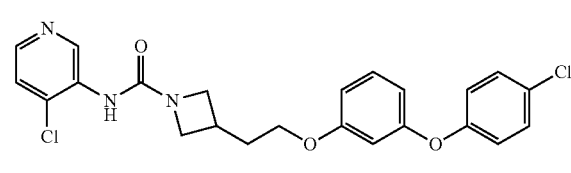 [SMILES: O=C(Nc1cnccc1Cl)N1CC(CCOc2cccc(Oc3ccc(Cl)cc3)c2)C1]

MS (ESI+): calcd. for C23H21Cl2N3O3, 457.10. m/z found, 458.1 (M+H)+. 1H NMR (d6-DMSO): 8.69 (s, 1H), 8.26 (d, J=5.2 Hz, 1H), 8.15 (s, 1H), 7.55 (d, J=5.3 Hz, 1H), 7.43 (d, J=8.8 Hz, 2H), 7.29 (t, J=8.1 Hz, 1H), 7.04 (d, J=8.8 Hz, 2H), 6.74 (d, J=8.4 Hz, 1H), 6.60 (s, 1H), 6.57 (d, J=10.1 Hz, 1H), 4.09 (t, J=8.4 Hz, 2H), 3.98 (t, J=6.0 Hz, 2H), 3.72 (dd, J=7.6, 6.6 Hz, 2H), 2.80-2.70 (m, 1H), 2.07-1.97 (m, 2H).

Example 29

3-{2-[3-(4-Trifluoromethoxy-phenoxy)-phenoxy]-ethyl}-azetidine-1-carboxylic acid pyridin-3-ylamide

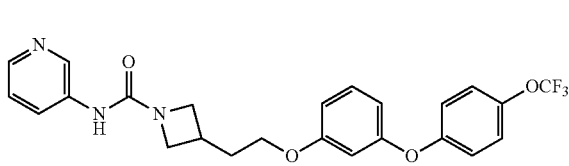 [SMILES: O=C(Nc1cccnc1)N1CC(CCOc2cccc(Oc3ccc(OC(F)(F)F)cc3)c2)C1]

MS (ESI+): calcd. for C24H22F3N3O4, 473.16. m/z found, 474.2 (M+H)+. 1H NMR (d6-DMSO): 8.65 (d, J=2.5 Hz, 1H), 8.56 (s, 1H), 8.13 (dd, J=4.6, 1.3 Hz, 1H), 7.94-7.88 (m, 1H), 7.39 (d, J=8.9 Hz, 2H), 7.31 (t, J=8.2 Hz, 1H), 7.25 (dd, J=8.3, 4.7 Hz, 1H), 7.11 (d, J=9.0 Hz, 2H), 6.77 (dd, J=8.3, 2.3 Hz, 1H), 6.66-6.62 (m, 1H), 6.59 (dd, J=8.1, 2.2 Hz, 1H), 4.08 (t, J=8.2 Hz, 2H), 3.99 (t, J=6.1 Hz, 2H), 3.71 (dd, J=8.1, 5.9 Hz, 2H), 2.79-2.67 (m, 1H), 2.05-1.98 (m, 2H).

Example 30

3-[2-(4-Trifluoromethoxy-phenoxy)-ethyl]-azetidine-1-carboxylic acid pyridin-3-ylamide

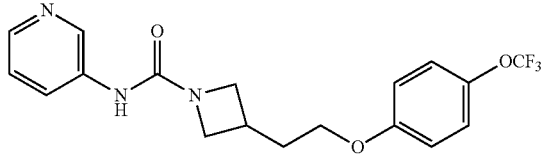 [SMILES: O=C(Nc1cccnc1)N1CC(CCOc2ccc(OC(F)(F)F)cc2)C1]

MS (ESI+): calcd. for C18H18F3N3O3, 381.13. m/z found, 382.1 (M+H)+. 1H NMR (d6-DMSO): 8.66 (d, J=2.5 Hz, 1H), 8.57 (s, 1H), 8.13 (dd, J=4.6, 1.4 Hz, 1H), 7.94-7.90 (m, 1H), 7.29 (d, J=8.8 Hz, 2H), 7.25 (dd, J=8.3, 4.7 Hz, 1H), 7.02 (d, J=9.1 Hz, 2H), 4.09 (t, J=8.2 Hz, 2H), 4.01 (t, J=6.2 Hz, 2H), 3.72 (dd, J=8.1, 5.9 Hz, 2H), 2.79-2.69 (m, 1H), 2.08-1.99 (m, 2H).

Example 31

3-[2-(3-Trifluoromethoxy-phenoxy)-ethyl]-azetidine-1-carboxylic acid pyridin-3-ylamide

MS (ESI+): calcd. for C18H18F3N3O3, 381.13. m/z found, 382.1 (M+H)+. 1H NMR (d6-DMSO): 8.66 (d, J=2.5 Hz, 1H), 8.57 (s, 1H), 8.13 (dd, J=4.6, 1.4 Hz, 1H), 7.94-7.90 (m, 1H), 7.41 (t, J=8.2 Hz, 1H), 7.25 (dd, J=8.3, 4.7 Hz, 1H), 7.02-6.96 (m, 1H), 6.95-6.90 (m, 2H), 4.09 (t, J=8.2 Hz, 2H), 4.03 (t, J=6.2 Hz, 2H), 3.72 (dd, J=8.1, 5.9 Hz, 2H), 2.80-2.69 (m, 1H), 2.04 (d, J=7.2 Hz, 2H).

Example 32

3-[2-(3-Phenoxy-phenoxy)-ethyl]-azetidine-1-carboxylic acid pyridin-3-ylamide

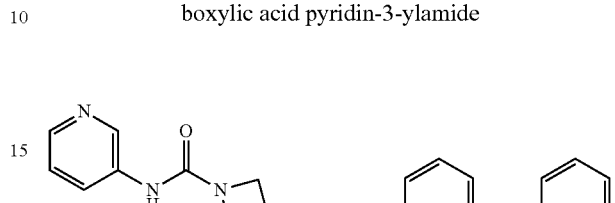

MS (ESI+): calcd. for C23H23N3O3, 389.17. m/z found, 390.2 (M+H)+. 1H NMR (d6-DMSO): 8.65 (d, J=2.3 Hz, 1H), 8.56 (s, 1H), 8.13 (d, J=4.6 Hz, 1H), 7.94-7.89 (m, 1H), 7.40 (t, J=7.6 Hz, 2H), 7.30-7.22 (m, 2H), 7.15 (t, 1H), 7.02 (d, J=8.6 Hz, 2H), 6.71 (d, J=8.3 Hz, 1H), 6.58-6.51 (m, 2H), 4.08 (t, J=8.2 Hz, 2H), 3.97 (t, J=6.1 Hz, 2H), 3.74-3.66 (m, 2H), 2.78-2.67 (m, 1H), 2.05-1.95 (m, 2H).

Example 33

3-[2-(3-Butoxy-phenoxy)-ethyl]-azetidine-1-carboxylic acid pyridin-3-ylamide

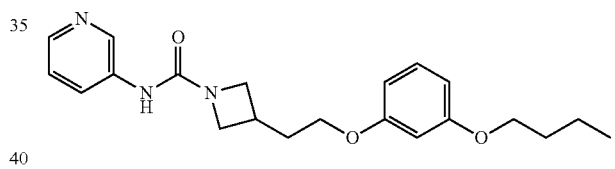

MS (ESI+): calcd. for C21H27N3O3, 369.21. m/z found, 370.2 (M+H)+. 1H NMR (d6-DMSO): 8.66 (d, J=2.3 Hz, 1H), 8.53 (s, 1H), 8.13 (dd, J=4.6, 1.5 Hz, 1H), 7.95-7.88 (m, 1H), 7.24 (dd, J=8.3, 4.7 Hz, 1H), 7.15 (t, J=8.1 Hz, 1H), 6.52-6.44 (m, 3H), 4.09 (t, J=8.2 Hz, 2H), 4.01-3.89 (m, 4H), 3.71 (dd, J=8.2, 5.8 Hz, 2H), 2.85-2.67 (m, 1H), 2.10-1.93 (m, 2H), 1.74-1.57 (m, 2H), 1.50-1.33 (m, 2H), 0.93 (t, J=7.4 Hz, 3H).

Example 34

3-[2-(3,4-Dichloro-phenoxy)-ethyl]-azetidine-1-carboxylic acid pyridin-3-ylamide

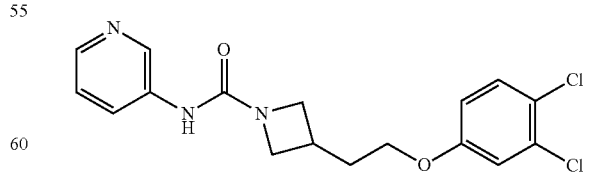

MS (ESI+): calcd. for C17H17Cl2N3O2, 365.07. m/z found, 366.1 (M+H)+. 1H NMR (d6-DMSO): 8.68 (d, J=2.4 Hz, 1H), 8.58 (s, 1H), 8.15 (dd, J=4.7, 1.1 Hz, 1H), 7.95 (d, J=8.4 Hz, 1H), 7.52 (d, J=8.9 Hz, 1H), 7.29 (dd, J=8.3, 4.8 Hz, 1H), 7.23 (d, J=2.9 Hz, 1H), 6.96 (dd, J=8.9, 2.9 Hz, 1H), 4.08 (t, J=8.3

Hz, 2H), 4.03 (t, J=6.2 Hz, 2H), 3.71 (dd, J=8.2, 5.9 Hz, 2H), 2.80-2.68 (m, 1H), 2.08-1.95 (m, 2H).

Example 35

3-[2-(Naphthalen-2-yloxy)-ethyl]-azetidine-1-carboxylic acid pyridin-3-ylamide, trifluoroacetate salt

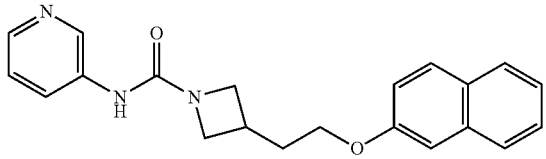 [SMILES: O=C(Nc1cccnc1)N1CC(CCOc2ccc3ccccc3c2)C1]

MS (ESI$^+$): calcd. for $C_{21}H_{21}N_3O_2$, 347.16. m/z found, 348.2 (M+H)$^+$. $^1$H NMR (d$_6$-DMSO): 8.98 (s, 1H), 8.91 (d, J=2.4 Hz, 1H), 8.31 (d, J=5.0 Hz, 1H), 8.20 (d, J=8.1 Hz, 1H), 7.86-7.75 (m, 3H), 7.61 (dd, J=8.3, 5.3 Hz, 1H), 7.45 (t, J=7.6 Hz, 1H), 7.38-7.28 (m, 2H), 7.15 (dd, J=9.0, 2.5 Hz, 1H), 4.21-4.07 (m, 4H), 3.83-3.73 (m, 2H), 2.88-2.75 (m, 1H), 2.17-2.07 (m, 2H).

Example 36

3-[2-(Quinolin-2-yloxy)-ethyl]-azetidine-1-carboxylic acid pyridin-3-ylamide

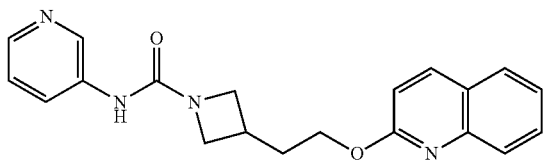 [SMILES: O=C(Nc1cccnc1)N1CC(CCOc2ccc3ccccc3n2)C1]

MS (ESI$^+$): calcd. for $C_{20}H_{20}N_4O_2$, 348.16. m/z found, 349.2 (M+H)$^+$. $^1$H NMR (d$_6$-DMSO): 8.66 (d, J=2.0 Hz, 1H), 8.54 (s, 1H), 8.24 (d, J=8.7 Hz, 1H), 8.12 (dd, J=4.6, 1.5 Hz, 1H), 7.93-7.89 (m, 1H), 7.88 (dd, J=8.0, 1.2 Hz, 1H), 7.77 (d, J=8.4 Hz, 1H), 7.69-7.62 (m, 1H), 7.48-7.36 (m, 1H), 7.24 (dd, J=8.6, 4.4 Hz, 1H), 7.00 (d, J=8.8 Hz, 1H), 4.45 (t, J=6.3 Hz, 2H), 4.11 (t, J=8.3 Hz, 2H), 3.76-3.67 (m, 2H), 2.83-2.69 (m, 1H), 2.16-2.03 (m, 2H).

Example 37

3-[2-(3-Ethynyl-phenoxy)-ethyl]-azetidine-1-carboxylic acid pyridin-3-ylamide, trifluoroacetate salt

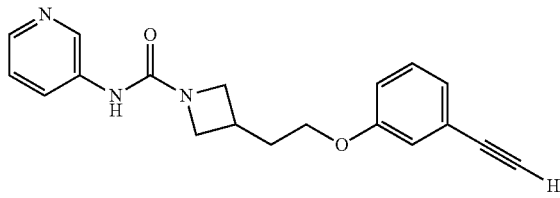 [SMILES: C#Cc1cccc(OCCC2CN(C(=O)Nc3cccnc3)C2)c1]

MS (ESI$^+$): calcd. for $C_{19}H_{19}N_3O_2$, 321.15. m/z found, 322.2 (M+H)$^+$. $^1$H NMR (d$_6$-DMSO): 9.11 (s, 1H), 8.98 (d, J=2.3 Hz, 1H), 8.37 (d, J=5.2 Hz, 1H), 8.32-8.26 (m, 1H), 7.72 (dd, J=8.5, 5.3 Hz, 1H), 7.29 (t, J=7.9 Hz, 1H), 7.09-6.93 (m, 3H), 4.17-4.08 (m, 3H), 4.02 (t, J=6.1 Hz, 2H), 3.76 (dd, J=8.3, 5.9 Hz, 2H), 2.86-2.65 (m, 1H), 2.04 (dd, J=13.4, 6.3 Hz, 2H).

Example 38

3-{2-[3-(4-Chloro-phenoxy)-phenoxy]-ethyl}-azetidine-1-carboxylic acid isoquinolin-4-ylamide

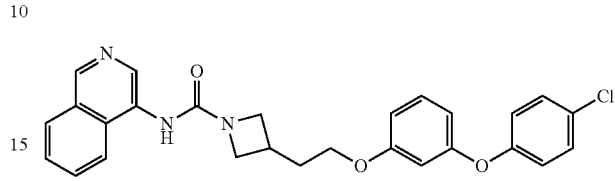

MS (ESI$^+$): calcd. for $C_{27}H_{24}ClN_3O_3$, 473.15. m/z found, 474.2 (M+H)$^+$. $^1$H NMR (d$_6$-DMSO): 9.09 (s, 1H), 8.51 (d, J=12.9 Hz, 2H), 8.11 (d, J=8.2 Hz, 1H), 8.02 (d, J=8.0 Hz, 1H), 7.78 (t, J=7.1 Hz, 1H), 7.68 (t, J=7.1 Hz, 1H), 7.43 (d, J=8.9 Hz, 2H), 7.30 (t, J=8.2 Hz, 1H), 7.04 (d, J=8.9 Hz, 2H), 6.76 (dd, J=8.2, 1.9 Hz, 1H), 6.62 (t, J=2.3 Hz, 1H), 6.58 (dd, J=7.9, 2.0 Hz, 1H), 4.15 (t, J=8.2 Hz, 2H), 4.01 (t, J=6.2 Hz, 2H), 3.78 (dd, J=8.0, 5.9 Hz, 2H), 2.84-2.74 (m, 1H), 2.10-2.01 (m, 2H).

Example 39

3-{2-[3-(4-Chloro-phenoxy)-phenoxy]-ethyl}-azetidine-1-carboxylic acid (6-[1,2,3]triazol-2-yl-pyridin-3-yl)-amide

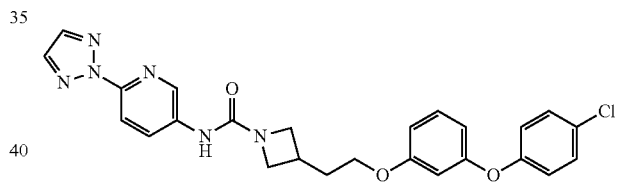

MS (ESI$^+$): calcd. for $C_{25}H_{23}ClN_6O_3$, 490.15. m/z found, 491.1 (M+H)$^+$. $^1$H NMR (d$_6$-DMSO): 8.82 (s, 1H), 8.65 (s, 1H), 8.20 (d, J=9.0 Hz, 1H), 8.10 (s, 2H), 7.89 (d, J=9.0 Hz, 1H), 7.43 (d, J=7.2 Hz, 2H), 7.30 (t, J=7.5 Hz, 1H), 7.04 (d, J=7.2 Hz, 2H), 6.75 (d, J=8.2 Hz, 1H), 6.62-6.60 (m, 1H), 6.58 (d, J=8.3 Hz, 1H), 4.11 (t, J=8.1 Hz, 2H), 3.99 (t, J=5.9 Hz, 2H), 3.77-3.70 (m, 2H), 2.80-2.71 (m, 1H), 2.08-1.98 (m, 2H).

Example 40

3-{2-[3-(4-Chloro-phenoxy)-phenoxy]-ethyl}-azetidine-1-carboxylic acid (1H-pyrrolo[2,3-b]pyridin-5-yl)-amide

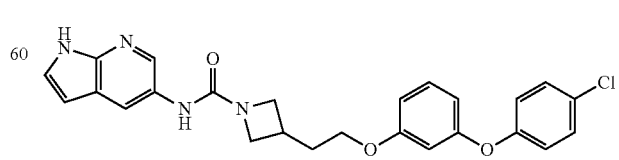

MS (ESI$^+$): calcd. for $C_{25}H_{23}ClN_4O_3$, 462.15. m/z found, 463.2 (M+H)$^+$. $^1$H NMR (d$_6$-DMSO): 11.38 (s, 1H), 8.27 (s, 1H), 8.20 (d, J=2.3 Hz, 1H), 8.01 (d, J=2.2 Hz, 1H), 7.43 (d, J=8.8 Hz, 2H), 7.40-7.35 (m, 1H), 7.30 (t, J=8.2 Hz, 1H), 7.04 (d, J=8.8 Hz, 2H), 6.75 (dd, J=8.3, 2.3 Hz, 1H), 6.61 (t, J=2.3 Hz, 1H), 6.59-6.55 (m, 1H), 6.36-6.32 (m, 1H), 4.06 (t, J=8.2 Hz, 2H), 3.99 (t, J=6.2 Hz, 2H), 3.69 (dd, J=8.0, 5.8 Hz, 2H), 2.78-2.66 (m, 1H), 2.08-1.96 (m, 2H).

Example 41

3-{2-[3-(4-Chloro-phenoxy)-phenoxy]-ethyl}-azetidine-1-carboxylic acid imidazo[1,2-a]pyridin-6-ylamide

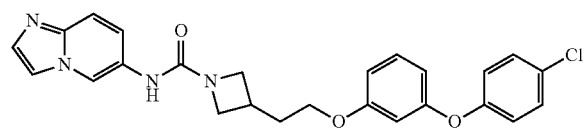 [SMILES: O=C(Nc1ccc2nccn2c1)N1CC(CCOc2cccc(Oc3ccc(Cl)cc3)c2)C1]

MS (ESI$^+$): calcd. for $C_{25}H_{23}ClN_4O_3$, 462.15. m/z found, 463.2 (M+H)$^+$. $^1$H NMR (d$_6$-DMSO): 8.88 (s, 1H), 8.37 (s, 1H), 7.91 (s, 1H), 7.48-7.40 (m, 4H), 7.30 (t, J=8.3 Hz, 1H), 7.22 (d, J=9.5 Hz, 1H), 7.04 (d, J=7.7 Hz, 2H), 6.77-6.73 (m, 1H), 6.61-6.59 (m, 1H), 6.59-6.55 (m, 1H), 4.08 (t, J=8.2 Hz, 2H), 3.98 (t, J=6.3 Hz, 2H), 3.73-3.65 (m, 2H), 2.79-2.69 (m, 1H), 2.06-1.96 (m, 2H).

Example 42

3-{2-[3-(4-Chloro-phenoxy)-phenoxy]-ethyl}-azetidine-1-carboxylic acid imidazo[1,2-a]pyridin-3-ylamide

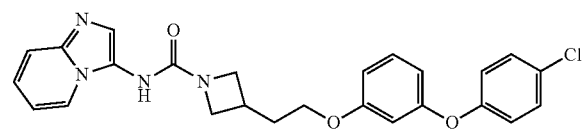 [SMILES: O=C(Nc1cnc2ccccn12)N1CC(CCOc2cccc(Oc3ccc(Cl)cc3)c2)C1]

MS (ESI$^+$): calcd. for $C_{25}H_{23}ClN_4O_3$, 462.15. m/z found, 463.2 (M+H)$^+$. $^1$H NMR (d$_6$-DMSO): 8.44 (s, 1H), 8.04 (d, J=7.0 Hz, 1H), 7.51 (d, J=9.1 Hz, 1H), 7.45-7.40 (m, 2H), 7.34 (s, 1H), 7.30 (t, J=8.2 Hz, 1H), 7.23-7.18 (m, 1H), 7.06-7.01 (m, 2H), 6.93-6.86 (m, 1H), 6.74 (d, J=8.3 Hz, 1H), 6.62-6.53 (m, 2H), 4.08 (t, J=8.4 Hz, 2H), 3.99 (t, J=5.3 Hz, 2H), 3.72 (t, J=6.5 Hz, 2H), 2.81-2.71 (m, 1H), 2.09-1.99 (m, 2H).

Example 43

3-{2-[3-(4-Chloro-phenoxy)-phenoxy]-ethyl}-azetidine-1-carboxylic acid benzo[d]isoxazol-3-ylamide

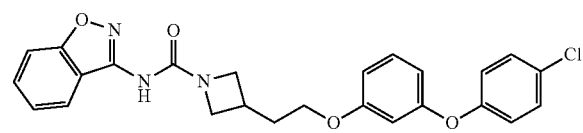 [SMILES: O=C(Nc1noc2ccccc12)N1CC(CCOc2cccc(Oc3ccc(Cl)cc3)c2)C1]

MS (ESI$^+$): calcd. for $C_{25}H_{22}ClN_3O_4$, 463.13. m/z found, 464.1 (M+H)$^+$. $^1$H NMR (d$_6$-DMSO): 9.70 (s, 1H), 7.99 (d, J=8.1 Hz, 1H), 7.64-7.56 (m, 2H), 7.43 (d, J=8.8 Hz, 2H), 7.32-7.26 (m, 2H), 7.04 (d, J=8.8 Hz, 2H), 6.75 (dd, J=8.3, 2.3 Hz, 1H), 6.61 (t, J=2.3 Hz, 1H), 6.57 (dd, J=8.0, 2.2 Hz, 1H), 4.15 (t, J=8.0 Hz, 2H), 3.99 (t, J=6.1 Hz, 2H), 3.79 (t, J=5.8 Hz, 2H), 2.82-2.71 (m, 1H), 2.08-1.98 (m, 2H).

Example 44

3-{2-[3-(4-Chloro-phenoxy)-phenoxy]-ethyl}-azetidine-1-carboxylic acid pyridin-3-ylamide

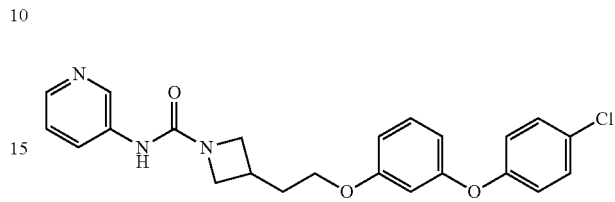

MS (ESI$^+$): calcd. for $C_{23}H_{22}ClN_3O_3$, 423.13. m/z found, 424.2 (M+H)$^+$. $^1$H NMR (d$_6$-DMSO): 8.65 (d, J=2.4 Hz, 1H), 8.56 (s, 1H), 8.13 (dd, J=4.6, 1.4 Hz, 1H), 7.93-7.88 (m, 1H), 7.43 (d, J=8.9 Hz, 2H), 7.30 (t, J=8.2 Hz, 1H), 7.25 (dd, J=8.3, 4.6 Hz, 1H), 7.04 (d, J=8.9 Hz, 2H), 6.78-6.71 (m, 1H), 6.63-6.55 (m, 2H), 4.08 (t, J=8.2 Hz, 2H), 3.98 (t, J=6.1 Hz, 2H), 3.73-3.65 (m, 2H), 2.78-2.66 (m, 1H), 2.05-1.96 (m, 2H).

Example 45

3-[2-(4-Chloro-3-trifluoromethyl-phenoxy)-ethyl]-azetidine-1-carboxylic acid pyridin-3-ylamide

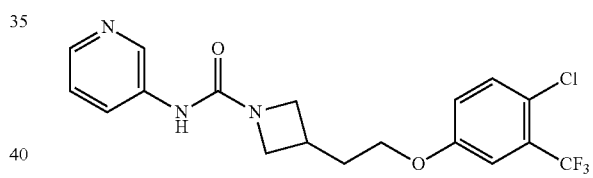

MS (ESI$^+$): calcd. for $C_{18}H_{17}ClF_3N_3O_2$, 399.10. m/z found, 400.1 (M+H)$^+$. $^1$H NMR (d$_6$-DMSO): 8.66 (d, J=2.2 Hz, 1H), 8.57 (s, 1H), 8.13 (dd, J=4.6, 1.4 Hz, 1H), 7.95-7.89 (m, 1H), 7.63 (d, J=8.9 Hz, 1H), 7.33 (d, J=2.9 Hz, 1H), 7.29-7.23 (m, 2H), 4.13-4.04 (m, 4H), 3.72 (dd, J=8.1, 5.9 Hz, 2H), 2.80-2.70 (m, 1H), 2.09-2.00 (m, 2H).

Example 46

3-[2-(3-Trifluoromethyl-phenoxy)-ethyl]-azetidine-1-carboxylic acid pyridin-3-ylamide

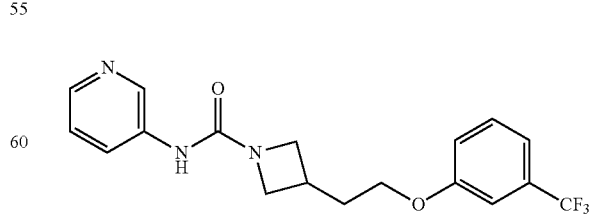

MS (ESI$^+$): calcd. for $C_{18}H_{18}F_3N_3O_2$, 365.14. m/z found, 366.2 (M+H)$^+$. $^1$H NMR (d$_6$-DMSO): 8.66 (d, J=2.2 Hz, 1H), 8.56 (s, 1H), 8.13 (dd, J=4.6, 1.4 Hz, 1H), 7.95-7.89 (m, 1H), 7.53 (t, J=8.0 Hz, 1H), 7.31-7.19 (m, 4H), 4.14-4.03 (m, 4H), 3.73 (dd, J=8.1, 5.9 Hz, 2H), 2.82-2.69 (m, 1H), 2.09-2.01 (m, 2H).

Example 47

3-[2-(3,5-Dichloro-phenoxy)-ethyl]-azetidine-1-carboxylic acid pyridin-3-ylamide

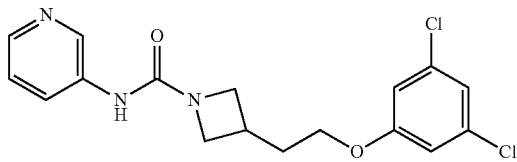 [SMILES: O=C(Nc1cccnc1)N1CC(CCOc2cc(Cl)cc(Cl)c2)C1]

MS (ESI+): calcd. for $C_{17}H_{17}Cl_2N_3O_2$, 365.07. m/z found, 366.1 (M+H)+. 1H NMR ($d_6$-DMSO): 8.66 (d, J=2.2 Hz, 1H), 8.56 (s, 1H), 8.13 (dd, J=4.6, 1.4 Hz, 1H), 7.94-7.89 (m, 1H), 7.25 (dd, J=8.2, 4.6 Hz, 1H), 7.15 (t, J=1.8 Hz, 1H), 7.04 (d, J=1.8 Hz, 2H), 4.11-4.01 (m, 4H), 3.71 (dd, J=8.2, 5.9 Hz, 2H), 2.77-2.68 (m, 1H), 2.05-1.98 (m, 2H).

Example 48

3-{2-[3-(5-Chloro-pyridin-2-yloxy)-phenoxy]-ethyl}-azetidine-1-carboxylic acid (4-chloro-pyridin-3-yl)-amide

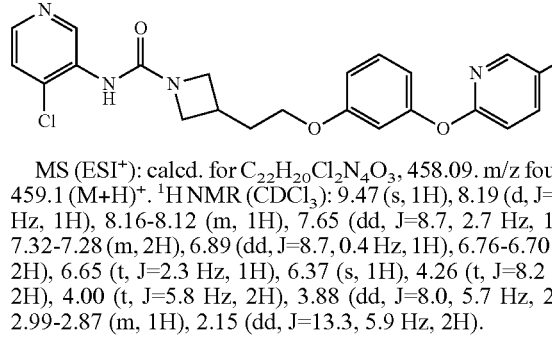

MS (ESI+): calcd. for $C_{22}H_{20}Cl_2N_4O_3$, 458.09. m/z found, 459.1 (M+H)+. 1H NMR (CDCl3): 9.47 (s, 1H), 8.19 (d, J=5.2 Hz, 1H), 8.16-8.12 (m, 1H), 7.65 (dd, J=8.7, 2.7 Hz, 1H), 7.32-7.28 (m, 2H), 6.89 (dd, J=8.7, 0.4 Hz, 1H), 6.76-6.70 (m, 2H), 6.65 (t, J=2.3 Hz, 1H), 6.37 (s, 1H), 4.26 (t, J=8.2 Hz, 2H), 4.00 (t, J=5.8 Hz, 2H), 3.88 (dd, J=8.0, 5.7 Hz, 2H), 2.99-2.87 (m, 1H), 2.15 (dd, J=13.3, 5.9 Hz, 2H).

Examples 49 to 64 were prepared using methods analogous to those described for Example 1, using the appropriate carbamate, hydroxypyrrolidine-1-carboxylic acid tert-butyl ester and phenol.

Example 49

N-(4-Chloropyridin-3-yl)-3-[(3,4-dichlorophenoxy)methyl]pyrrolidine-1-carboxamide

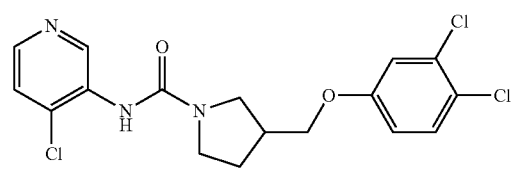 [SMILES: O=C(Nc1cnccc1Cl)N1CCC(COc2ccc(Cl)c(Cl)c2)C1]

MS (ESI): mass calcd. for $C_{17}H_{16}Cl_3N_3O_2$, 399.03. m/z found, 400.1 [M+H]+. 1H NMR (CD3OD): 8.79 (s, 1H), 8.24 (d, J=5.3 Hz, 1H), 7.54 (d, J=5.3 Hz, 1H), 7.40 (d, J=8.9 Hz, 1H), 7.24-7.05 (m, 1H), 6.91 (dd, J=8.9, 2.9 Hz, 1H), 4.14-4.04 (m, 1H), 4.04-3.95 (m, 1H), 3.82-3.72 (m, 1H), 3.72-3.63 (m, 1H), 3.63-3.48 (m, 1H), 3.48-3.37 (m, 1H), 2.88-2.73 (m, 1H), 2.30-2.17 (m, 1H), 2.03-1.90 (m, 1H).

Example 50

N-(4-Chloropyridin-3-yl)-3-({3-[4-(methylsulfonyl)phenoxy]phenoxy}methyl)pyrrolidine-1-carboxamide

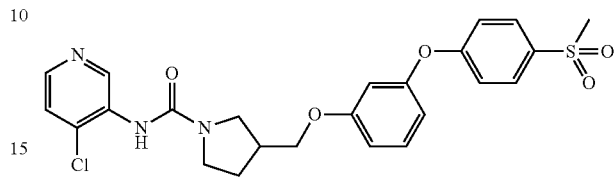

MS (ESI): mass calcd. for $C_{24}H_{24}ClN_3O_5S$, 501.11. m/z found, 502.1 [M+H]+. 1H NMR (CD3OD): 8.93-8.66 (m, 1H), 8.35-8.16 (m, 1H), 7.91 (d, J=8.8 Hz, 2H), 7.62-7.44 (m, 1H), 7.44-7.25 (m, 1H), 7.24-7.06 (m, 2H), 6.94-6.79 (m, 1H), 6.78-6.60 (m, 2H), 4.16-3.95 (m, 2H), 3.83-3.63 (m, 2H), 3.64-3.51 (m, 2H), 3.16-3.04 (m, 3H), 2.91-2.72 (m, 1H), 2.33-2.13 (m, 1H), 2.04-1.76 (m, 1H).

Example 51

3-{[3-(4-Chlorophenoxy)phenoxy]methyl}-N-pyridin-3-ylpyrrolidine-1-carboxamide

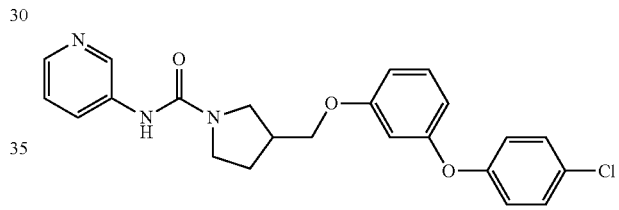

MS (ESI): mass calcd. for $C_{23}H_{22}ClN_3O_3$, 423.13. m/z found, 424.2 [M+H]+. 1H NMR (CD3OD): 8.73-8.58 (m, 1H), 8.26-8.09 (m, 1H), 8.09-7.92 (m, 1H), 7.47-7.19 (m, 4H), 7.16-6.91 (m, 3H), 6.87-6.68 (m, 1H), 6.64-6.50 (m, 1H), 4.11-3.86 (m, 2H), 3.84-3.61 (m, 2H), 3.58-3.46 (m, 2H), 2.92-2.72 (m, 1H), 2.26-2.08 (m, 1H), 2.04-1.77 (m, 1H).

Example 52

3-({3-[4-(Methylsulfonyl)phenoxy]phenoxy}methyl)-N-pyridin-3-ylpyrrolidine-1-carboxamide

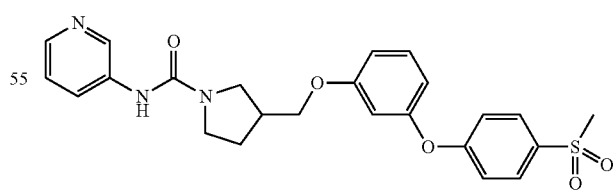

MS (ESI): mass calcd. for $C_{24}H_{25}N_3O_5S$, 467.15. m/z found, 468.2 [M+H]+. 1H NMR (CD3OD): 8.65 (d, J=2.5 Hz, 1H), 8.18 (dd, J=4.8, 1.4 Hz, 1H), 8.04-7.85 (m, 3H), 7.46-7.25 (m, 2H), 7.23-7.08 (m, 2H), 6.88 (dd, J=7.9, 1.9 Hz, 1H), 6.82-6.60 (m, 2H), 4.14-3.95 (m, 2H), 3.82-3.63 (m, 2H), 3.59-3.37 (m, 2H), 3.18-3.08 (m, 3H), 2.88-2.75 (m, 1H), 2.29-2.15 (m, 1H), 2.02-1.87 (m, 1H).

Example 53

3-[2-(3,4-Dichloro-phenoxy)-ethyl]-pyrrolidine-1-carboxylic acid pyridin-3-ylamide

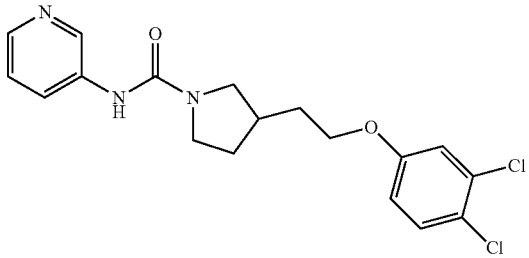 [SMILES: O=C(Nc1cccnc1)N1CCC(CCOc2ccc(Cl)c(Cl)c2)C1]

MS (ESI+): calcd. for $C_{18}H_{19}Cl_2N_3O_2$, 379.09. m/z found, 380.1 (M+H)+. $^1$H NMR (CDCl$_3$): 8.44 (d, J=2.5 Hz, 1H), 8.26 (dd, J=4.7, 1.3 Hz, 1H), 8.06 (ddd, J=8.3, 2.5, 1.4 Hz, 1H), 7.33 (d, J=8.9 Hz, 1H), 7.23 (dd, J=8.3, 4.7 Hz, 1H), 6.99 (d, J=2.8 Hz, 1H), 6.75 (dd, J=8.9, 2.9 Hz, 1H), 6.26 (s, 1H), 4.00 (t, J=6.1 Hz, 2H), 3.79-3.71 (m, 1H), 3.67-3.58 (m, 1H), 3.45 (td, J=9.4, 7.1 Hz, 1H), 3.14 (t, J=9.2 Hz, 1H), 2.54-2.41 (m, 1H), 2.25-2.17 (m, 1H), 1.93 (dd, J=13.0, 6.3 Hz, 2H), 1.79-1.68 (m, 1H).

Example 54

3-(2-Phenoxy-ethyl)-pyrrolidine-1-carboxylic acid pyridin-3-ylamide

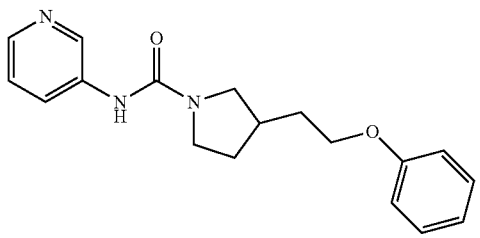 [SMILES: O=C(Nc1cccnc1)N1CCC(CCOc2ccccc2)C1]

MS (ESI+): calcd. for $C_{18}H_{21}N_3O_2$, 311.16. m/z found, 312.2 (M+H)+. $^1$H NMR (CDCl$_3$): 8.44 (d, J=2.3 Hz, 1H), 8.26 (dd, J=4.7, 1.4 Hz, 1H), 8.07 (ddd, J=8.3, 2.6, 1.4 Hz, 1H), 7.29 (dd, J=8.7, 7.4 Hz, 2H), 7.23 (dd, J=8.4, 4.7 Hz, 1H), 6.96 (t, J=7.4 Hz, 1H), 6.90 (dd, J=8.7, 0.9 Hz, 2H), 6.22 (s, 1H), 4.04 (t, J=6.1 Hz, 2H), 3.79-3.73 (m, 1H), 3.67-3.60 (m, 1H), 3.45 (td, J=9.5, 7.0 Hz, 1H), 3.15 (t, J=9.1 Hz, 1H), 2.58-2.47 (m, 1H), 2.25-2.17 (m, 1H), 1.95 (dd, J=13.1, 6.2 Hz, 2H), 1.78-1.68 (m, 1H).

Example 55

(3S)-3-[3-(4-Chloro-phenoxy)-phenoxymethyl]-pyrrolidine-1-carboxylic acid (4-chloro-pyridin-3-yl)-amide

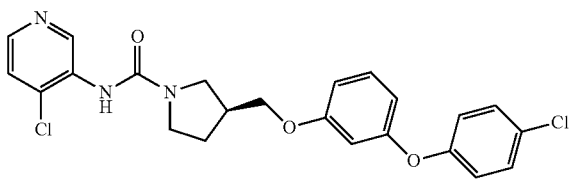 [SMILES: O=C(Nc1cnccc1Cl)N1CC[C@H](COc2cccc(Oc3ccc(Cl)cc3)c2)C1]

MS (ESI+): calcd. for $C_{23}H_{21}Cl_2N_3O_3$, 457.10. m/z found, 458.1 (M+H)+. $^1$H NMR (CDCl$_3$): 9.49 (s, 1H), 8.19 (d, J=5.2, 1H), 7.31-7.28 (m, 3H), 7.24 (t, J=8.2, 1H), 6.95 (d, J=8.9, 2H), 6.68-6.65 (m, 2H), 6.61-6.58 (m, 1H), 6.54 (t, J=2.3, 1H), 3.98 (dd, J=9.1, 6.2, 1H), 3.93 (dd, J=9.2, 7.1, 1H), 3.77 (dd, J=9.7, 7.7, 1H), 3.72-3.65 (m, 1H), 3.60-3.54 (m, 1H), 3.43 (dd, J=9.9, 6.9, 1H), 2.88-2.77 (m, 1H), 2.28-2.16 (m, 1H), 2.03-1.92 (m, 1H).

Example 56

(3R)-3-[3-(4-Chloro-phenoxy)-phenoxymethyl]-pyrrolidine-1-carboxylic acid (4-chloro-pyridin-3-yl)-amide

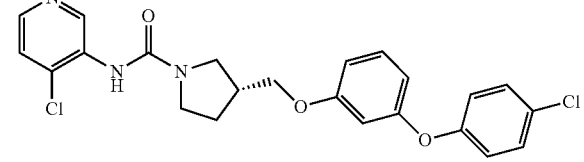

MS (ESI+): calcd. for $C_{23}H_{21}Cl_2N_3O_3$, 457.10. m/z found, 458.1 (M+H)+. $^1$H NMR (CDCl$_3$): 9.49 (s, 1H), 8.19 (d, J=5.2, 1H), 7.31-7.27 (m, 3H), 7.24 (t, J=8.2, 1H), 6.95 (d, J=8.9, 2H), 6.68-6.64 (m, 2H), 6.61-6.58 (m, 1H), 6.54 (t, J=2.3, 1H), 3.98 (dd, J=9.1, 6.2, 1H), 3.93 (dd, J=9.1, 7.1, 1H), 3.77 (dd, J=9.6, 7.7, 1H), 3.71-3.65 (m, 1H), 3.60-3.54 (m, 1H), 3.43 (dd, J=9.9, 6.9, 1H), 2.87-2.78 (m, 1H), 2.27-2.18 (m, 1H), 2.02-1.93 (m, 1H).

Example 57

3-(2-Phenoxy-ethyl)-pyrrolidine-1-carboxylic acid (4-chloropyridin-3-yl)-amide

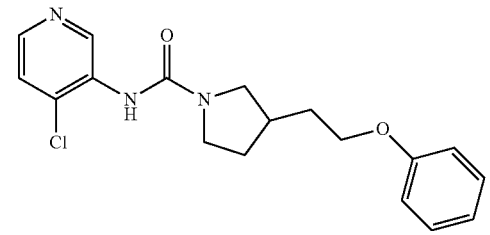 [SMILES: O=C(Nc1cnccc1Cl)N1CCC(CCOc2ccccc2)C1]

MS (ESI+): calcd. for $C_{18}H_{20}ClN_3O_2$, 345.12. m/z found, 346.2 (M+H)+. $^1$H NMR (CDCl$_3$): 9.51 (s, 1H), 8.18 (d, J=5.2 Hz, 1H), 7.32-7.27 (m, 3H), 6.96 (t, J=7.4 Hz, 1H), 6.90 (dd, J=8.7, 0.9 Hz, 2H), 6.66 (s, 1H), 4.10-4.00 (m, 2H), 3.84-3.75 (m, 1H), 3.71-3.63 (m, 1H), 3.48 (td, J=9.5, 7.0 Hz, 1H), 3.19 (t, J=9.2 Hz, 1H), 2.59-2.47 (m, 1H), 2.28-2.19 (m, 1H), 1.96 (dd, J=12.4, 6.4 Hz, 2H), 1.81-1.70 (m, 1H).

Example 58

3-[2-(3,4-Dichloro-phenoxy)-ethyl]-pyrrolidine-1-carboxylic acid (4-chloropyridin-3-yl)-amide

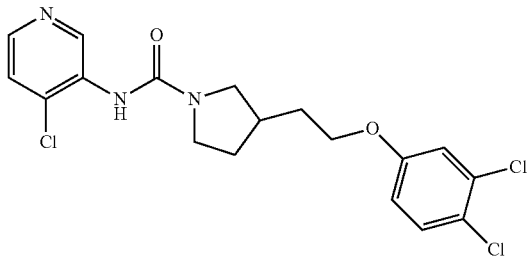 [SMILES: O=C(Nc1cnccc1Cl)N1CCC(CCOc2ccc(Cl)c(Cl)c2)C1]

MS (ESI+): calcd. for $C_{18}H_{18}Cl_3N_3O_2$, 413.05. m/z found, 414.1 (M+H)+. $^1$H NMR (CDCl$_3$): 9.50 (s, 1H), 8.19 (d, J=5.2

Hz, 1H), 7.33 (d, J=8.9 Hz, 1H), 7.29 (d, J=5.2 Hz, 1H), 6.99 (d, J=2.8 Hz, 1H), 6.75 (dd, J=8.9, 2.9 Hz, 1H), 6.65 (s, 1H), 4.06-3.96 (m, 2H), 3.83-3.76 (m, 1H), 3.71-3.63 (m, 1H), 3.48 (td, J=9.4, 7.2 Hz, 1H), 3.18 (t, J=9.2 Hz, 1H), 2.56-2.44 (m, 1H), 2.27-2.19 (m, 1H), 1.95 (dd, J=12.6, 6.3 Hz, 2H), 1.81-1.70 (m, 1H).

Example 59

3-[2-(3-Trifluoromethoxy-phenoxy)-ethyl]-pyrrolidine-1-carboxylic acid pyridin-3-ylamide

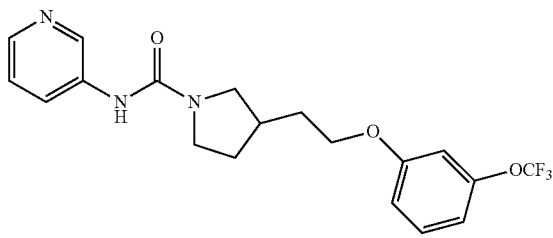 [SMILES: O=C(Nc1cccnc1)N1CCC(CCOc2cccc(OC(F)(F)F)c2)C1]

MS (ESI$^+$): calcd. for $C_{19}H_{20}F_3N_3O_3$, 395.15. m/z found, 396.2 (M+H)$^+$. $^1$H NMR (CDCl$_3$): 8.44 (d, J=2.3 Hz, 1H), 8.26 (dd, J=4.7, 1.4 Hz, 1H), 8.06 (ddd, J=8.4, 2.6, 1.5 Hz, 1H), 7.29 (t, J=8.3 Hz, 1H), 7.22 (dd, J=8.4, 4.7 Hz, 1H), 6.82 (dd, J=8.3, 2.3 Hz, 2H), 6.76-6.73 (m, 1H), 6.23 (s, 1H), 4.03 (t, J=6.1 Hz, 2H), 3.77 (dd, J=9.4, 7.6 Hz, 1H), 3.64 (td, J=9.4, 2.8 Hz, 1H), 3.46 (td, J=9.4, 7.0 Hz, 1H), 3.19-3.12 (m, 1H), 2.57-2.44 (m, 1H), 2.26-2.16 (m, 1H), 1.95 (dd, J=13.1, 6.2 Hz, 2H), 1.80-1.68 (m, 1H).

Example 60

3-[2-(4-Trifluoromethoxy-phenoxy)-ethyl]-pyrrolidine-1-carboxylic acid pyridin-3-ylamide

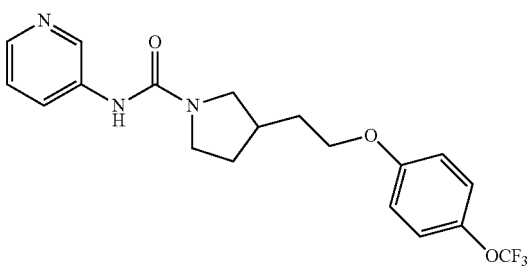 [SMILES: O=C(Nc1cccnc1)N1CCC(CCOc2ccc(OC(F)(F)F)cc2)C1]

MS (ESI$^+$): calcd. for $C_{19}H_{20}F_3N_3O_3$, 395.15. m/z found, 396.2 (M+H)$^+$. $^1$H NMR (CDCl$_3$): 8.44 (d, J=2.3 Hz, 1H), 8.26 (dd, J=4.7, 1.4 Hz, 1H), 8.07 (ddd, J=8.4, 2.6, 1.5 Hz, 1H), 7.23 (dd, J=8.4, 4.7 Hz, 1H), 7.15 (dd, J=9.0, 0.7 Hz, 2H), 6.88 (d, J=9.1 Hz, 2H), 6.18 (s, 1H), 4.03 (t, J=6.1 Hz, 2H), 3.77 (dd, J=9.3, 7.7 Hz, 1H), 3.68-3.61 (m, 1H), 3.46 (td, J=9.4, 7.0 Hz, 1H), 3.19-3.12 (m, 1H), 2.58-2.43 (m, 1H), 2.27-2.16 (m, 1H), 1.95 (dd, J=13.1, 6.2 Hz, 2H), 1.80-1.67 (m, 1H).

Example 61

3-[2-(3-Trifluoromethoxy-phenoxy)-ethyl]-pyrrolidine-1-carboxylic acid (4-chloro-pyridin-3-yl)-amide

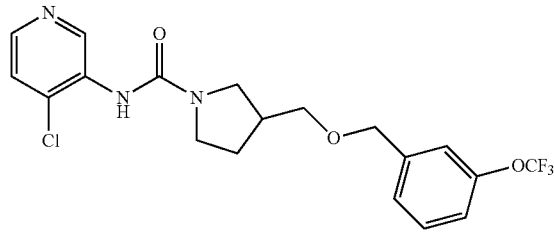 [SMILES: O=C(Nc1cnccc1Cl)N1CCC(COCc2cccc(OC(F)(F)F)c2)C1]

MS (ESI$^+$): calcd. for $C_{19}H_{19}ClF_3N_3O_3$, 429.11. m/z found, 430.2 (M+H)$^+$. $^1$H NMR (CDCl$_3$): 9.50 (s, 1H), 8.18 (d, J=5.2 Hz, 1H), 7.31-7.26 (m, 2H), 6.82 (dd, J=8.3, 2.3 Hz, 2H), 6.76-6.73 (m, 1H), 6.65 (s, 1H), 4.04 (t, J=6.1 Hz, 2H), 3.83-3.76 (m, 1H), 3.71-3.63 (m, 1H), 3.49 (td, J=9.5, 7.0 Hz, 1H), 3.23-3.14 (m, 1H), 2.59-2.44 (m, 1H), 2.30-2.18 (m, 1H), 1.96 (dd, J=12.8, 6.4 Hz, 2H), 1.83-1.70 (m, 1H).

Example 62

3-[2-(4-Trifluoromethoxy-phenoxy)-ethyl]-pyrrolidine-1-carboxylic acid (4-chloro-pyridin-3-yl)-amide

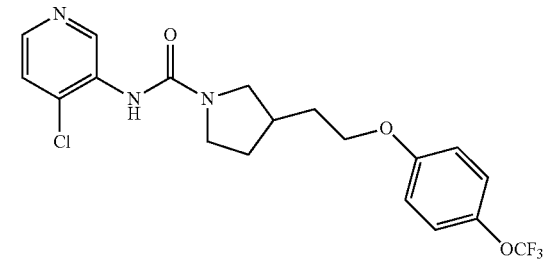 [SMILES: O=C(Nc1cnccc1Cl)N1CCC(CCOc2ccc(OC(F)(F)F)cc2)C1]

MS (ESI$^+$): calcd. for $C_{19}H_{19}ClF_3N_3O_3$, 429.11. m/z found, 430.2 (M+H)$^+$. $^1$H NMR (CDCl$_3$): 9.50 (s, 1H), 8.18 (d, J=5.2 Hz, 1H), 7.28 (d, J=5.2 Hz, 1H), 7.15 (d, J=8.6 Hz, 2H), 6.88 (d, J=8.7 Hz, 2H), 6.64 (s, 1H), 4.03 (t, J=5.8 Hz, 2H), 3.80 (t, J=8.5 Hz, 1H), 3.67 (t, J=7.9 Hz, 1H), 3.48 (dd, J=16.9, 9.0 Hz, 1H), 3.19 (t, J=9.1 Hz, 1H), 2.59-2.43 (m, 1H), 2.29-2.17 (m, 1H), 2.01-1.90 (m, 2H), 1.83-1.69 (m, 1H).

Example 63

3-{2-[3-(4-Chloro-phenoxy)-phenoxy]-ethyl}-pyrrolidine-1-carboxylic acid pyridin-3-ylamide

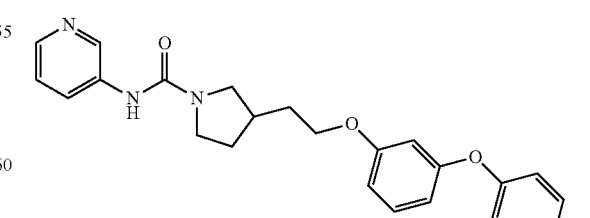

MS (ESI$^+$): calcd. for $C_{24}H_{24}ClN_3O_3$, 437.15. m/z found, 438.2 (M+H)$^+$. $^1$H NMR (CDCl$_3$): 8.43 (d, J=2.5 Hz, 1H), 8.26 (dd, J=4.7, 1.3 Hz, 1H), 8.07 (ddd, J=8.4, 2.5, 1.5 Hz, 1H), 7.29 (d, J=8.9 Hz, 2H), 7.25-7.20 (m, 2H), 6.96 (d, J=8.9 Hz, 2H), 6.66 (dd, J=8.2, 1.8 Hz, 1H), 6.58 (dd, J=8.1, 1.7 Hz, 1H), 6.54 (t, J=2.3 Hz, 1H), 6.16 (s, 1H), 4.00 (t, J=6.1 Hz, 2H), 3.76 (t, J=8.4 Hz, 1H), 3.62 (d, J=9.0 Hz, 1H), 3.45 (td, J=9.4, 7.1 Hz, 1H), 3.14 (t, J=9.1 Hz, 1H), 2.56-2.44 (m, 1H), 2.25-2.16 (m, 1H), 1.93 (dd, J=13.0, 6.2 Hz, 2H), 1.78-1.68 (m, 1H).

Example 64

3-{2-[3-(4-Chloro-phenoxy)-phenoxy]-ethyl}-pyrrolidine-1-carboxylic acid (4-chloro-pyridin-3-yl)-amide

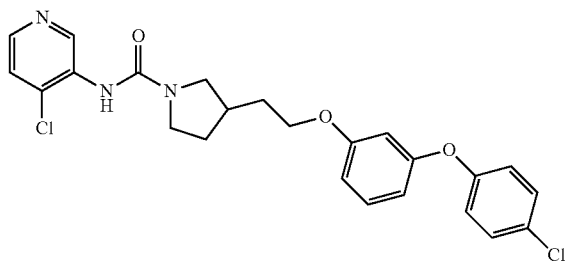 [SMILES: O=C(Nc1cnccc1Cl)N1CCC(CCOc2cccc(Oc3ccc(Cl)cc3)c2)C1]

MS (ESI+): calcd. for $C_{24}H_{23}Cl_2N_3O_3$, 471.11. m/z found, 472.2 (M+H)+. 1H NMR (CDCl3): 9.50 (s, 1H), 8.18 (d, J=5.2 Hz, 1H), 7.32-7.26 (m, 3H), 7.23 (t, J=8.2 Hz, 1H), 6.98-6.93 (m, 2H), 6.68-6.62 (m, 2H), 6.58 (ddd, J=8.1, 2.3, 0.8 Hz, 1H), 6.54 (dd, J=3.5, 1.2 Hz, 1H), 4.01 (t, J=6.1 Hz, 2H), 3.84-3.74 (m, 1H), 3.67 (td, J=9.7, 2.4 Hz, 1H), 3.47 (td, J=9.5, 7.0 Hz, 1H), 3.21-3.12 (m, 1H), 2.59-2.44 (m, 1H), 2.27-2.16 (m, 1H), 1.99-1.88 (m, 2H), 1.82-1.68 (m, 1H).

Example 65

3-[2-(4-Chloro-benzyloxy)-ethyl]-azetidine-1-carboxylic acid (4-chloro-pyridin-3-yl)-amide

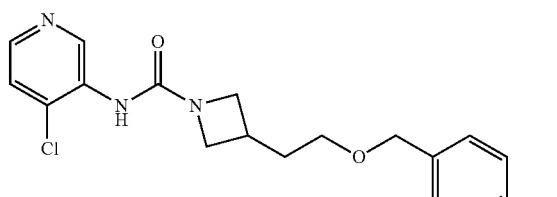

Step A: 3-[2-(4-Chloro-benzyloxy)-ethyl]-azetidine-1-carboxylic acid tert-butyl ester To a solution consisting of 3-(2-hydroxy-ethyl)-azetidine-1-carboxylic acid tert-butyl ester (0.250 g, 1.24 mmol) and THF (2 mL) at 0° C. was added sodium hydride (0.0459 g, 0.124 mmol). The reaction was stirred at 0° C. for 0.5 h, then treated with tetrabutylammonium iodide (0.0459 g, 0.124 mmol) and 4-chlorobenzyl bromide (0.383 g, 1.86 mmol), warmed to rt and stirred for 16 h. The reaction was quenched with saturated aqueous NH4Cl (1.0 mL), diluted with ethyl acetate (40 mL) and extracted with 1 N NaOH (40 mL). The organic layer was dried (MgSO4) and concentrated. The residue was purified (FCC) to give the title compound as a yellow oil (0.302 g, 74%). 1H NMR (d6-DMSO): 7.40 (d, J=8.4 Hz, 2H), 7.32 (d, J=8.4 Hz, 2H), 4.42 (s, 2H), 3.88 (t, J=8.0 Hz, 2H), 3.53-3.44 (m, 2H), 3.40 (t, J=6.2 Hz, 2H), 2.62-2.53 (m, 1H), 1.84-1.74 (m, 2H), 1.36 (s, 9H).

Step B: 3-[2-(4-chloro-benzyloxy)-ethyl]-azetidine, formic acid salt

The title compound was prepared using methods analogous to those described for Example 1 step B. MS (ESI+): calcd. for $C_{12}H_{16}ClN_0$, 225.09. m/z found, 226.1 (M+H)+. 1H NMR (d6-DMSO): 8.42 (s, 1H), 7.40 (d, J=8.4 Hz, 2H), 7.32 (d, J=8.4 Hz, 2H), 4.42 (s, 2H), 3.86 (dd, J=10.2, 8.7 Hz, 2H), 3.63-3.54 (m, 2H), 3.41 (t, J=6.1 Hz, 2H), 2.89-2.77 (m, 1H), 1.88-1.80 (m, 2H).

Step C: 3-[2-(4-Chloro-benzyloxy)-ethyl]-azetidine-1-carboxylic acid (4-chloro-pyridin-3-yl)-amide The title compound was prepared using methods analogous to those described for Example 1 step C. MS (ESI+): calcd. for $C_{18}H_{19}Cl_2N_3O_2$, 379.09. m/z found, 380.1 (M+H)+. 1H NMR (d6-DMSO): 8.70 (s, 1H), 8.25 (d, J=5.2 Hz, 1H), 8.09 (s, 1H), 7.54 (d, J=5.3 Hz, 1H), 7.41 (d, J=8.5 Hz, 2H), 7.34 (d, J=8.5 Hz, 2H), 4.45 (s, 2H), 4.06 (t, J=8.2 Hz, 2H), 3.66 (dd, J=8.1, 5.9 Hz, 2H), 3.45 (t, J=6.2 Hz, 2H), 2.74-2.62 (m, 1H), 1.86 (dd, J=13.6, 6.2 Hz, 2H).

Examples 66 to 70 were prepared using methods analogous to those described for Example 65, using the appropriate carbamate and benzyl bromide.

Example 66

3-[2-(4-Chloro-benzyloxy)-ethyl]-azetidine-1-carboxylic acid pyridin-3-ylamide, trifluoroacetate salt

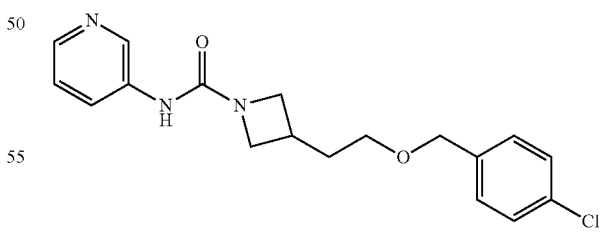

MS (ESI+): calcd. for $C_{18}H_{20}ClN_3O_2$, 345.12. m/z found, 346.2 (M+H)+.

1H NMR (d6-DMSO): 9.13 (s, 1H), 8.99 (d, J=1.7 Hz, 1H), 8.39 (d, J=5.0 Hz, 1H), 8.34-8.27 (m, 1H), 7.75 (dd, J=8.6, 5.3 Hz, 1H), 7.41 (d, J=8.5 Hz, 2H), 7.34 (d, J=8.5 Hz, 2H), 4.45 (s, 2H), 4.09 (t, J=8.3 Hz, 2H), 3.69 (dd, J=8.3, 5.8 Hz, 2H), 3.45 (t, J=6.1 Hz, 2H), 2.75-2.62 (m, 1H), 1.90-1.82 (m, 2H).

Example 67

3-[2-(3,4-Dichloro-benzyloxy)-ethyl]-azetidine-1-carboxylic acid (4-chloro-pyridin-3-yl)-amide

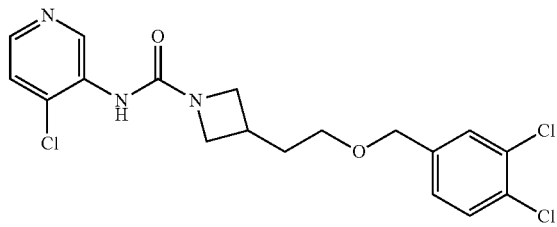 [SMILES: O=C(Nc1cnccc1Cl)N1CC(CCOCc2ccc(Cl)c(Cl)c2)C1]

MS (ESI⁺): calcd. for $C_{18}H_{18}Cl_3N_3O_2$, 413.05. m/z found, 414.1 (M+H)⁺. ¹H NMR (d₆-DMSO): 8.70 (s, 1H), 8.25 (d, J=5.3 Hz, 1H), 8.09 (s, 1H), 7.61 (d, J=8.2 Hz, 1H), 7.56 (d, J=1.8 Hz, 1H), 7.54 (d, J=5.3 Hz, 1H), 7.32 (dd, J=8.3, 1.9 Hz, 1H), 4.47 (s, 2H), 4.06 (t, J=8.2 Hz, 2H), 3.66 (dd, J=8.1, 5.9 Hz, 2H), 3.46 (t, J=6.2 Hz, 2H), 2.75-2.64 (m, 1H), 1.92-1.83 (m, 2H).

Example 68

3-[2-(3,4-Dichloro-benzyloxy)-ethyl]-azetidine-1-carboxylic acid pyridin-3-ylamide, trifluoroacetate salt

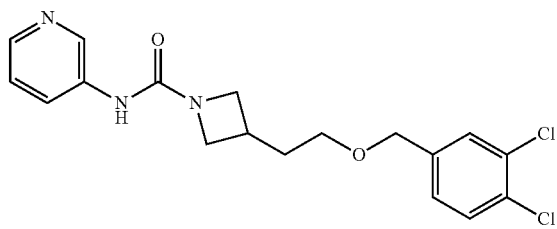 [SMILES: O=C(Nc1cccnc1)N1CC(CCOCc2ccc(Cl)c(Cl)c2)C1]

MS (ESI⁺): calcd. for $C_{19}H_{19}Cl_2N_3O_2$, 379.09. m/z found, 380.1 (M+H)⁺. ¹H NMR (d₆-DMSO): 9.05 (s, 1H), 8.96 (d, J=2.3 Hz, 1H), 8.35 (dd, J=5.2, 1.1 Hz, 1H), 8.28-8.23 (m, 1H), 7.70 (dd, J=8.6, 5.3 Hz, 1H), 7.62 (d, J=8.2 Hz, 1H), 7.56 (d, J=1.9 Hz, 1H), 7.32 (dd, J=8.2, 1.9 Hz, 1H), 4.47 (s, 2H), 4.09 (t, J=8.3 Hz, 2H), 3.68 (dd, J=8.3, 5.9 Hz, 2H), 3.46 (t, J=6.1 Hz, 2H), 2.76-2.65 (m, 1H), 1.88 (d, J=7.3 Hz, 2H).

Example 69

3-(2-Benzyloxy-ethyl)-azetidine-1-carboxylic acid pyridin-3-ylamide

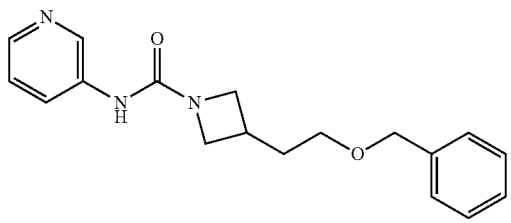 [SMILES: O=C(Nc1cccnc1)N1CC(CCOCc2ccccc2)C1]

MS (ESI⁺): calcd. for $C_{18}H_{21}N_3O_2$, 311.16. m/z found, 312.2 (M+H)⁺. ¹H NMR (d₆-DMSO): 8.65 (d, J=2.5 Hz, 1H), 8.51 (s, 1H), 8.12 (dd, J=4.7, 1.5 Hz, 1H), 7.93-7.89 (m, 1H), 7.39-7.26 (m, 5H), 7.24 (dd, J=8.3, 4.6 Hz, 1H), 4.46 (s, 2H), 4.04 (t, J=8.2 Hz, 2H), 3.64 (dd, J=8.2, 5.8 Hz, 2H), 3.44 (t, J=6.2 Hz, 2H), 2.73-2.60 (m, 1H), 1.90-1.81 (m, 2H).

Example 70

3-(2-Benzyloxy-ethyl)-azetidine-1-carboxylic acid (4-chloropyridin-3-yl)-amide

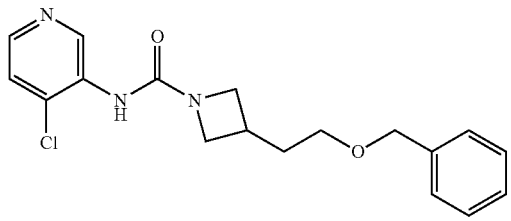 [SMILES: O=C(Nc1cnccc1Cl)N1CC(CCOCc2ccccc2)C1]

MS (ESI⁺): calcd. for $C_{18}H_{20}ClN_3O_2$, 345.12. m/z found, 346.2 (M+H)⁺. ¹H NMR (d₆-DMSO): 8.70 (s, 1H), 8.25 (d, J=5.3 Hz, 1H), 8.09 (s, 1H), 7.53 (d, J=5.3 Hz, 1H), 7.39-7.24 (m, 5H), 4.46 (s, 2H), 4.06 (t, J=8.2 Hz, 2H), 3.66 (dd, J=8.1, 5.9 Hz, 2H), 3.45 (t, J=6.2 Hz, 2H), 2.75-2.62 (m, 1H), 1.91-1.82 (m, 2H).

Example 71

3-(2,2-Difluoro-benzo[1,3]dioxol-5-ylmethyl)-pyrrolidine-1-carboxylic acid pyridin-3-ylamide

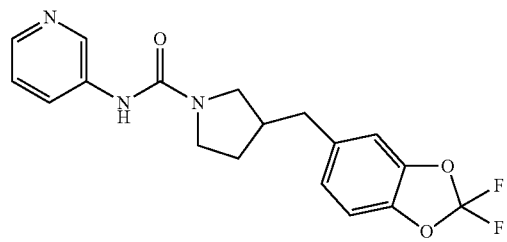 [SMILES: O=C(Nc1cccnc1)N1CCC(Cc2ccc3c(c2)OC(F)(F)O3)C1]

Step A: 3-Methylene pyrrolidine-1-carboxylic acid tert-butyl ester

To a suspension consisting of methyl triphenylphosphonium bromide (18 g, 51 mmol) and THF (200 mL) at 0° C. was added n-butyl lithium (1.6 M solution in hexanes, 32 mL). The resulting orange solution was stirred at 0° C. for 5 min, then a solution of 3-oxo-pyrrolidine-1-carboxylic acid tert-butyl ester (9.0 g, 48 mmol) in THF (40 mL) was added via cannula. The reaction mixture was stirred at 0° C. for 90 min, then warmed to rt and stirring was continued for 1 h. The reaction mixture was then cooled to 0° C., quenched with sat. NH₄Cl, and extracted with Et₂O. The organic layer was dried (MgSO₄) and concentrated. The crude residue was suspended in hot hexanes and filtered. The filtrate was concentrated and purified (FCC) to give the title compound (4.4 g, 50%).

Step B: 3-(2,2-Difluoro-benzo[1,3]dioxol-5-ylmethyl)-pyrrolidine-1-carboxylic acid tert-butyl ester A stream of N₂ was bubbled through neat 3-methylene pyrrolidine-1-carboxylic acid tert-butyl ester (792 mg, 4.33 mmol) for 15 min before charging the flask with 9-BBN (0.5 M in THF, 8.8 mL). The reaction mixture was heated at reflux for 2.5 h; then cooled to rt. The resultant mixture was then added, via cannula, to a preformed solution consisting of 5-bromo-2,2-difluoro-1,3-benzodioxole (1.01 g, 4.24 mmol), Pd(dppf)Cl$_2$·CH$_2$Cl$_2$ (92 mg), and potassium carbonate (760 mg, 5.50 mmol) in DMF/H$_2$O (10 mL/1 mL). The reaction mixture was heated at 60° C. for 18 h, cooled to rt and poured into water. The pH of the mixture was adjusted to 11 with NaOH (1 N), and extracted with EtOAc (3×). The organic layers were combined, dried (Na$_2$SO$_4$), and concentrated. The crude residue was purified (FCC) to give the title compound (1.4 g, 94%).

Step C: 3-(2,2-Difluoro-benzo[1,3]dioxol-5-ylmethyl)-pyrrolidine, hydrochloride salt To a solution consisting of 3-(2,2-difluoro-benzo[1,3]dioxol-5-ylmethyl)-pyrrolidine-1-carboxylic acid tert-butyl ester (1.36 g, 3.98 mmol) and dichloromethane (20 mL) was added HCl (4 M solution in dioxane, 6 mL). The reaction mixture was stirred at rt for 18 h. The resultant mixture was concentrated to give the title compound in quantitative yield.

Step D: 3-(2,2-Difluoro-benzo[1,3]dioxol-5-ylmethyl)-pyrrolidine-1-carboxylic acid pyridin-3-ylamide To a solution consisting of 3-(2,2-difluoro-benzo[1,3]dioxol-5-ylmethyl)-pyrrolidine (111 mg, 0.399 mmol), triethylamine (0.1 mL, 0.72 mmol) and acetonitrile (2 mL) was added pyridin-3-yl-carbamic acid phenyl ester (90.1 mg, 0.421 mmol). The mixture was heated at 35° C. for 18 h, cooled to rt and then concentrated. The crude residue was purified (FCC) to give the title compound (56 mg, 39%). MS (ESI): mass calcd. For C$_{18}$H$_{17}$F$_2$N$_3$O$_3$, 361.12. m/z found, 362.2 [M+H]$^+$. $^1$H NMR (CD$_3$OD): 8.63-8.59 (m, 1H), 8.16-8.13 (m, 1H), 7.97-7.92 (m, 1H), 7.35-7.30 (m, 1H), 7.16-7.09 (m, 2H), 7.06-7.02 (m, 1H), 3.66-3.53 (m, 2H), 3.48-3.38 (m, 1H), 3.19-3.11 (m, 1H), 2.85-2.72 (m, 2H), 2.62-2.50 (m, 1H), 2.11-2.02 (m, 1H), 1.78-1.66 (m, 1H).

Examples 72 to 76 were prepared using methods analogous to those described in Example 71.

Example 72

3-(2,2-Difluoro-benzo[1,3]dioxol-5-ylmethyl)-pyrrolidine-1-carboxylic acid benzo[d]isoxazol-3-ylamide

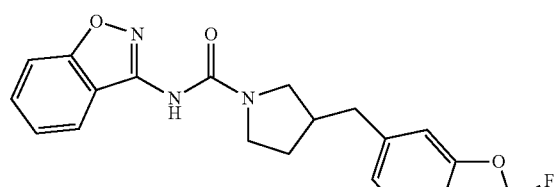

MS (ESI): mass calcd. for C$_{20}$H$_{17}$F$_2$N$_3$O$_4$, 401.12. m/z found, 402.2 [M+H]$^+$. $^1$H NMR (CD$_3$OD): 7.93-7.88 (m, 1H), 7.61-7.48 (m, 2H), 7.33-7.26 (m, 1H), 7.17-7.08 (m, 2H), 7.07-7.02 (m, 1H), 3.74-3.60 (m, 2H), 3.55-3.45 (m, 1H), 3.26-3.16 (m, 1H), 2.86-2.75 (m, 2H), 2.65-2.52 (m, 1H), 2.15-2.03 (m, 1H), 1.81-1.68 (m, 1H).

Example 73

N-2,1,3-Benzoxadiazol-4-yl-3-[(2,2-difluoro-1,3-benzodioxol-5-yl)methyl]pyrrolidine-1-carboxamide

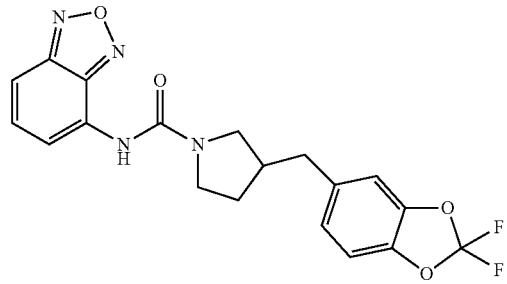 [SMILES: O=C(Nc1cccc2nonc12)N1CCC(Cc2ccc3c(c2)OC(F)(F)O3)C1]

MS (ESI): mass calcd. for C$_{19}$H$_{16}$F$_2$N$_4$O$_4$, 402.11. m/z found, 403.2 [M+H]$^+$. $^1$H NMR (d$_6$-DMSO): 8.55 (s, 1H), 7.71-7.69 (m, 1H), 7.61-7.58 (m, 1H), 7.55-7.51 (m, 1H), 7.36 (d, J=1.5 Hz, 1H), 7.34 (d, J=8.2 Hz, 1H), 7.10 (dd, J=8.2, 1.6 Hz, 1H), 3.66-3.54 (m, 2H), 3.45-3.37 (m, 1H), 3.18-3.09 (m, 1H), 2.75 (d, J=7.5 Hz, 2H), 2.54-2.48 (m, 1H) (coincident with DMSO peak), 2.00-1.92 (m, 1H), 1.67-1.58 (m, 1H).

Example 74

3-[3-(4-Fluoro-phenoxy)-benzyl]-pyrrolidine-1-carboxylic acid pyridin-3-ylamide

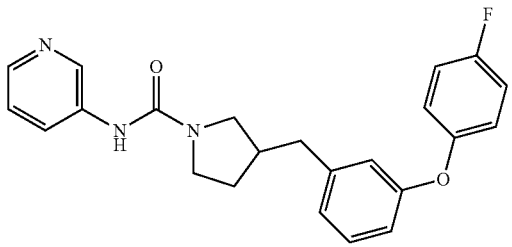 [SMILES: O=C(Nc1cccnc1)N1CCC(Cc2cccc(Oc3ccc(F)cc3)c2)C1]

MS (ESI): mass calcd. for C$_{23}$H$_{22}$FN$_3$O$_2$, 391.17. m/z found, 392.2 [M+H]$^+$. $^1$H NMR (CD$_3$OD): 8.62-8.59 (m, 1H), 8.15 (dd, J=4.8 Hz, 1.4, 1H), 7.94 (ddd, J=8.4, 2.6, 1.5 Hz, 1H), 7.34-7.31 (m, 1H), 7.27 (t, J=7.9 Hz, 1H), 7.10-7.05 (m, 2H), 7.01-6.97 (m, 3H), 6.88-6.86 (m, 1H), 6.81-6.78 (m, 1H), 3.64-3.54 (m, 2H), 3.46-3.40 (m, 1H), 3.15 (dd, J=10.1, 8.0 Hz, 1H), 2.78-2.68 (m, 2H), 2.58-2.52 (m, 1H), 2.09-2.04 (m, 1H), 1.76-1.68 (m, 1H).

Example 75

3-[3-(4-Fluoro-phenoxy)-benzyl]-pyrrolidine-1-carboxylic acid (4-chloro-pyridin-3-yl)-amide

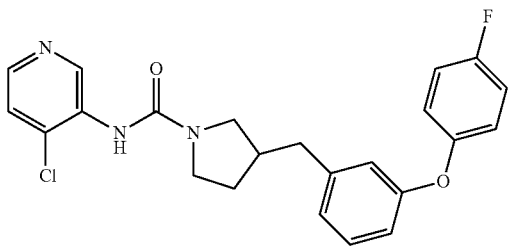 [SMILES: O=C(Nc1cnccc1Cl)N1CCC(Cc2cccc(Oc3ccc(F)cc3)c2)C1]

MS (ESI): mass calcd. for C$_{23}$H$_{21}$ClFN$_3$O$_2$, 425.13. m/z found, 426.2 [M+H]$^+$. $^1$H NMR (CD$_3$OD): 8.77 (s, 1H), 8.24-8.22 (m, 1H), 7.53 (d, J=5.4 Hz, 1H), 7.28 (t, J=7.9 Hz, 1H), 7.10-7.05 (m, 2H), 7.02-6.97 (m, 3H), 6.89-6.87 (m, 1H), 6.81-6.79 (m, 1H), 3.66-3.56 (m, 2H), 3.48-3.43 (m, 1H), 3.21-3.15 (m, 1H), 2.79-2.69 (m, 2H), 2.62-2.53 (m, 1H), 2.12-2.05 (m, 1H), 1.79-1.71 (m, 1H).

Example 76

3-[3-(4-Fluoro-phenoxy)-benzyl]-pyrrolidine-1-carboxylic acid imidazo[1,2-a]pyridine-5-ylamide

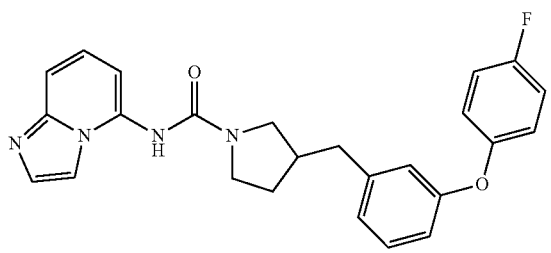 [SMILES: O=C(Nc1cccc2nccn12)N1CCC(Cc2cccc(Oc3ccc(F)cc3)c2)C1]

MS (ESI): mass calcd. for $C_{25}H_{23}FN_4O_2$, 430.18. m/z found, 431.2 [M+H]$^+$. $^1$H NMR (CD$_3$OD): 7.69-7.66 (m, 1H), 7.55 (d, J=1.3 Hz, 1H), 7.45 (d, J=9.0 Hz, 1H), 7.34-7.31 (m, 1H), 7.28 (t, J=7.9 Hz, 1H), 7.10-7.05 (m, 2H), 7.03-6.97 (m, 3H), 6.91-6.88 (m, 1H), 6.82-6.79 (m, 2H), 3.71-3.60 (m, 2H), 3.53-3.45 (m, 1H), 3.24-3.16 (m, 1H), 2.84-2.71 (m, 2H), 2.65-2.53 (m, 1H), 2.15-2.05 (m, 1H), 1.83-1.71 (m, 1H).

Example 77

3-[2-(2,2-Difluoro-benzo[1,3]dioxol-5-yl)-ethyl]-pyrrolidine-1-carboxylic acid pyridin-3-ylamide

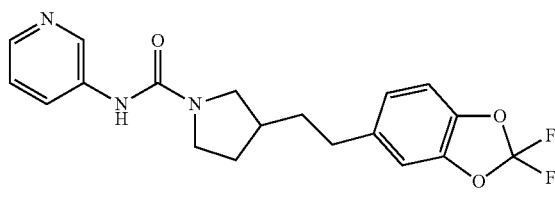 [SMILES: O=C(Nc1cccnc1)N1CCC(CCc2ccc3c(c2)OC(F)(F)O3)C1]

Step A: 3-Vinyl-pyrrolidine-1-carboxylic acid tert-butyl ester

To a suspension consisting of methyl triphenylphosphonium bromide (4.76 g, 13.3 mmol) and THF (20 mL) at 0° C. was added n-butyl lithium (1.6 M solution in hexanes, 8.3 mL). The resulting orange solution was stirred at 0° C. for 5 min. A solution consisting of 3-formyl-pyrrolidine-1-carboxylic acid tert-butyl ester (2.50 g, 12.5 mmol) and THF (15 mL) was then added via cannula. The reaction mixture was stirred at 0° C. and was warmed to rt over 2.5 h. The reaction mixture was then cooled to 0° C., quenched with sat. NH$_4$Cl, and extracted with Et$_2$O. The organic layer was combined, dried (MgSO$_4$) and concentrated. The crude residue was suspended in hot hexanes and filtered. The filtrate was concentrated and purified (FCC) to give the title compound (1.7 g, 70%).

Step B: 3-[2-(2,2-Difluoro-benzo[1,3]dioxol-5-yl)-ethyl]-pyrrolidine-1-carboxylic acid tert-butyl ester A stream of N$_2$ was bubbled through neat 3-vinyl-pyrrolidine-1-carboxylic acid tert-butyl ester (589 mg, 2.99 mmol) for 15 min before adding 9-BBN (0.5 M in THF, 6 mL). The reaction mixture was heated at reflux for 2 h, then cooled to rt. The reaction mixture was then added, via cannula, to a preformed solution consisting of 5-bromo-2,2-difluoro-1,3-benzodioxole (704 mg, 2.97 mmol), Pd(dppf)Cl$_2$.CH$_2$Cl$_2$ (69.7 mg, 0.0953 mmol), and potassium carbonate (559 mg, 4.04 mmol) in DMF/H$_2$O (10 mL/1 mL). The resultant mixture was heated at 60° C. for 18 h, cooled to rt, and poured into water. The pH of the mixture was adjusted to 11 with NaOH (1 N) and extracted with EtOAc (3×). The organic layers were combined, dried (Na$_2$SO$_4$), and concentrated. The crude residue was purified (FCC) to give the title compound (1.0 g, 98%).

Step C: 3-[2-(2,2-Difluoro-benzo[1,3]dioxol-5-yl)-ethyl]-pyrrolidine, hydrochloride salt Title compound was prepared using methods analogous to those described in Example 80, Step C.

Step D: 3-[2-(2,2-Difluoro-benzo[1,3]dioxol-5-yl)-ethyl]-pyrrolidine-1-carboxylic acid pyridin-3-ylamide Title compound was synthesized using procedures analogous to those described in Example 80, Step D. MS (ESI): mass calcd. for $C_{19}H_{19}F_2N_3O_3$, 375.14. m/z found, 376.2 [M+H]$^+$. $^1$H NMR (CD$_3$OD): 8.64-8.61 (m, 1H), 8.16-8.15 (m, 1H), 7.98-7.95 (m, 1H), 7.35-7.32 (m, 1H), 7.12-7.07 (m, 2H), 7.03-7.00 (m, 1H), 3.73-3.69 (m, 1H), 3.64-3.59 (m, 1H), 3.45-3.39 (m, 1H), 3.09 (t, J=9.3 Hz, 1H), 2.75-2.70 (m, 2H), 2.28-2.22 (m, 1H), 2.18-2.12 (m, 1H), 1.80-1.74 (m, 2H), 1.71-1.63 (m, 1H).

Examples 78 to 79 were prepared using methods analogous to those described in Example 77.

Example 78

3-[2-(2,2-Difluoro-benzo[1,3]dioxol-5-yl)-ethyl]-pyrrolidine-1-carboxylic acid (4-chloro-pyridin-3-yl)-amide

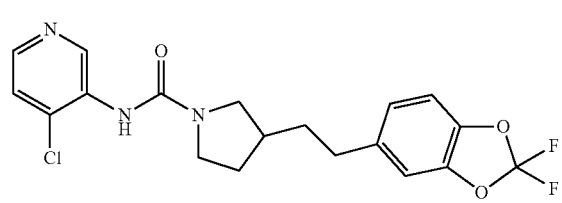 [SMILES: O=C(Nc1cnccc1Cl)N1CCC(CCc2ccc3c(c2)OC(F)(F)O3)C1]

MS (ESI): mass calcd. for $C_{19}H_{18}ClF_2N_3O_3$, 409.10. m/z found, 410.1 [M+H]$^+$. $^1$H NMR (CD$_3$OD): 8.81 (s, 1H), 8.23 (d, J=5.3 Hz, 1H), 7.54 (d, J=5.3 Hz, 1H), 7.12-7.10 (m, 1H), 7.09 (d, J=8.2 Hz, 1H), 7.03-7.01 (m, 1H), 3.72 (dd, J=9.9, 7.5 Hz, 1H), 3.66-3.62 (m, 1H), 3.47-3.42 (m, 1H), 3.13-3.08 (m, 1H), 2.77-2.68 (m, 2H), 2.33-2.23 (m, 1H), 2.21-2.13 (m, 1H), 1.78 (q, J=7.7 Hz, 2H), 1.73-1.66 (m, 1H).

Example 79

3-{2-[3-(4-Fluoro-phenoxy)-phenyl]-ethyl}-pyrrolidine-1-carboxylic acid pyridin-3-ylamide

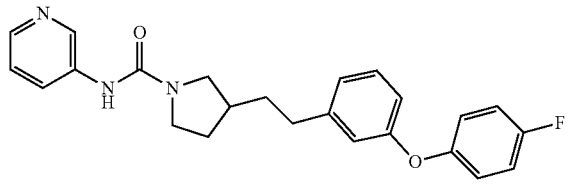 [SMILES: O=C(Nc1cccnc1)N1CCC(CCc2cccc(Oc3ccc(F)cc3)c2)C1]

MS (ESI): mass calcd. for $C_{24}H_{24}FN_3O_2$, 405.19. m/z found, 406.2 [M+H]$^+$. $^1$H NMR (CD$_3$OD): 8.64-8.61 (m, 1H), 8.15 (dd, J=4.8, 1.4 Hz, 1H), 7.96 (ddd, J=8.4, 2.6, 1.5 Hz, 1H), 7.35-7.31 (m, 1H), 7.26 (t, J=7.9 Hz, 1H), 7.10-7.05 (m, 2H), 7.00-6.96 (m, 3H), 6.85-6.83 (m, 1H), 6.79-6.76 (m, 1H), 3.69 (dd, J=10.0, 7.4 Hz, 1H), 3.63-3.58 (m, 1H), 3.43-3.37 (m, 1H), 3.07 (t, J=9.4 Hz, 1H), 2.70-2.65 (m, 2H), 2.27-2.20 (m, 1H), 2.15-2.10 (m, 1H), 1.78-1.73 (m, 2H, 1.69-1.60 (m, 1H).

Biological Testing:

Assay Method 1

A. Transfection of Cells with Human FAAH

A 10-cm tissue culture dish with a confluent monolayer of SK-N-MC cells was split 2 days (d) prior to transfection. Using sterile technique, the media was removed and the cells were detached from the dish by the addition of trypsin. One fifth of the cells were then placed onto a new 10-cm dish. Cells were grown in a 37° C. incubator with 5% CO$_2$ in Minimal Essential Media Eagle with 10% Fetal Bovine Serum. After 2 d, cells were approximately 80% confluent. These cells were removed from the dish with trypsin and pelleted in a clinical centrifuge. The pellet was re-suspended in 400 µL complete media and transferred to an electroporation cuvette with a 0.4 cm gap between the electrodes. Supercoiled human FAAH cDNA (1 µg) was added to the cells and mixed. The voltage for the electroporation was set at 0.25 kV, and the capacitance was set at 960 After electroporation, the cells were diluted into complete media (10 mL) and plated onto four 10-cm dishes. Because of the variability in the efficiency of electroporation, four different concentrations of cells were plated. The ratios used were 1:20, 1:10, and 1:5, with the remainder of the cells being added to the fourth dish. The cells were allowed to recover for 24 h before adding the selection media (complete media with 600 µg/mL G418). After 10 d, dishes were analyzed for surviving colonies of cells. Dishes with well-isolated colonies were used. Cells from individual colonies were isolated and tested. The clones that showed the most FAAH activity, as measured by anandamide hydrolysis, were used for further study.

B. FAAH Assay

T84 frozen cell pellets or transfected SK-N-MC cells (contents of 1×15 cm culture dishes) were homogenized in 50 mL of FAAH assay buffer (125 mM Tris, 1 mM EDTA, 0.2% Glycerol, 0.02% Triton X-100, 0.4 mM Hepes, pH 9). The assay mixture consisted of 50 µL of the cell homogenate, 10 µL of the test compound, and 40 µL of anandamide [1-$^3$H-ethanolamine] ($^3$H-AEA, Perkin-Elmer, 10.3 C$_i$/mmol), which was added last, for a final tracer concentration of 80 nM. The reaction mixture was incubated at rt for 1 h. During the incubation, 96-well Multiscreen filter plates (catalog number MAFCNOB50; Millipore, Bedford, Mass., USA) were loaded with 25 µL of activated charcoal (Multiscreen column loader, catalog number MACL09625, Millipore) and washed once with 100 µL of MeOH. Also during the incubation, 96-well DYNEX MicroLite plates (catalog number NL510410) were loaded with 100 µL of MicroScint40 (catalog number 6013641, Packard Bioscience, Meriden, Conn., USA). After the 1 h incubation, 60 µL of the reaction mixture were transferred to the charcoal plates, which were then assembled on top of the DYNEX plates using Centrifuge Alignment Frames (catalog number MACF09604, Millipore). The unbound labeled ethanolamine was centrifuged through to the bottom plate (5 min at 2000 rpm), which was preloaded with the scintillant, as described above. The plates were sealed and left at rt for 1 h before counting on a Hewlett Packard TopCount.

Assay Method 2

A. Transfection of Cells with Rat FAAH

A 10-cm tissue culture dish with a confluent monolayer of SK-N-MC cells was split 2 days (d) prior to transfection. Using sterile technique, the media was removed and the cells were detached from the dish by the addition of trypsin. One fifth of the cells were then placed onto a new 10-cm dish. Cells were grown in a 37° C. incubator with 5% CO$_2$ in Minimal Essential Media Eagle with 10% Fetal Bovine Serum. After 2 d, cells were approximately 80% confluent. These cells were removed from the dish with trypsin and pelleted in a clinical centrifuge. The pellet was re-suspended in 400 µL complete media and transferred to an electroporation cuvette with a 0.4 cm gap between the electrodes. Supercoiled rat FAAH cDNA (1 µg) was added to the cells and mixed. The voltage for the electroporation was set at 0.25 kV, and the capacitance was set at 960 µF. After electroporation, the cells were diluted into complete media (10 mL) and plated onto four 10-cm dishes. Because of the variability in the efficiency of electroporation, four different concentrations of cells were plated. The ratios used were 1:20, 1:10, and 1:5, with the remainder of the cells being added to the fourth dish. The cells were allowed to recover for 24 h before adding the selection media (complete media with 600 µg/mL G418). After 10 d, dishes were analyzed for surviving colonies of cells. Dishes with well-isolated colonies were used. Cells from individual colonies were isolated and tested. The clones that showed the most FAAH activity, as measured by anandamide hydrolysis, were used for further study.

B. FAAH Assay

T84 frozen cell pellets or transfected SK-N-MC cells (contents of 1×15 cm culture dishes) were homogenized in 50 mL of FAAH assay buffer (125 mM Tris, 1 mM EDTA, 0.2% Glycerol, 0.02% Triton X-100, 0.4 mM Hepes, pH 9). The assay mixture consisted of 50 µL of the cell homogenate, 10 µL of the test compound, and 40 µL of anandamide [1-$^3$H-ethanolamine] ($^3$H-AEA, Perkin-Elmer, 10.3 C$_i$/mmol), which was added last, for a final tracer concentration of 80 nM. The reaction mixture was incubated at rt for 1 h. During the incubation, 96-well Multiscreen filter plates (catalog number MAFCNOB50; Millipore, Bedford, Mass., USA) were loaded with 25 µL of activated charcoal (Multiscreen column loader, catalog number MACL09625, Millipore) and washed once with 100 µL of MeOH. Also during the incubation, 96-well DYNEX MicroLite plates (catalog number NL510410) were loaded with 100 µL of MicroScint40 (catalog number 6013641, Packard Bioscience, Meriden, Conn., USA). After the 1 h incubation, 60 µL of the reaction mixture were transferred to the charcoal plates, which were then assembled on top of the DYNEX plates using Centrifuge Alignment Frames (catalog number MACF09604, Millipore). The unbound labeled ethanolamine was centrifuged through to the bottom plate (5 min at 2000 rpm), which was preloaded with the scintillant, as described above. The plates were sealed and left at rt for 1 h before counting on a Hewlett Packard TopCount.

Results for compounds tested in these assays are summarized in Table 1, as an average of results obtained. Compounds were tested in the free base or trifluoroacetic acid salt form. Compounds tested in the trifluoroacetic acid salt form are indicated as such by a "*" designation after the example number. Where activity is shown as greater than (>) a particular value, the value is the solubility limit of the compound in the assay medium or the highest concentration tested in the assay.

TABLE 1

| Ex. | Assay 1 IC$_{50}$ (μM) | Assay 2 IC$_{50}$ (μM) |
|---|---|---|
| 1 | 0.005 | 0.004 |
| 2* | >10 | >10 |
| 3 | >10 | >10 |
| 4* | 10.000 | 10.000 |
| 5 | >10 | 3.000 |
| 6 | 1.100 | 0.175 |
| 7 | >10 | >10 |
| 8* | 2.400 | 0.620 |
| 9 | 1.300 | 1.300 |
| 10 | 1.400 | 0.300 |
| 11 | 0.370 | 1.600 |
| 12 | 0.300 | >10 |
| 13 | 2.500 | 1.700 |
| 14 | >10 | >10 |
| 15* | >10 | >10 |
| 16 | >10 | >10 |
| 17 | 0.170 | 0.340 |
| 18 | >10 | >10 |
| 19 | >10 | >10 |
| 20 | 1.000 | 1.600 |
| 21 | 1.000 | 0.530 |
| 22 | 1.300 | 0.500 |
| 23 | 0.300 | 0.940 |
| 24 | 0.058 | 0.380 |
| 25 | 0.050 | 0.230 |
| 26 | 0.120 | 0.200 |
| 27 | 0.015 | 0.480 |
| 28 | 0.001 | 0.001 |
| 29 | 0.053 | 0.400 |
| 30 | >10 | 10.000 |
| 31 | 3.000 | 0.900 |
| 32 | 0.360 | 0.430 |
| 33 | 0.034 | 2.000 |
| 34 | 0.030 | 0.054 |
| 35* | 0.160 | 0.350 |
| 36 | 0.200 | 0.430 |
| 37 | 0.140 | 0.820 |
| 38 | 0.027 | 0.005 |
| 39 | 0.013 | 0.010 |
| 40 | 0.003 | 0.004 |
| 41 | 3.000 | 1.000 |
| 42 | 0.030 | 0.024 |
| 43 | 0.004 | 0.001 |
| 44 | 0.013 | 0.027 |
| 45 | 0.700 | 0.043 |
| 46 | 1.600 | 0.615 |
| 47 | 1.000 | 0.250 |
| 48 | 0.001 | 0.005 |
| 49 | 0.009 | 0.033 |
| 50 | 0.009 | 0.097 |
| 51 | 0.200 | 0.062 |
| 52 | 0.100 | 1.000 |
| 53 | 5.999 | 10.000 |
| 54 | >10 | >10 |
| 55 | 0.016 | 0.006 |
| 56 | 0.004 | 0.002 |
| 57 | 3.000 | >10 |
| 58 | 0.300 | 0.700 |
| 59 | >10 | >10 |
| 60 | >10 | >10 |
| 61 | 1.600 | 1.600 |
| 62 | 1.300 | 10.000 |
| 63 | 0.600 | 0.630 |
| 64 | 0.063 | 0.073 |
| 65 | 0.275 | 0.739 |
| 66* | 10.000 | 10.000 |
| 67 | 0.039 | 0.084 |

TABLE 1-continued

| Ex. | Assay 1 IC$_{50}$ (μM) | Assay 2 IC$_{50}$ (μM) |
|---|---|---|
| 68* | 0.849 | 1.225 |
| 69 | 10.000 | >10 |
| 70 | 0.936 | 10.000 |
| 71 | >10 | >10 |
| 72 | >10 | 0.770 |
| 73 | >10 | 10.000 |
| 74 | 1.200 | 1.100 |
| 75 | 0.045 | 0.030 |
| 76 | 0.400 | 0.070 |
| 77 | 5.000 | 7.000 |
| 78 | 0.230 | 0.320 |
| 79 | 0.058 | 0.048 |

While the invention has been illustrated by reference to exemplary and preferred embodiments, it will be understood that the invention is intended not to be limited to the foregoing detailed description, but to be defined by the appended claims as properly construed under principles of patent law.

What is claimed is:

1. Compounds of Formula (I), pharmaceutically acceptable salts of compounds of Formula (I), and pharmaceutically acceptable prodrugs of compounds of Formula (I), (I)

wherein

Q is —(CH$_2$)$_{1-2}$O—, or —(CH$_2$)$_{1-2}$OCH$_2$—;

n$^1$ is 1;

Ar$^1$ is a ring system selected from benzo[d]isoxazolyl, 1H-pyrrolo[2,3-b]pyridinyl, 2,1,3-benzoxadiazolyl, imidazo[1,2-a]pyridinyl, imidazo[1,2-b]pyridazinyl, isoquinolinyl, and pyridyl optionally substituted with triazolyl; wherein each ring system is optionally substituted with halo;

Ar$^2$ is:

(i) phenyl optionally substituted with one or two R$^d$ moieties;

wherein each R$^d$ moiety is independently selected from —C$_{1-4}$alkyl, —OC$_{1-4}$alkyl, halo, —CF$_3$, —OCF$_3$, and —S(O)(O)C$_{1-4}$alkyl, or two adjacent R$^d$ moieties taken together form —OCH$_2$O— or —OCF$_2$O—;

(ii) phenyl substituted at the 3- or 4-position with -L-Ar$^3$, said phenyl optionally substituted with one additional R$^d$ moiety, wherein:

L is —O—(CH$_2$)$_{0-1}$— or a covalent bond;

Ar$^3$ is:

(i) phenyl optionally substituted with one or two R$^d$ moieties; or (ii) pyridyl optionally substituted with one or two R$^d$ moieties;

(iii) naphthyl;

(iv) 5,6,7,8-tetrahydro-naphthalenyl; or (v) quinolinyl optionally substituted with a halo.

2. Compounds of claim 1, wherein Ar$^1$ is a ring system selected from benzo[d]isoxazol-3-yl, 2,1,3-benzoxadiazol-4- yl, 4-chloropyridin-3-yl, imidazo[1,2-b]pyridazin-3-yl, pyridin-3-yl, 6-[1,2,3]triazol-2-yl-pyridin-3-yl,

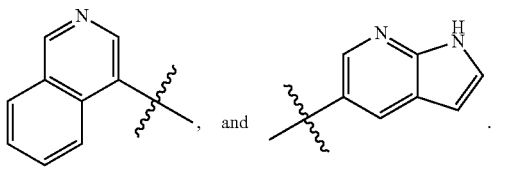 [SMILES: *c1cncc2ccccc12 ; *c1cnc2[nH]ccc2c1]

3. Compounds of claim 1, wherein Q is —CH$_2$CH$_2$O—.
4. Compounds of claim 1, wherein Q is —CH$_2$O—.
5. Compounds of claim 1, wherein Ar$^2$ is phenyl substituted at the 3- or 4-position with -L-Ar$^3$.
6. Compounds of claim 5, wherein L is —O— and Ar$^3$ is phenyl optionally substituted with one or two R$^d$ moieties.
7. Compounds of claim 5, wherein L is —O— and Ar$^3$ is pyridyl optionally substituted with one or two R$^d$ moieties.
8. Compounds of claim 5, wherein Q is —CH$_2$CH$_2$O—.
9. Compounds of claim 5, wherein Q is —CH$_2$O—.
10. Compounds of claim 1, wherein Ar$^2$ is phenyl optionally substituted with one or two R$^d$.
11. Compounds of claim 10, wherein Q is —CH$_2$CH$_2$O—.
12. Compounds of claim 1, selected from the group consisting of:

3-{2-[3-(4-Chloro-phenoxy)-phenoxy]-ethyl}-azetidine-1-carboxylic acid imidazo[1,2-b]pyridazin-3-ylamide;
3-Phenoxymethyl-azetidine-1-carboxylic acid pyridin-3-ylamide;
3-(4-Bromo-phenoxymethyl)-azetidine-1-carboxylic acid pyridin-3-ylamide;
3-(3-Ethoxy-phenoxymethyl)-azetidine-1-carboxylic acid pyridin-3-ylamide;
3-(4-Trifluoromethoxy-phenoxymethyl)-azetidine-1-carboxylic acid pyridin-3-ylamide;
3-(3-Trifluoromethoxy-phenoxymethyl)-azetidine-1-carboxylic acid pyridin-3-ylamide;
3-(Benzo[1,3]dioxol-5-yloxymethyl)-azetidine-1-carboxylic acid pyridin-3-ylamide;
3-(3-Trifluoromethyl-phenoxymethyl)-azetidine-1-carboxylic acid pyridin-3-ylamide;
3-(Quinolin-2-yloxymethyl)-azetidine-1-carboxylic acid pyridin-3-ylamide;
3-(3-Chloro-4-trifluoromethyl-phenoxymethyl)-azetidine-1-carboxylic acid pyridin-3-ylamide;
3-(3-Ethynyl-phenoxymethyl)-azetidine-1-carboxylic acid pyridin-3-ylamide;
3-(3-Butoxy-phenoxymethyl)-azetidine-1-carboxylic acid pyridin-3-ylamide;
3-(5,6,7,8-Tetrahydro-naphthalen-2-yloxymethyl)-azetidine-1-carboxylic acid pyridin-3-ylamide;
3-(Quinolin-7-yloxymethyl)-azetidine-1-carboxylic acid pyridin-3-ylamide;
3-(Quinolin-6-yloxymethyl)-azetidine-1-carboxylic acid pyridin-3-ylamide;
3-(4-Phenoxy-phenoxymethyl)-azetidine-1-carboxylic acid pyridin-3-ylamide;
3-(3-Phenoxy-phenoxymethyl)-azetidine-1-carboxylic acid pyridin-3-ylamide;
3-(Biphenyl-4-yloxymethyl)-azetidine-1-carboxylic acid pyridin-3-ylamide;
3-(4-Benzyloxy-phenoxymethyl)-azetidine-1-carboxylic acid pyridin-3-ylamide;
3-(Naphthalen-2-yloxymethyl)-azetidine-1-carboxylic acid pyridin-3-ylamide;
3-(3,4-Dichloro-phenoxymethyl)-azetidine-1-carboxylic acid pyridin-3-ylamide;
3-(8-Chloro-quinolin-2-yloxymethyl)-azetidine-1-carboxylic acid pyridin-3-ylamide;
3-(3-Benzyloxy-phenoxymethyl)-azetidine-1-carboxylic acid pyridin-3-ylamide;
3-[3-(4-Methanesulfonyl-phenoxy)-phenoxymethyl]-azetidine-1-carboxylic acid pyridin-3-ylamide;
3-[3-(4-Trifluoromethoxy-phenoxy)-phenoxymethyl]-azetidine-1-carboxylic acid pyridin-3-ylamide;
3-[3-(4-Chloro-phenoxy)-phenoxymethyl]-azetidine-1-carboxylic acid pyridin-3-ylamide;
3-{2-[3-(4-Methanesulfonyl-phenoxy)-phenoxy]-ethyl}-azetidine-1-carboxylic acid pyridin-3-ylamide;
3-{2-[3-(4-Chloro-phenoxy)-phenoxy]-ethyl}-azetidine-1-carboxylic acid (4-chloro-pyridin-3-yl)-amide;
3-{2-[3-(4-Trifluoromethoxy-phenoxy)-phenoxy]-ethyl}-azetidine-1-carboxylic acid pyridin-3-ylamide;
3-[2-(4-Trifluoromethoxy-phenoxy)-ethyl]-azetidine-1-carboxylic acid pyridin-3-ylamide;
3-[2-(3-Trifluoromethoxy-phenoxy)-ethyl]-azetidine-1-carboxylic acid pyridin-3-ylamide;
3-[2-(3-Phenoxy-phenoxy)-ethyl]-azetidine-1-carboxylic acid pyridin-3-ylamide;
3-[2-(3-Butoxy-phenoxy)-ethyl]-azetidine-1-carboxylic acid pyridin-3-ylamide;
3-[2-(3,4-Dichloro-phenoxy)-ethyl]-azetidine-1-carboxylic acid pyridin-3-ylamide;
3-[2-(Naphthalen-2-yloxy)-ethyl]-azetidine-1-carboxylic acid pyridin-3-ylamide;
3-[2-(Quinolin-2-yloxy)-ethyl]-azetidine-1-carboxylic acid pyridin-3-ylamide;
3-[2-(3-Ethynyl-phenoxy)-ethyl]-azetidine-1-carboxylic acid pyridin-3-ylamide;
3-{2-[3-(4-Chloro-phenoxy)-phenoxy]-ethyl}-azetidine-1-carboxylic acid isoquinolin-4-ylamide;
3-{2-[3-(4-Chloro-phenoxy)-phenoxy]-ethyl}-azetidine-1-carboxylic acid (6-[1,2,3]triazol-2-yl-pyridin-3-yl)-amide;
3-{2-[3-(4-Chloro-phenoxy)-phenoxy]-ethyl}-azetidine-1-carboxylic acid imidazo[1,2-a]pyridin-6-ylamide;
3-{2-[3-(4-Chloro-phenoxy)-phenoxy]-ethyl}-azetidine-1-carboxylic acid imidazo[1,2-a]pyridin-3-ylamide;
3-{2-[3-(4-Chloro-phenoxy)-phenoxy]-ethyl}-azetidine-1-carboxylic acid benzo[d]isoxazol-3-ylamide;
3-{2-[3-(4-Chloro-phenoxy)-phenoxy]-ethyl}-azetidine-1-carboxylic acid pyridin-3-ylamide;
3-[2-(4-Chloro-3-trifluoromethyl-phenoxy)-ethyl]-azetidine-1-carboxylic acid pyridin-3-ylamide;
3-[2-(3-Trifluoromethyl-phenoxy)-ethyl]-azetidine-1-carboxylic acid pyridin-3-ylamide;
3-[2-(3,5-Dichloro-phenoxy)-ethyl]-azetidine-1-carboxylic acid pyridin-3-ylamide;
3-{2-[3-(5-Chloro-pyridin-2-yloxy)-phenoxy]-ethyl}-azetidine-1-carboxylic acid (4-chloro-pyridin-3-yl)-amide;
3-[2-(4-Chloro-benzyloxy)-ethyl]-azetidine-1-carboxylic acid (4-chloro-pyridin-3-yl)-amide;
3-[2-(4-Chloro-benzyloxy)-ethyl]-azetidine-1-carboxylic acid pyridin-3-ylamide;
3-[2-(3,4-Dichloro-benzyloxy)-ethyl]-azetidine-1-carboxylic acid (4-chloro-pyridin-3-yl)-amide;
3-[2-(3,4-Dichloro-benzyloxy)-ethyl]-azetidine-1-carboxylic acid pyridin-3-ylamide;
3-(2-Benzyloxy-ethyl)-azetidine-1-carboxylic acid pyridin-3-ylamide; and
3-(2-Benzyloxy-ethyl)-azetidine-1-carboxylic acid (4-chloro-pyridin-3-yl)-amide;
and pharmaceutically acceptable salts and prodrugs thereof.

13. A pharmaceutical composition comprising:
(a) a therapeutically effective amount of at least one chemical entity selected from the group consisting of compounds of Formula (I), pharmaceutically acceptable salts of compounds of Formula (I), and pharmaceutically acceptable prodrugs of compounds of Formula (I);

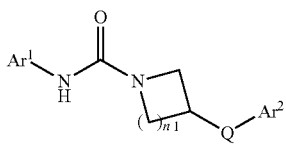

(I)

wherein
Q is —$(CH_2)_{1-2}$O—, or —$(CH_2)_{1-2}OCH_2$—;
$n^1$ is 1;
$Ar^1$ is a ring system selected from benzo[d]isoxazolyl, 1H-pyrrolo[2,3-b]pyridinyl, 2,1,3-benzoxadiazolyl, imidazo[1,2-a]pyridinyl, imidazo[1,2-b]pyridazinyl, isoquinolinyl, and pyridyl optionally substituted with triazolyl; wherein each ring system is optionally substituted with halo;
$Ar^2$ is:
  (i) phenyl optionally substituted with one or two $R^d$ moieties;
  wherein each $R^d$ moiety is independently selected from —$C_{1-4}$alkyl, —$OC_{1-4}$alkyl, halo, —$CF_3$, —$OCF_3$, and —$S(O)(O)C_{1-4}$alkyl, or two adjacent $R^d$ moieties taken together form —$OCH_2O$— or —$OCF_2O$—;
  (ii) phenyl substituted at the 3- or 4-position with -L-$Ar^3$, said phenyl optionally substituted with one additional $R^d$ moiety, wherein:
  L is —O—$(CH_2)_{0-1}$— or a covalent bond;
  $Ar^3$ is:
  (i) phenyl optionally substituted with one or two $R^d$ moieties; or
  (ii) pyridyl optionally substituted with one or two $R^d$ moieties;
  (iii) naphthyl;
  (iv) 5,6,7,8-tetrahydro-naphthalenyl; or
  (v) quinolinyl optionally substituted with a halo; and
(b) a pharmaceutically acceptable excipient.

14. A pharmaceutical composition according to claim 13, further comprising: an analgesic selected from the group consisting of opioids and non-steroidal anti-inflammatory drugs.

15. A pharmaceutical composition according to claim 13, further comprising: an additional active ingredient selected from the group consisting of aspirin, acetaminophen, opioids, ibuprofen, naproxen, COX-2 inhibitors, gabapentin, pregabalin, and tramadol.

* * * * *